(12) United States Patent
Mueller et al.

(10) Patent No.: US 11,166,986 B2
(45) Date of Patent: Nov. 9, 2021

(54) USE OF HELIOCBACTER PYLORI EXTRACT FOR TREATING OR PREVENTING INFLAMMATORY BOWEL DISEASES AND COELIAC DISEASE

(71) Applicant: UNIVERSITAT ZURICH, Zurich (CH)

(72) Inventors: Anne Mueller, Dübendorf (CH); Daniela Engler-Anders, Zurich (CH)

(73) Assignee: UNIVERSITAT ZURICH, Zurich (CH)

( * ) Notice: Subject to any disclaimer, the term of this patent is extended or adjusted under 35 U.S.C. 154(b) by 448 days.

(21) Appl. No.: 15/115,391

(22) PCT Filed: Jan. 30, 2015

(86) PCT No.: PCT/IB2015/050705
§ 371 (c)(1),
(2) Date: Jul. 29, 2016

(87) PCT Pub. No.: WO2015/114576
PCT Pub. Date: Aug. 6, 2015

(65) Prior Publication Data
US 2017/0007649 A1    Jan. 12, 2017

(30) Foreign Application Priority Data
Jan. 31, 2014   (EP) ..................... 14153366

(51) Int. Cl.
| | |
|---|---|
| *A61K 35/74* | (2015.01) |
| *A61K 38/16* | (2006.01) |
| *C07K 14/205* | (2006.01) |
| *A61K 9/00* | (2006.01) |

(52) U.S. Cl.
CPC ............ *A61K 35/74* (2013.01); *A61K 9/0019* (2013.01); *A61K 9/0053* (2013.01); *A61K 38/164* (2013.01); *C07K 14/205* (2013.01)

(58) Field of Classification Search
CPC ...... A61K 35/74; A61K 9/0019; A61K 9/005; A61K 9/0053; A61K 38/164; C07K 14/205
USPC ....................................................... 424/780
See application file for complete search history.

(56) References Cited

U.S. PATENT DOCUMENTS

| 2002/0198162 A1* | 12/2002 | Punnonen ............ C07K 14/005 514/44 A |
| 2009/0304577 A1* | 12/2009 | Matossian-Rogers ....... C07K 16/2809 424/1.49 |
| 2013/0121915 A1* | 5/2013 | Paas .......................... B82Y 5/00 424/9.1 |
| 2017/0007683 A1 | 1/2017 | Mueller et al. |

FOREIGN PATENT DOCUMENTS

| EP | 1 582 215 | 10/2005 |
| WO | WO 02/04017 | 1/2002 |
| WO | WO 03/018054 | 3/2003 |
| WO | WO 2015/114575 | 8/2015 |

OTHER PUBLICATIONS

Kotlyar et al. World J Gastroenterol Aug. 28, 2014; 20(32): 11023-11032.*
Burgess et al. The Journal of Cell Biology, vol. 111, Nov. 1990 2129-2138.*
Lazaret al. Molecular and Cellular Biology, Mar. 1988, p. 1247-1252.*
McCoy, Food Allergy or Digestive Problem?, Sep. 10, 2012, Available online at: www.everydayhealth.com/allergies/food-allergies-and-digestive-problems.aspx.*
ATCC, Product Sheet, Wilcoxina rehmii (ATCC® 60190™), 2012.*
Kyburz, A. et al. "*Helicobacter pylori* and its secreted immunomodulator VacA protect against anaphylaxis in experimental models of food allergy" *Clinical and Experimental Allergy*, 2017, pp. 1331-1341, vol. 47.
Van Wijck, Y. et al. "Therapeutic Application of an Extract of *Helicobacter pylori* Ameliorates the Development of Allergic Airway Disease" *The Journal of Immunology*, 2018, pp. 1570-1579, vol. 200.
Altobelli, A. et al. "*Helicobacter pylori* VacA Targets Myeloid Cells in the Gastric Lamina Propria to Promote Peripherally Induced Regulatory T-Cell Differentiation and Persistent Infection" *mBio*, Mar./Apr. 2019, pp. 1-13, vol. 10, Issue 2, e00261-19.
De Bernard, M. et al. "Identification of the *Helicobacter pylori* VacA Toxin Domain Active in the Cell Cytosol" *Infection and Immunity*, Dec. 1998, pp. 6014-6016, vol. 66, No. 12.
Garner, J. A. et al. "Binding and Internalization of the *Helicobacter pylori* Vacuolating Cytotoxin by Epithelial Cells" *Infection and Immunity*, Oct. 1996, pp. 4197-4203, vol. 64, No. 10.
Clarke, K. et al. "Allergic and Immunologic Perspectives of Inflammatory Bowel Disease" *Clinical Reviews in Allergy & Immunology*, May 12, 2018, pp. 1-15.
Konturek, P. C. et al. "*Helicobacter pylori* as a protective factor against food allergy" Med Sci Monit, Sep. 1, 2008, pp. CR453-CR458, vol. 14, No. 9.
Product information document from American Type Culture Collection (ATCC), "*Helicobacter pylori* (Marshall et al.) Goodwin et al. (ATCC® 49503™)", Strain Designation 60190, Mar. 31, 2017, pp. 1-2.
Arnold, I.C. et al. "*Helicobacter pylori* infection prevents allergic asthma in mouse models through the induction of regulatory T cells" *The Journal of Clinical Investigation*, Aug. 2011, pp. 3088-3093, vol. 121, No, 8.

(Continued)

*Primary Examiner* — Jennifer M. H. Tichy
(74) *Attorney, Agent, or Firm* — Saliwanchik, Lloyd & Eisenschenk

(57) ABSTRACT

The present invention is directed to polypeptides and compositions thereof useful for the prevention or treatment of an inflammatory bowel disease in particular Crohn's disease or ulcerative colitis (UC), and of coeliac disease. More particularly, the invention relates to agents and compositions thereof that useful for the prevention and treatment of hypersensitivity and/or hyperirritability of the colon and/or small intestine.

13 Claims, 8 Drawing Sheets
Specification includes a Sequence Listing.

(56) References Cited

OTHER PUBLICATIONS

Arnold, I.C. et al. "Tolerance Rather Than Immunity Protects From *Helicobacter pylori*-Induced Gastric Preneoplasia" Gastroenterology, Jan. 2011, pp. 199-209 and 209.e1-209.e8, vol. 140, No. 1.

Bhaduri, S. et al. "Simple and Rapid Method for Disruption of Bacteria for Protein Studies" *Applied and Environmental Microbiology*, Oct. 1983, pp. 941-943, vol. 46, No. 4.

Chen, Y. et al. "Inverse Associations of *Helicobacter pylori* With Asthma and Allergy" *Arch Internal Medicine*, Apr. 23, 2007, pp. 821-827, vol. 167.

Chen, Y. et al. "*Helicobacter pylori* colonization is inversely associated with childhood asthma" *Journal of Infectious Diseases*, Aug. 15, 2008, pp. 553-560, vol. 198, No. 4.

Cover, T.L. et al. "Characterization of and Human Serologic Response to Proteins in *Helicobacter pylori* Broth Culture Supernatants with Vacuolizing Cytotoxin Activity" *Infection and Immunity*, Mar. 1990, pp. 603-610, vol. 58, No. 3.

Cover, T.L. et al. "Purification and Characterization of the Vacuolating Toxin from Helicobacter pylon" *The Journal of Biological Chemistry*, May 25, 1992, pp. 10570-10575, vol. 267, No. 15.

Cover, T.L. et al. "Acid-induced Dissociation of VacA, the *Helicobacter pylori* Vacuolating Cytotoxin, Reveals Its Pattern of Assembly" *The Journal of Cell Biology*, Aug. 25, 1997, pp. 759-769, vol. 138, No. 4.

DeBernard, M. et al. "The multiple cellular activities of the VacA cytotoxin of *Helicobacter pylori*" *International Journal of Medical Microbiology*, 2004, pp. 589-597, vol. 293.

Engler, D. et al. "Beneficial effects of early childhood *Helicobacter pylori* infection on the development of allergic and chronic inflammatory disorders" #197, Allergy, 2012, p. 93, vol. 67, Suppl. 96.

Engler, D. et al. "Effective treatment of allergic airway inflammation with *Helicobacter pylon* immunomodulators requires BATF3-dependent dendritic cells and IL-10" *Proceedings of the National Academy of Sciences*, Aug. 12, 2014, pp. 11810-11815, vol. 111, No. 32.

Fischer, W. et al. "Novel activities of the *Helicobacter pylori* vacuolating cytotoxin: from epithelial cells towards the immune system" *International Journal of Medical Microbiology*, 2004, pp. 539-547, vol. 293, Nos. 7-8.

Gangwer, K.A. et al. "Crystal structure of the Helicobacter pylori vacuolating toxin p55 domain" *Proceedings of the National Academy of Sciences*, Oct. 9, 2007, pp. 16293-16298, vol. 104, No. 41.

González-Rivera, C. et al. "Reconstitution of *Helicobacter pylori* VacA toxin from purified components" *Biochemistry*, Jul. 13, 2010, pp. 5743-5752, vol. 49, No. 27.

Harris, P.R. et al. "*Helicobacter pylori* Gastritis in Children Is Associated With a Regulatory T-Cell Response" *Gastroenterology*, 2008, pp. 491-499, vol. 134, No. 2.

Kelemen, M.V. et al. "Controlled Cell Disruption: A Comparison of the Forces Required to Disrupt Different Micro-Organisms" *Journal of Cell Science*, 1979, pp. 431-441, vol. 35.

Khinchi, M.S. et al. "Clinical efficacy of sublingual and subcutaneous birch pollen allergen-specific immunotherapy: a randomized, placebo-controlled, double-blind, double-dummy study" *Allergy*, Jan. 2004, pp. 45-53, vol. 59, No. 1.

Malfertheiner, P. et al. "Safety and Immunogenicity of an Intramuscular *Helicobacter pylori* Vaccine in Noninfected Volunteers: A Phase I Study" *Gastroenterology*, 2008, pp. 787-795, vol. 135, No. 3.

McClain, M.S. et al. "Essential Role of GXXXG Motif for Membrane Channel Formation by Helicobacter pylori Vacuolating Toxin" *The Journal of Biological Chemistry*, Apr. 4, 2003, pp. 12101-12108, vol. 278, No. 14.

Oertli, M. et al. "DC-derived IL-18 drives Treg differentiation, murine *Helicobacter pylori*-specific immune tolerance, and asthma protection" *The Journal of Clinical Investigation*, Mar. 2012, pp. 1082-1096, vol. 122, No. 3.

Oertli, M. et al. "*Helicobacter pylori* γ-glutamyl transpeptidase and vacuolating cytotoxin promote gastric persistence and immune tolerance" *Proceedings of the National Academy of Sciences*, Feb. 19, 2013, pp. 3047-3052 and supporting information pp. 1-7, vol. 110, No. 8.

Oertli, M. et al. "Dendritic cell-derived interleukin-18 drives regulatory T-cell differentiation and induces Helicobacter pylorispecific immune tolerance and asthma protection" *WIRM*, 2012, W27—poster abstract, p. 1.

Parsonnet, J. et al. "*Helicobacter pylori* Infection and the Risk of Gastric Carcinoma" *New England Journal of Medicine*, Oct. 17, 1991, pp. 1127-1131, vol. 325, No. 16.

Pfefferle, P.I. et al. "Microbial influence on tolerance and opportunities for intervention with prebiotics/probiotics and bacterial lysates" *Journal of Allergy Clinical Immunology*, Jun. 2013, pp. 1453-1463, vol. 131, No. 6.

Sayi, A. et al. "TLR-2-Activated B Cells Suppress Helicobacter-Induced Preneoplastic Gastric Immunopathology by Inducing T Regulartory-1 Cells" *The Journal of Immunology*, 2011, pp. 878-890, vol. 186.

Sun, J. et al. "Impact of DC40 Ligand, B Cells, and Mast Cells in Peanut-Induced Anaphylactic Responses" *The Journal of Immunology*, 2007, pp. 6696-6703, vol. 179.

Vinion-Dubiel, A.D. et al. "A Dominant Negative Mutant of Helicobacter pylori Vacuolating Toxin (VacA) Inhibits VacA-induced Cell Vacuolation" *The Journal of Biological Chemistry*, Dec. 31, 1999, pp. 37736-37742, vol. 274, No. 53.

Engler, D.B. et al. "Beneficial effects of early childhood *Helicobacter pylori* infection on the development of allergic and chronic inflammatory disorders" *WIRM*, 2012, P44—poster abstract, pp. 1-2.

Written Opinion in International Application No. PCT/IB2015/050705, Jun. 8, 2015, pp. 1-7.

Huang, J.Q. et al. "Meta-Analysis of the Relationship Between cagA Seropositivity and Gastric Cancer" *Gastroenterology*, Dec. 2003, pp. 1636-1644, vol. 125, No. 6.

Luther, J.L. et al. "Association Between *Helicobacter pylori* Infection and Inflammatory Bowel Disease: A Meta-analysis and Systematic Review of the Literature" *Inflammatory Bowel Diseases*, Jun. 2010, pp. 1077-1084, vol. 16, No. 6.

Oertili, M. et al. "MicroRNA-155 Is Essential for the T Cell-Mediated Control of *Helicobacter pylori* Infection and for the Induction of Chronic Gastritis and Colitis" *The Journal of Immunology*, 2011, pp. 3578-3586, vol. 187.

Database BIOSIS [online], Accession No. PREV200600211957, "Helicobacter pylori extract upregulates PTEN and Cox2 in gastric epithelial cells: Implications for cell proliferation, survival and injury healing" May 2005, p. 1, XP-002739966.

Database WPI [online], Accession No. 2009-A66714, 2008, pp. 1-2, XP-002739965.

\* cited by examiner

A

**Q48245 *H. pylori* strain ATCC 49503/60190 (Cover et. al., 1994) (SEQ ID NO: 1)**

AFFTTVIIPAIVGGIATGTAVGTVSGLLGWGLKQAEEANKTPDKPDKVWRIQAGKGFNEFPN
KEYDLYKSLLSSKIDGGWDWGNAATHYWIKGGQWNKLEVDMKDAVGTYKLSGLRNFTGG
DLDVNMQKATLRLGQFNGNSFTSYKDSADRTTRVDFNAKNILIDNFLEINNRVGSGAGRKA
SSTVLTLQASEGITSSKNAEISLYDGATLNLASNSVKLNGNVWMGRLQYVGAYLAPSYSTIN
TSKVTGEVNFNHLTVGDHNAAQAGIIASNKTHIGTLDLWQSAGLNIIAPPEGGYKDKPNNTP
SQSGAKNDKQESSQNNSNTQVINPPNSTQKTEVQPTQVIDGPFAGGKDTVVNIDRINTKAD
GTIKVGGFKASLTTNAAHLNIGKGGVNLSNQASGRTLLVENLTGNITVDGPLRVNNQVGGYA
LAGSSANFEFKAGVDTKNGTATFNNDISLGRFVNLKVDAHTANFKGIDTGNGGFNTLDFSG
VTNKVNINKLITASTNVAVKNFNINELIVKTNGVSVGEYTHFSEDIGSQSRINTVRLETGTRSIF
SGGVKFKSGEKLVIDEFYYSPWNYFDARNIKNVEITRKFASSTPENPWGTSKLMFNNLTLGQ
NAVMDYSQFSNLTIQGDFINNQGTINYLVRGGKVATLNVGNAAAMMFNNDIDSATGFYKPLI
KINSAQDLIKNTEHVLLKAKIIGYGNVSTGTNGISNVNLEEQFKERLALYNNNNRMDTCVVRN
TDDIKACGMAIGNQSMVNNPDNYKYLIGKAWKNIGISKTANGSKISVYYLGNSTPTENGGNT
TNLPTNTTNNARFASYALIKNAPFAHSATPNLVAINQHDFGTIESVFELANRSKDIDTLYANS
GAQGRDLLQTLLIDSHDAGYARTMIDATSANEITKQLNTATTTLNNIASLEHKTSSLQTLSLSN
AMILNSRLVNLSRRHTNNIDSFAKRLQALKDQRFASLESAAEVLYQFAP

B

**s2m2 VacA from strain *H. pylori* Tx30a (*Atherton et al., 1995, J. Biol. Chem.., 270 (30), 17771-17777*) (SEQ ID NO: 2)**

MEIQQTHRKINRPIISLALVGVLMGTELGANTPNDPIHSESRAFFTTVIIPAIVGGIATGAAVGT
VSGLLSWGLKQAEQANKAPDKPDKVWRIQAGRGFDNFPHKQYDLYKSLLSSKIDGGWDW
GNAARHYWVKDGQWNKLEVDMQNAVGTYNLSGLINFTGGDLDVNMQKATLRLGQFNGNS
FTSFKDGANRTTRVNFDAKNILIDNFVEINNRVGSGAGRKASSTVLTLKSSEKITSRENAEISL
YDGATLNLVSSSNQSVDLYGKVWMGRLQYVGAYLAPSYSTIDTSKVQGEMNFRHLAVGDQ
NAAQAGIIANKKTNIGTLDLWQSAGLSIITPPEGGYESKTKDNPQNNPKNDAQKTEIQPTQVI
DGPFAGGKDTVVNIFHLNTKADGTLRAGGFKASLSTNAAHLHIGEGGVNLSNQASGRTLLV
ENLTGNITVEGTLRVNNQVGGAAIAGSSANFEFKAGEDTNNATATFNNDIHLGKAVNLRVDA
HTANFNGNIYLGKSTNLRVNGHTAHFKNIDATKSDNGLNTSTLDFSGVTDKVNINKLTTAAT
NVNIKNFDIKELVVTTRVQSFGQYTIFGENIGDKSRIGVVSLQTGYSPAYSGGVTFKGGKKLV
IDEIYHAPWNYFDARNVTDVEINKRILFGAPGNIAGKTGLMFNNLTLNSNASMDYGKDLDLTI
QGHFTNNQGTMNLFVQDGRVATLNAGHQASMIFNNLVDSTTGFYKPLIKINNAQNLTKNKE
HVLVKARNIDYNLVGVQGASYDNISASNTNLQEQFKERLALYNNNNRMDTCVVRKDNLNDI
KACGMAIGNQSMVNNPENYKYLEGKAWKNTGINKTANNTTIAVNLGNNSTPTNSTTDTTNL
PTNTTNNARFASYALIKNAPFAHSATPNLVAINQHDFGTIESVFELANRSSDIDTLYANSGAQ
GRDLLQTLLIDSHDAGYARTMIDATSANEITQQLNAATTTLNNIASLEHKTSGLQTLSLSNAMI
LNSRLVNLSRKHTNHIDSFAKRLQALKDQRFASLESAAEVLYQFAPKYEKPTNVWANAIGGT
SLNNGSNASLYGTSAGVDAYLNGEVEAIVGGFGSYGYSSFSNQANSLNSGANNTNFGVYS
RIFANQHEFDFEAQGALGSDQSSLNFKSALLQDLNQSYHYLAYSATTRASYGYDFAFFRNA
LVLKPSVGVSYNHLGSTNFKSNSNQVALSNGSSSQHLFNANANVEARYYYGDTSYFYMNA
GVLQEFARFGSNNAVSLNTFKVNATRNPLNTHARVMMGGELQLAKEVFLNLGVVYLHNLIS
NASHFASNLGMRYSF

Figure 3

C   s1m1 VacA from strain *H. pylori* G27 (*Baltrus et al., 2009, J. Bacteriol., 191(1):447-8*) (SEQ ID NO: 3)

MEIQQTHRKMNRPLVSLVLAGALISAIPQESHAAFFTTVIIPAIVGGIATGTAVGTVSGLLSWGL
KQAEEANKNPDKPDKVWRIQAGKGFNEFPNKEYDLYKSLLSSKIDGGWDWGNAARHYWVK
GGQWNKLEVDMKDAVGTYKLSGLRNFTGGDLDVNMQKATLRLGQFNGNSFTSYKDAADR
TTRVNFNAKNISIDNFVEINNRVGSGAGRKASSTVLTLQASEGITSDKNAEISLYDGATLNLAS
SSVKLMGNVWMGRLQYVGAYLAPSYSTINTSKVTGEVNFNHLTVGDKNAAQAGIIASNKTHI
GTLDLWQSAGLNIIAPPEGGYKDKPNNTPSQSGTKNDKNESAKNDKQESSQNNSNTQVINP
PNSTQKTEIQPTQVIDGPFAGGKDTVVNINRINTNADGTIRVGGFKASLTTNAAHLHIGKGGV
NLSNQASGRTLLVENLTGNITVDGPLRVNNQVGGYALAGSSANFEFKAGVDTKNGTATFNN
DISLGRFVNLKVDAHTANFKGIDTGNGGFNTLDFSGVTDKVNINKLITASTNVAVKNFNINELI
VKTNGISVGEYTHFSEDIGSQSRINTVRLETGTRSIFSGGVKFKSGEKLVIDEFYYSPWNYFD
ARNVKNVEITRKFASSTPENPWGTSKLMFNNLTLGQNAVMDYSQFSNLTIQGDFINNQGTIN
YLVRGGKVATLSVGNAAAMMFNNDIDSATGFYKPLIKINSAQDLIKNTEHVLLKAKIIGYGNVS
TGTNSISNVNLEEQFKERLALYNNNNRMDTCVVRNTDDIKACGMAIGNQSMVNNPDNYKYLI
GKAWKNIGISKTANGSKISVYYLGNSTPTENGGNTTNLPTNTTNNARSANYALVKNAPFAHS
ATPNLVAINQHDFGTIESVFELANRSKDIDTLYTHSGVQGRDLLQTLLIDSHDAGYARQMIDN
TSTGEITKQLNAATDALNNIASLEHKTSGLQTLSLSNAMILNSRLVNLSRKHTNHIDSFAQRLQ
ALKGQRFASLESAAEVLYQFAPKYEKPTNVWANAIGGASLNNGGNASLYGTSAGVDAYLNG
EVEAIVGGFGSYGYSSFSNRANSLNSGANNANFGVYSRIFANQHEFDFEAQGALGSDQSSL
NFKSALLQDLNQSYHYLAYSAATRASYGYDFAFFRNALVLKPSVGVSYNHLGSTNFKSSSN
QVALKNGSSSQHLFNANANVEARYYYGDTSYFYMNAGVLQEFARFGSNNAASLNTFKVNT
ARNPLNTHARVMMGGELQLAKEVFLNLGVVYLHNLISNIGHFASNLGMRYSF

D   s1m1 VacA from strain *H. pylori* 60190 (*Cover et al., 1994, J. Biol. Chem., 269(14):10566-73*) (SEQ ID NO: 4)

MEIQQTHRKINRPLVSLALVGALVSITPQQSHAAFFTTVIIPAIVGGIATGTAVGTVSGLLGWGL
KQAEEANKTPDKPDKVWRIQAGKGFNEFPNKEYDLYKSLLSSKIDGGWDWGNAATHYWIKG
GQWNKLEVDMKDAVGTYKLSGLRNFTGGDLDVNMQKATLRLGQFNGNSFTSYKDSADRTT
RVDFNAKNILIDNFLEINNRVGSGAGRKASSTVLTLQASEGITSSKNAEISLYDGATLNLASNSV
KLNGNVWMGRLQYVGAYLAPSYSTINTSKVTGEVNFNHLTVGDHNAAQAGIIASNKTHIGTLD
LWQSAGLNIIAPPEGGYKDKPNNTPSQSGAKNDKQESSQNNSNTQVINPPNSTQKTEVQPT
QVIDGPFAGGKDTVVNIDRINTKADGTIKVGGFKASLTTNAAHLNIGKGGVNLSNQASGRTLLV
ENLTGNITVDGPLRVNNQVGGYALAGSSANFEFKAGVDTKNGTATFNNDISLGRFVNLKVDA
HTANFKGIDTGNGGFNTLDFSGVTNKVNINKLITASTNVAVKNFNINELIVKTNGVSVGEYTHF
SEDIGSQSRINTVRLETGTRSIFSGGVKFKSGEKLVIDEFYYSPWNYFDARNIKNVEITRKFAS
STPENPWGTSKLMFNNLTLGQNAVMDYSQFSNLTIQGDFINNQGTINYLVRGGKVATLNVGN
AAAMMFNNDIDSATGFYKPLIKINSAQDLIKNTEHVLLKAKIIGYGNVSTGTNGISNVNLEEQFK
ERLALYNNNNRMDTCVVRNTDDIKACGMAIGNQSMVNNPDNYKYLIGKAWKNIGISKTANGS
KISVYYLGNSTPTENGGNTTNLPTNTTNNARFASYALIKNAPFAHSATPNLVAINQHDFGTIES
VFELANRSKDIDTLYANSGAQGRDLLQTLLIDSHDAGYARTMIDATSANEITKQLNTATTTLNNI
ASLEHKTSSLQTLSLSNAMILNSRLVNLSRRHTNNIDSFAKRLQALKDQRFASLESAAEVLYQF
APKYEKPTNVWANAIGGASLNNGGNASLYGTSAGVDAYLNGQVEAIVGGFGSYGYSSFNNQ
ANSLNSGANNTNFGVYSRIFANQHEFDFEAQGALGSDQSSLNFKSALLRDLNQSYNYLAYSA
ATRASYGYDFAFFRNALVLKPSVGVSYNHLGSTNFKSNSTNKVALSNGSSSQHLFNASANVE
ARYYYGDTSYFYMNAGVLQEFANFGSSNAVSLNTFKVNATRNPLNTHARVMMGGELKLAKE
VFLNLGVVYLHNLISNIGHFASNLGMRYSF

Figure 3 (continued)

E   **s1m1 VacA from strain *H. pylori* 26695 (*Tomb et al., 1997, Nature, 388(6642):539-47*) (SEQ ID NO: 5)**

MEIQQTHRKINRPLVSLALVGALVSITPQQSHAAFFTTVIIPAIVGGIATGAAVGTVSGLLGWG
LKQAEEANKTPDKPDKVWRIQAGKGFNEFPNKEYDLYRSLLSSKIDGGWDWGNAATHYWV
KGGGQWNKLEVDMKDAVGTYNLSGLRNFTGGDLDVNMQKATLRLGQFNGNSFTSYKDSAD
RTTRVDFNAKNILIDNFLEINNRVGSGAGRKASSTVLTLQASEGITSSKNAEISLYDGATLNLA
SNSVKLMGNVWMGRLQYVGAYLAPSYSTINTSKVTGEVNFNHLTVGDHNAAQAGIIASNKT
HIGTLDLWQSAGLNIIAPPEGGYKDKPKDKPSNTTQNNANNNQQNSAQNNSNTQVINPPNS
AQKTEIQPTQVIDGPFAGGKDTVVNIDRINTNADGTIKVGGYKASLTTNAAHLHIGKGGINLSN
QASGRTLLVENLTGNITVDGPLRVNNQVGGYALAGSSANFEFKAGTDTKNGTATFNNDISLG
RFVNLKVDAHTANFKGIDTGNGGFNTLDFSGVTGKVNINKLITASTNVAVKNFNINELVVKTN
GVSVGEYTHFSEDIGSQSRINTVRLETGTRSIFSGGVKFKSGEKLVIDEFYYSPWNYFDARNI
KNVEITRKFASSTPENPWGTSKLMFNNLTLGQNAVMDYSQFSNLTIQGDFINNQGTINYLVR
GGQVATLNVGNAAAMFFSNNVDSATGFYQPLMKINSAQDLIKNKEHVLLKAKIIGYGNVSLG
TNSISNVNLIEQFKERLALYNNNRMDICVVRNTDDIKACGTAIGNQSMVNNPDNYKYLIGKA
WKNIGISKTANGSKISVYYLGNSTPTEKGGNTTNLPTNTTSNVRSANNALAQNAPFAQPSAT
PNLVAINQHDFGTIESVFELANRSKDIDTLYANSGAQGRDLLQTLLIDSHDAGYARQMIDNTS
TGEITKQLNAATTTLNNIASLEHKTSSLQTLSLSNAMILNSRLVNLSRRHTNNIDSFAQRLQAL
KDQKFASLESAAEVLYQFAPKYEKPTNVWANAIGGTSLNNGGNASLYGTSAGVDAYLNGEV
EAIVGGFGSYGYSSFNNQANSLNSGANNTNFGVYSRIFANQHEFDFEAQGALGSDQSSLNF
KSALLRDLNQSYNYLAYSAATRASYGYDFAFFRNALVLKPSVGVSYNHLGSTNFKSNSNQV
ALKNGSSSQHLFNASANVEARYYYGDTSYFYMNAGVLQEFANFGSSNAVSLNTFKVNAAH
NPLSTHARVMMGGELKLAKEVFLNLGFVYLHNLISNIGHFASNLGMRYSF

F   **s1m1 VacA of strain *H. pylori* J99 (*Merrell et al., 2003, Infect Immun., 71(11):6510-25*) (SEQ ID NO: 6)**

MEIQQTHRKINRPLVSLVLAGALISAIPQESHAAFFTTVIIPAIVGGIATGTAVGTVSGLLSWGL
KQAEEANKTPDKPDKVWRIQAGKGFNEFPNKEYDLYKSLLSSKIDGGWDWGNAARHYWV
KGGGQWNKLEVDMKDAVGTYKLSGLRNFTGGDLDVNMQKATLRLGQFNGNSFTSYKDSAD
RTTRVNFNAKNISIDNFVEINNRVGSGAGRKASSTVLTLQASEGITSSKNAEISLYDGATLNL
ASNSVKLNGNVWMGRLQYVGAYLAPSYSTINTSKVQGEVDFNHLTVGDQNAAQAGIIASNK
THIGTLDLWQSAGLNIIAPPEGGYKDKPNSTTSQSGTKNDKKEISQNNNSNTEVINPPNNTQ
KTETEPTQVIDGPFAGGKDTVVNIFHLNTKADGTIKVGGFKASLTTNAAHLNIGKGGVNLSN
QASGRTLLVENLTGNITVDGPLRVNNQVGGYALAGSSANFEFKAGVDTKNGTATFNNDISL
GRFVNLKVDAHTANFKGIDTGNGGFNTLDFSGVTDKVNINKLITASTNVAVKNFNINELIVKT
NGISVGEYTHFSEDIGSQSRINTVRLETGTRSIFSGGVKFKSGEKLVINDFYYSPWNYFDAR
NVKNVEITRKFASSTPENPWGTSKLMFNNLTLGQNAVMDYSQFSNLTIQGDFINNQGTINYL
VRGGKVATLNVGNAAAMMFNNDIDSATGFYKPLIKINSAQDLIKNTEHVLLKAKIIGYGNVST
GTNGISNVNLEEQFKERLALYNNNRMDTCVVRNTDDIKACGMAIGNQSMVNNPDNYKYLI
GKAWRNIGISKTANGSKISVYYLGNSTPTENGGNTTNLPTNTTNNAHSANYALVKNAPFAHS
ATPNLVAINQHDFGTIESVFELANRSKDIDTLYTHSGAQGRDLLQTLLIDSHDAGYARQMIDN
TSTGEITKQLNAATDALNNVASLEHKQSGLQTLSLSNAMILNSRLVNLSRKHTNHINSFAQRL
QALKGQEFASLESAAEVLYQFAPKYEKPTNVWANAIGGASLNSGSNASLYGTSAGVDAFLN
GNVEAIVGGFGSYGYSSFSNQANSLNSGANNANFGVYSRFFANQHEFDFEAQGALGSDQS
SLNFKSTLLQDLNQSYNYLAYSATARASYGYDFAFFRNALVLKPSVGVSYNHLGSTNFKSN
SQSQVALKNGASSQHLFNANANVEARYYYGDTSYFYLHAGVLQEFAHFGSNDVASLNTFKI
NAARSPLSTYARAMMGGELQLAKEVFLNLGVVYLHNLISNASHFASNLGMRYSF

Figure 3 (continued)

G  s1m1 VacA from strain NCTC 11637 (*Ito et al., 1998, J. Infect. Dis., 178(5):1391-8*) (SEQ ID NO: 7)

MEIQQTHRKINRPLVSLALVGALVSITPQQSHAAFFTTVIIPAIVGGIATGAAVGTVSGLLSWG
LKQAEEANKTPDKPDKVWRIQAGRGFNNFPHKEYDLYKSLLSSKIDGGWDWGNAARHYW
VKGGQWNKLEVDMKDAVGTYKLSGLINFTGGDLDVNMQKATLRLGQFNGNSFTSYKDSA
DRTTRVDFNAKNILIDNFLEINNRVGSGAGRKASSTVLTLQASEGITSSKNAEISLYDGATLN
LASSSVKLMGNVWMGRLQYVGAYLAPSYSTINTSKVTGEVNFNHLTVGDHNAAQAGIIASN
KTHIGTLDLWQSAGLNIIAPPEGGYKDKPKDKPSNTTQNNANNNQQNSAQNNNNTQVINPP
NSAQKTEIQPTQVINGPFAGGKDTVVNINRINTNADGTIRVGGYKASLTTNAAHLHIGKGGIN
LSNQASGRSLLVENLTGNITVDGPLRVNNQVGGYALAGSNANFEFKAGTDTKNGTATFNN
DISLGRFVNLKVDAHTANFKGIDTGNGGFNTLDFSGVTDKVNINKLITASTNVAIKNFNINELL
VKTNGVSVGEYTHFSEDIGSQSRINTVRLETGTRSIFSGGVKFKSGEKLVIDEFYYSPWNYF
DARNIKNVEITRKFASSTPENPWGTSKLMFNNLTLGQNAVMDYSQFSNLTIQGDFINNQGTI
NYLVRGGKVATLNVGNAAAMMFNNDIDSATGFYKPLIKINSAQDLIKNTEHVLLKAKIIGYGN
VSTGTNGISNVNLEEQFKERLALYNNNNRMDTCVVRNTDDIKACGMAIGNQSMVNNPDNY
KYLIGKAWKNIGISKTANGSKISVYYLGNSTPTENGGNTTNLPTNTTNNARSANYALVKNAP
FAHSATPNLVAINQHDFGTIESVFELANRSKDIDTLYTHSGAKGRDLLQTLLIDSHDAGYARQ
MIDNTSTGEITKQLNAATTTLNNIASLEHKTSSLQTLSLSNAMILNSRLVNLSRKHTNNIDSFA
KRLQALKDQRFASLESAAEVLYQFAPKYEKPTNVWANAIGGASLNNGSNASLYGTSAGVD
AYLNGQVEAIVGGFGSYGYSSFSNRANSLNSGANNTNFGVYSRIFANQHEFDFEAQGALG
SDQSSLNFKSALLQDLNQSYNYLAYSAATRASYGYDFAFFKNALVLKPSVGVSYNHLGSTN
FKSNSTNKVALSNGSSSQHLFNASANVEARYYYGDTSYFYMNAGVLQEFANFGSSNAVSL
NTFKVNAARNPLNTHARVMMGGELQLAKEVFLNLGFVYLHNLISNIGHFASNLGMRYSF

H  s1m1 VacA of strain *H. pylori* P12 (*Fischer et al., 2010, Nucleic Acids Res. 38(18):6089-101*) (SEQ ID NO: 8)

MEIQQTHRKINRPLVSLALVGALVSITPQQSHAAFFTTVIIPAIVGGIASGAAVGTVSGLLGWGL
KQAEEANKTPDKPDKVWRIQAGKGFNEFPNKEYDLYRSLLSSKIDGGWDWGNAATHYWVK
GGQWNKLEVDMKDAVGTYNLSGLRNFTGGDLDVNMQKATLRLGQFNGNSFTSYKDSADRT
TRVDFNAKNISIDNFLEINNRVGSGAGRKASSTVLTLQASEGITSSKNAEISLYDGATLNLASSS
VKLMGNVWMGRLQYVGAYLAPSYSTINTSKVTGEVNFNHLTVGDRNAAQAGIIASNKTHIGTL
DLWQSAGLNIIAPPEGGYKDKPNNTPSQSGAKNDKNESAKNDKQESSQNNSNTQVINPPNS
AQKTEVQPTQVIDGPFAGGKDTVVNINRINTNADGTIRVGGYKASLTTNAAHLHIGKGGVNLS
NQASGRTLLVENLTGNITVDGPLRVNNQVGGYALAGSSANFEFKAGTDTKNGTATFNNDISL
GRFVNLKVDAHTANFKGIDTGNGGFNTLDFSGVTDKVNINKLITASTNVAIKNFNINELLVKTNG
VSVGEYTHFSEDIGSQSRINTVRLETGTRSIFSGGVKFKGGEKLVINDFYYAPWNYFDARNIKN
VEITNKLAFGPQGSPWGTSKLMFNNLTLGQNAVMDYSQFSNLTIQGDFVNNQGTINYLVRGG
QVATLNVGNAAAMFFNNNVDSATGFYQPLMKINSAQDLIKNKEHVLLKAKIIGYGNVSAGTNSI
SNVNLIEQFKERLALYEHNNRMDICVVRNTDDIKACGTAIGNQSMVNNPDNYKYLIGKAWKNI
GISKTANGSKISVHYLGNSTPTENSGNTTNLPTNTTSNARSAKNALAQNAPFAQPSATPSLVAI
NQHDFGTIESVFELANRSKDIDTLYTHSGAQGRNLLQTLLIDSHDAGYARQMIDNTSTGEIIKQL
NAATTTLNNVASLEHKQSGLQTLSLSNAMILNSRLVNLSRRHTNNIDSFAQRLQALKDQKFAS
LESAAEVLYQFAPKYEKPTNVWANAIGGTSLNNGGNASLYGTSAGVDAYLNGEVEAIVGGFG
SYGYSSFSNQANSLNSGANNTNFGVYSRLFANQHEFDFEAQGALGSDQSSLNFKSALLRDL
NQSYNYLAYSAATRASYGYDFAFFRNALVLKPSVGVSYNHLGSTNFKSNSTNQVALKNGSSS
QHLFNASANVEARYYYGDTSYFYMNAGVLQEFANFGSSNAVSLNTFKVNAARNPLNTHARV
MMGGELKLAKEVFLNLGFVYLHNLISNIGHFASNLGMRYSF

Figure 3 (continued)

I  **s1m1 VacA of strain *H. pylori* (Haas et al., 1994, Mol. Microbiol., 12:307-319) (SEQ ID NO: 9)**

MEIQQTHRKINRPLVSLALVGALVSITPQQSHAAFFTTVIIPAIVGGIATGAAVGTVSGLLGWGL
KQAEEANKTPDKPDKVWRIQAGKGFNEFPNKEYDLYKSLLSSKIDGGWDWGNAARHYWVK
DGQWNKLEVDMQNAVGTYNLSGLINFTGGDLDVNMQKATLRLGQFNGNSFTSYKDSADRT
TRVDFNAKNILIDNFLEINNRVGSGAGRKASSTVLTLQASEGITSRENAEISLYDGATLNLASN
SVKLMGNVWMGRLQYVGAYLAPSYSTINTSKVTGEVNFNHLTVGDHNAAQAGIIASNKTHIG
TLDLWQSAGLNIIAPPEGGYKDKPNDKPSNTTQNNAKNDKQESSQNNSNTQVINPPNSAQKT
EIQPTQVIDGPFAGGKNTVVNINRINTNADGTIRVGGFKASLTTNAAHLHIGKGGINLSNQASG
RSLLVENLTGNITVDGPLRVNNQVGGYALAGSSANFEFKAGTDTKNGTATFNNDISLGRFVN
LKVDAHTANFKGIDTGNGGFNTLDFSGVTNKVNINKLITASTNVAVKNFNINELVVKTNGVSVG
EYTHFSEDIGSQSRINTVRLETGTRSIYSGGVKFKGGEKLVINDFYYAPWNYFDARNIKNVEIT
NKLAFGPQGSPWGTAKLMFNNLTLGQNAVMDYSQFSNLTIQGDFVNNQGTINYLVRGGQVA
TLNVGNAAAMFFSNNVDSATGFYQPLMKINSAQDLIKNKEHVLLKAKIIGYGNVSAGTDSIANV
NLIEQFKERLALYNNNNRMDICVVRNTDDIKACGTAIGNQSMVNNPENYKYLEGKAWKNIGIS
KTANGSKISVHYLGNSTPTENGGNTTNLPTNTTNKVRFASYALIKNAPFARYSATPNLVAINQ
HDFGTIESVFELANRSNDIDTLYANSGAQGRDLLQTLLIDSHDAGYARTMIDATSANEITKQLN
TATTTLNNIASLEHKTSGLQTLSLSNAMILNSRLVNLSRRHTNHIDSFAKRLQALKDQRFASLE
SAAEVLYQFAPKYEKPTNVWANAIGGTSLNSGGNASLYGTSAGVDAYLNGEVEAIVGGFGSY
GYSSFSNQANSLNSGANNTNFGVYSRIFANQHEFDFEAQGALGSDQSSLNFKSALLRDLNQ
SYNYLAYSAATRASYGYDFAFFRNALVLKPSVGVSYNHLGSTNFKSNSNQKVALKNGASSQ
HLFNASANVEARYYYGDTSYFYMNAGVLQEFANFGSSNAVSLNTFKVNATRNPLNTHARVM
MGGELKLAKEVFLNLGFVYLHNLISNIGHFASNLGMRYSF

J  **s1m1 VacA of strain *H. pylori* NCTC 11638 (Phadnis et al., 1994, Infect. Immun. 62:1557-1565) (SEQ ID NO: 10)**

MEIQQTHRKINRPLVSLALVGALVSITPQQSHAAFFTTVIIPAIVGGIATGTAVGTVSGLLSWGLK
QAEEANKTPDKPDKVWRIQAGKGFNEFPNKEYDLYRSLLSSKIDGGWDWGNAARHYWVKG
GQQNKLEVDMKDAVGTYTLSGLRNFTGGDLDVNMQKATLRLGQFNGNSFTSYKDSADRTTR
VDFNAKNISIDNFVEINNRVGSGAGRKASSTVLTLQASEGITSDKNAEISLYDGATLNLASSS
VKLMGNVWMGRLQYVGAYLAPSYSTINTSKVTGEVNFNHLTVGDKNAAQAGIIANKKTNIGTL
DLWQSAGLNIIAPPEGGYKDKPNNTPSQSGAKNDKNESAKNDKQESSQNNSNTQVINPPNS
AQKTEVQPTQVIDGPFAGGKDTVVNINRINTNADGTIRVGGFKASLTTNAAHLHIGKGGVNLS
NQASGRSLIVENLTGNITVDGPLRVNNQVGGYALAGSSANFEFKAGTDTKNGTATFNNDISLG
RFVNLKVDAHTANFKGIDTGNGGFNTLDFSGVTDKVNINKLITASTNVAVKNFNINELIVKTNGI
SVGEYTHFSEDIGSQSRINTVRLETGTRSLFSGGVKFKGGEKLVIDEFYYSPWNYFDARNIKN
VEITNKLAFGPQGSPWGTSKLMFNNLTLGQNAVMDYSQFSNLTIQGDFINNQGTINYLVRGGK
VATLSVGNAAAMMFNNDIDSATGFYKPLIKINSAQDLIKNTEHVLLKAKIIGYGNVSTGTNGISN
VNLEEQFKERLALYNNNNRMDTCVVRNTDDIKACGMAIGDQSMVNNPDNYKYLIGKAWKNIG
ISKTANGSKISVYYLGNSTPTENGGNTTNLPTNTTSNARSANNALAQNAPFAQPSATPNLVAI
NQHDFGTIESVFELANRSKDIDTLYANSGAQGRDLLQTLLIDSHDAGYARKMIDATSANEITKQ
LNTATTTLNNIASLEHKTSGLQTLSLSNAMILNSRLVNLSRRHTNHIDSFAKRLQALKDQKFASL
ESAAEVLYQFAPKYEKPTNVWANAIGGTSLNNGSNASLYGTSAGVDAYLNGQVEAIVGGFGS
YGYSSFNNRANSLNSGANNTNFGVYSRIFANQHEFDFEAQGALGSDQSSLNFKSALLQDLNQ
SYHYLAYSAATRASYGYDFAFFRNALVLKPSVGVSYNHLGSTNFKSNSTNQVALKNGSSSQH
LFNASANVEARYYYGDTSYFYMNAGVLQEFAHVGSNNAASLNTFKVNAARNPLNTHARVMM
GGELKLAKEVFLNLGVVYLHNLISNIGHFASNLGMRYSFF

Figure 3 (continued)

SEQUENCE LISTING

```
<160> NUMBER OF SEQ ID NOS: 11

<210> SEQ ID NO 1
<211> LENGTH: 980
<212> TYPE: PRT
<213> ORGANISM: Helicobacter pylori strain ATCC 49503/60190

<400> SEQUENCE: 1

Ala Phe Phe Thr Thr Val Ile Ile Pro Ala Ile Val Gly Gly Ile Ala
1               5                   10                  15

Thr Gly Thr Ala Val Gly Thr Val Ser Gly Leu Leu Gly Trp Gly Leu
            20                  25                  30

Lys Gln Ala Glu Glu Ala Asn Lys Thr Pro Asp Lys Pro Asp Lys Val
        35                  40                  45

Trp Arg Ile Gln Ala Gly Lys Gly Phe Asn Glu Phe Pro Asn Lys Glu
    50                  55                  60

Tyr Asp Leu Tyr Lys Ser Leu Leu Ser Ser Lys Ile Asp Gly Gly Trp
65                  70                  75                  80

Asp Trp Gly Asn Ala Ala Thr His Tyr Trp Ile Lys Gly Gly Gln Trp
                85                  90                  95

Asn Lys Leu Glu Val Asp Met Lys Asp Ala Val Gly Thr Tyr Lys Leu
            100                 105                 110

Ser Gly Leu Arg Asn Phe Thr Gly Gly Asp Leu Asp Val Asn Met Gln
        115                 120                 125

Lys Ala Thr Leu Arg Leu Gly Gln Phe Asn Gly Asn Ser Phe Thr Ser
    130                 135                 140

Tyr Lys Asp Ser Ala Asp Arg Thr Thr Arg Val Asp Phe Asn Ala Lys
145                 150                 155                 160

Asn Ile Leu Ile Asp Asn Phe Leu Glu Ile Asn Asn Arg Val Gly Ser
                165                 170                 175

Gly Ala Gly Arg Lys Ala Ser Ser Thr Val Leu Thr Leu Gln Ala Ser
            180                 185                 190

Glu Gly Ile Thr Ser Ser Lys Asn Ala Glu Ile Ser Leu Tyr Asp Gly
        195                 200                 205

Ala Thr Leu Asn Leu Ala Ser Asn Ser Val Lys Leu Asn Gly Asn Val
    210                 215                 220
```

-continued

```
Trp Met Gly Arg Leu Gln Tyr Val Gly Ala Tyr Leu Ala Pro Ser Tyr
225                 230                 235                 240

Ser Thr Ile Asn Thr Ser Lys Val Thr Gly Glu Val Asn Phe Asn His
            245                 250                 255

Leu Thr Val Gly Asp His Asn Ala Ala Gln Ala Gly Ile Ile Ala Ser
        260                 265                 270

Asn Lys Thr His Ile Gly Thr Leu Asp Leu Trp Gln Ser Ala Gly Leu
    275                 280                 285

Asn Ile Ile Ala Pro Pro Glu Gly Gly Tyr Lys Asp Lys Pro Asn Asn
290                 295                 300

Thr Pro Ser Gln Ser Gly Ala Lys Asn Asp Lys Gln Glu Ser Ser Gln
305                 310                 315                 320

Asn Asn Ser Asn Thr Gln Val Ile Asn Pro Pro Asn Ser Thr Gln Lys
            325                 330                 335

Thr Glu Val Gln Pro Thr Gln Val Ile Asp Gly Pro Phe Ala Gly Gly
        340                 345                 350

Lys Asp Thr Val Val Asn Ile Asp Arg Ile Asn Thr Lys Ala Asp Gly
    355                 360                 365

Thr Ile Lys Val Gly Gly Phe Lys Ala Ser Leu Thr Thr Asn Ala Ala
370                 375                 380

His Leu Asn Ile Gly Lys Gly Gly Val Asn Leu Ser Asn Gln Ala Ser
385                 390                 395                 400

Gly Arg Thr Leu Leu Val Glu Asn Leu Thr Gly Asn Ile Thr Val Asp
            405                 410                 415

Gly Pro Leu Arg Val Asn Asn Gln Val Gly Gly Tyr Ala Leu Ala Gly
        420                 425                 430

Ser Ser Ala Asn Phe Glu Phe Lys Ala Gly Val Asp Thr Lys Asn Gly
    435                 440                 445

Thr Ala Thr Phe Asn Asn Asp Ile Ser Leu Gly Arg Phe Val Asn Leu
450                 455                 460

Lys Val Asp Ala His Thr Ala Asn Phe Lys Gly Ile Asp Thr Gly Asn
465                 470                 475                 480

Gly Gly Phe Asn Thr Leu Asp Phe Ser Gly Val Thr Asn Lys Val Asn
            485                 490                 495

Ile Asn Lys Leu Ile Thr Ala Ser Thr Asn Val Ala Val Lys Asn Phe
        500                 505                 510

Asn Ile Asn Glu Leu Ile Val Lys Thr Asn Gly Val Ser Val Gly Glu
    515                 520                 525

Tyr Thr His Phe Ser Glu Asp Ile Gly Ser Gln Ser Arg Ile Asn Thr
530                 535                 540

Val Arg Leu Glu Thr Gly Thr Arg Ser Ile Phe Ser Gly Gly Val Lys
545                 550                 555                 560

Phe Lys Ser Gly Glu Lys Leu Val Ile Asp Glu Phe Tyr Tyr Ser Pro
            565                 570                 575

Trp Asn Tyr Phe Asp Ala Arg Asn Ile Lys Asn Val Glu Ile Thr Arg
        580                 585                 590

Lys Phe Ala Ser Ser Thr Pro Glu Asn Pro Trp Gly Thr Ser Lys Leu
    595                 600                 605

Met Phe Asn Asn Leu Thr Leu Gly Gln Asn Ala Val Met Asp Tyr Ser
610                 615                 620

Gln Phe Ser Asn Leu Thr Ile Gln Gly Asp Phe Ile Asn Asn Gln Gly
625                 630                 635                 640
```

```
Thr Ile Asn Tyr Leu Val Arg Gly Gly Lys Val Ala Thr Leu Asn Val
                645                 650                 655

Gly Asn Ala Ala Ala Met Met Phe Asn Asn Asp Ile Asp Ser Ala Thr
            660                 665                 670

Gly Phe Tyr Lys Pro Leu Ile Lys Ile Asn Ser Ala Gln Asp Leu Ile
            675                 680                 685

Lys Asn Thr Glu His Val Leu Leu Lys Ala Lys Ile Ile Gly Tyr Gly
        690                 695                 700

Asn Val Ser Thr Gly Thr Asn Gly Ile Ser Asn Val Asn Leu Glu Glu
705                 710                 715                 720

Gln Phe Lys Glu Arg Leu Ala Leu Tyr Asn Asn Asn Arg Met Asp
                725                 730                 735

Thr Cys Val Val Arg Asn Thr Asp Asp Ile Lys Ala Cys Gly Met Ala
                740                 745                 750

Ile Gly Asn Gln Ser Met Val Asn Asn Pro Asp Asn Tyr Lys Tyr Leu
            755                 760                 765

Ile Gly Lys Ala Trp Lys Asn Ile Gly Ile Ser Lys Thr Ala Asn Gly
        770                 775                 780

Ser Lys Ile Ser Val Tyr Tyr Leu Gly Asn Ser Thr Pro Thr Glu Asn
785                 790                 795                 800

Gly Gly Asn Thr Thr Asn Leu Pro Thr Asn Thr Thr Asn Asn Ala Arg
                805                 810                 815

Phe Ala Ser Tyr Ala Leu Ile Lys Asn Ala Pro Phe Ala His Ser Ala
                820                 825                 830

Thr Pro Asn Leu Val Ala Ile Asn Gln His Asp Phe Gly Thr Ile Glu
            835                 840                 845

Ser Val Phe Glu Leu Ala Asn Arg Ser Lys Asp Ile Asp Thr Leu Tyr
        850                 855                 860

Ala Asn Ser Gly Ala Gln Gly Arg Asp Leu Leu Gln Thr Leu Leu Ile
865                 870                 875                 880

Asp Ser His Asp Ala Gly Tyr Ala Arg Thr Met Ile Asp Ala Thr Ser
                885                 890                 895

Ala Asn Glu Ile Thr Lys Gln Leu Asn Thr Ala Thr Thr Thr Leu Asn
                900                 905                 910

Asn Ile Ala Ser Leu Glu His Lys Thr Ser Ser Leu Gln Thr Leu Ser
            915                 920                 925

Leu Ser Asn Ala Met Ile Leu Asn Ser Arg Leu Val Asn Leu Ser Arg
        930                 935                 940

Arg His Thr Asn Asn Ile Asp Ser Phe Ala Lys Arg Leu Gln Ala Leu
945                 950                 955                 960

Lys Asp Gln Arg Phe Ala Ser Leu Glu Ser Ala Ala Glu Val Leu Tyr
                965                 970                 975

Gln Phe Ala Pro
            980

<210> SEQ ID NO 2
<211> LENGTH: 1309
<212> TYPE: PRT
<213> ORGANISM: Helicobacter pylori strainTx30a

<400> SEQUENCE: 2

Met Glu Ile Gln Gln Thr His Arg Lys Ile Asn Arg Pro Ile Ile Ser
1               5                   10                  15

Leu Ala Leu Val Gly Val Leu Met Gly Thr Glu Leu Gly Ala Asn Thr
                20                  25                  30
```

```
Pro Asn Asp Pro Ile His Ser Glu Ser Arg Ala Phe Phe Thr Thr Val
        35                  40                  45
Ile Ile Pro Ala Ile Val Gly Gly Ile Ala Thr Gly Ala Ala Val Gly
50                  55                  60
Thr Val Ser Gly Leu Leu Ser Trp Gly Leu Lys Gln Ala Glu Gln Ala
65                  70                  75                  80
Asn Lys Ala Pro Asp Lys Pro Asp Lys Val Trp Arg Ile Gln Ala Gly
                85                  90                  95
Arg Gly Phe Asp Asn Phe Pro His Lys Gln Tyr Asp Leu Tyr Lys Ser
                100                 105                 110
Leu Leu Ser Ser Lys Ile Asp Gly Gly Trp Asp Trp Gly Asn Ala Ala
                115                 120                 125
Arg His Tyr Trp Val Lys Asp Gly Gln Trp Asn Lys Leu Glu Val Asp
                130                 135                 140
Met Gln Asn Ala Val Gly Thr Tyr Asn Leu Ser Gly Leu Ile Asn Phe
145                 150                 155                 160
Thr Gly Gly Asp Leu Asp Val Asn Met Gln Lys Ala Thr Leu Arg Leu
                165                 170                 175
Gly Gln Phe Asn Gly Asn Ser Phe Thr Ser Phe Lys Asp Gly Ala Asn
                180                 185                 190
Arg Thr Thr Arg Val Asn Phe Asp Ala Lys Asn Ile Leu Ile Asp Asn
                195                 200                 205
Phe Val Glu Ile Asn Asn Arg Val Gly Ser Gly Ala Gly Arg Lys Ala
210                 215                 220
Ser Ser Thr Val Leu Thr Leu Lys Ser Ser Lys Ile Thr Ser Arg
225                 230                 235                 240
Glu Asn Ala Glu Ile Ser Leu Tyr Asp Gly Ala Thr Leu Asn Leu Val
                245                 250                 255
Ser Ser Ser Asn Gln Ser Val Asp Leu Tyr Gly Lys Val Trp Met Gly
                260                 265                 270
Arg Leu Gln Tyr Val Gly Ala Tyr Leu Ala Pro Ser Tyr Ser Thr Ile
                275                 280                 285
Asp Thr Ser Lys Val Gln Gly Glu Met Asn Phe Arg His Leu Ala Val
                290                 295                 300
Gly Asp Gln Asn Ala Ala Gln Ala Gly Ile Ile Ala Asn Lys Lys Thr
305                 310                 315                 320
Asn Ile Gly Thr Leu Asp Leu Trp Gln Ser Ala Gly Leu Ser Ile Ile
                325                 330                 335
Thr Pro Pro Glu Gly Gly Tyr Glu Ser Lys Thr Lys Asp Asn Pro Gln
                340                 345                 350
Asn Asn Pro Lys Asn Asp Ala Gln Lys Thr Glu Ile Gln Pro Thr Gln
                355                 360                 365
Val Ile Asp Gly Pro Phe Ala Gly Gly Lys Asp Thr Val Val Asn Ile
                370                 375                 380
Phe His Leu Asn Thr Lys Ala Asp Gly Thr Leu Arg Ala Gly Gly Phe
385                 390                 395                 400
Lys Ala Ser Leu Ser Thr Asn Ala Ala His Leu His Ile Gly Glu Gly
                405                 410                 415
Gly Val Asn Leu Ser Asn Gln Ala Ser Gly Arg Thr Leu Leu Val Glu
                420                 425                 430
Asn Leu Thr Gly Asn Ile Thr Val Glu Gly Thr Leu Arg Val Asn Asn
                435                 440                 445
```

-continued

Gln Val Gly Gly Ala Ala Ile Ala Gly Ser Ser Ala Asn Phe Glu Phe
    450                 455                 460

Lys Ala Gly Glu Asp Thr Asn Ala Thr Ala Thr Phe Asn Asn Asp
465                 470                 475                 480

Ile His Leu Gly Lys Ala Val Asn Leu Arg Val Asp Ala His Thr Ala
                485                 490                 495

Asn Phe Asn Gly Asn Ile Tyr Leu Gly Lys Ser Thr Asn Leu Arg Val
                500                 505                 510

Asn Gly His Thr Ala His Phe Lys Asn Ile Asp Ala Thr Lys Ser Asp
                515                 520                 525

Asn Gly Leu Asn Thr Ser Thr Leu Asp Phe Ser Gly Val Thr Asp Lys
530                 535                 540

Val Asn Ile Asn Lys Leu Thr Thr Ala Ala Thr Asn Val Asn Ile Lys
545                 550                 555                 560

Asn Phe Asp Ile Lys Glu Leu Val Val Thr Thr Arg Val Gln Ser Phe
                565                 570                 575

Gly Gln Tyr Thr Ile Phe Gly Glu Asn Ile Gly Asp Lys Ser Arg Ile
                580                 585                 590

Gly Val Val Ser Leu Gln Thr Gly Tyr Ser Pro Ala Tyr Ser Gly Gly
                595                 600                 605

Val Thr Phe Lys Gly Gly Lys Lys Leu Val Ile Asp Glu Ile Tyr His
    610                 615                 620

Ala Pro Trp Asn Tyr Phe Asp Ala Arg Asn Val Thr Asp Val Glu Ile
625                 630                 635                 640

Asn Lys Arg Ile Leu Phe Gly Ala Pro Gly Asn Ile Ala Gly Lys Thr
                645                 650                 655

Gly Leu Met Phe Asn Asn Leu Thr Leu Asn Ser Asn Ala Ser Met Asp
                660                 665                 670

Tyr Gly Lys Asp Leu Asp Leu Thr Ile Gln Gly His Phe Thr Asn Asn
                675                 680                 685

Gln Gly Thr Met Asn Leu Phe Val Gln Asp Gly Arg Val Ala Thr Leu
                690                 695                 700

Asn Ala Gly His Gln Ala Ser Met Ile Phe Asn Asn Leu Val Asp Ser
705                 710                 715                 720

Thr Thr Gly Phe Tyr Lys Pro Leu Ile Lys Ile Asn Asn Ala Gln Asn
                725                 730                 735

Leu Thr Lys Asn Lys Glu His Val Leu Val Lys Ala Arg Asn Ile Asp
                740                 745                 750

Tyr Asn Leu Val Gly Val Gln Gly Ala Ser Tyr Asp Asn Ile Ser Ala
                755                 760                 765

Ser Asn Thr Asn Leu Gln Glu Gln Phe Lys Glu Arg Leu Ala Leu Tyr
770                 775                 780

Asn Asn Asn Asn Arg Met Asp Thr Cys Val Val Arg Lys Asp Asn Leu
785                 790                 795                 800

Asn Asp Ile Lys Ala Cys Gly Met Ala Ile Gly Asn Gln Ser Met Val
                805                 810                 815

Asn Asn Pro Glu Asn Tyr Lys Tyr Leu Glu Gly Lys Ala Trp Lys Asn
                820                 825                 830

Thr Gly Ile Asn Lys Thr Ala Asn Thr Thr Ile Ala Val Asn Leu
                835                 840                 845

Gly Asn Asn Ser Thr Pro Thr Asn Ser Thr Asp Thr Thr Asn Leu
850                 855                 860

Pro Thr Asn Thr Thr Asn Asn Ala Arg Phe Ala Ser Tyr Ala Leu Ile

-continued

```
            865                 870                 875                 880
Lys Asn Ala Pro Phe Ala His Ser Ala Thr Pro Asn Leu Val Ala Ile
                    885                 890                 895
Asn Gln His Asp Phe Gly Thr Ile Glu Ser Val Phe Glu Leu Ala Asn
                    900                 905                 910
Arg Ser Ser Asp Ile Asp Thr Leu Tyr Ala Asn Ser Gly Ala Gln Gly
                    915                 920                 925
Arg Asp Leu Leu Gln Thr Leu Leu Ile Asp Ser His Asp Ala Gly Tyr
                    930                 935                 940
Ala Arg Thr Met Ile Asp Ala Thr Ser Ala Asn Glu Ile Thr Gln Gln
945                 950                 955                 960
Leu Asn Ala Ala Thr Thr Thr Leu Asn Asn Ile Ala Ser Leu Glu His
                    965                 970                 975
Lys Thr Ser Gly Leu Gln Thr Leu Ser Leu Ser Asn Ala Met Ile Leu
                    980                 985                 990
Asn Ser Arg Leu Val Asn Leu Ser Arg Lys His Thr Asn His Ile Asp
                    995                1000                1005
Ser Phe Ala Lys Arg Leu Gln Ala Leu Lys Asp Gln Arg Phe Ala
            1010                1015                1020
Ser Leu Glu Ser Ala Ala Glu Val Leu Tyr Gln Phe Ala Pro Lys
            1025                1030                1035
Tyr Glu Lys Pro Thr Asn Val Trp Ala Asn Ala Ile Gly Gly Thr
            1040                1045                1050
Ser Leu Asn Asn Gly Ser Asn Ala Ser Leu Tyr Gly Thr Ser Ala
            1055                1060                1065
Gly Val Asp Ala Tyr Leu Asn Gly Glu Val Glu Ala Ile Val Gly
            1070                1075                1080
Gly Phe Gly Ser Tyr Gly Tyr Ser Ser Phe Ser Asn Gln Ala Asn
            1085                1090                1095
Ser Leu Asn Ser Gly Ala Asn Asn Thr Asn Phe Gly Val Tyr Ser
            1100                1105                1110
Arg Ile Phe Ala Asn Gln His Glu Phe Asp Phe Glu Ala Gln Gly
            1115                1120                1125
Ala Leu Gly Ser Asp Gln Ser Ser Leu Asn Phe Lys Ser Ala Leu
            1130                1135                1140
Leu Gln Asp Leu Asn Gln Ser Tyr His Tyr Leu Ala Tyr Ser Ala
            1145                1150                1155
Thr Thr Arg Ala Ser Tyr Gly Tyr Asp Phe Ala Phe Phe Arg Asn
            1160                1165                1170
Ala Leu Val Leu Lys Pro Ser Val Gly Val Ser Tyr Asn His Leu
            1175                1180                1185
Gly Ser Thr Asn Phe Lys Ser Asn Ser Asn Gln Val Ala Leu Ser
            1190                1195                1200
Asn Gly Ser Ser Ser Gln His Leu Phe Asn Ala Asn Ala Asn Val
            1205                1210                1215
Glu Ala Arg Tyr Tyr Tyr Gly Asp Thr Ser Tyr Phe Tyr Met Asn
            1220                1225                1230
Ala Gly Val Leu Gln Glu Phe Ala Arg Phe Gly Ser Asn Asn Ala
            1235                1240                1245
Val Ser Leu Asn Thr Phe Lys Val Asn Ala Thr Arg Asn Pro Leu
            1250                1255                1260
Asn Thr His Ala Arg Val Met Met Gly Gly Glu Leu Gln Leu Ala
            1265                1270                1275
```

```
Lys Glu  Val Phe Leu Asn  Leu Gly Val Val  Tyr Leu His Asn  Leu
    1280         1285             1290

Ile Ser  Asn Ala Ser His  Phe Ala Ser Asn  Leu Gly Met Arg  Tyr
    1295         1300             1305

Ser

<210> SEQ ID NO 3
<211> LENGTH: 957
<212> TYPE: PRT
<213> ORGANISM: Artificial sequence
<220> FEATURE:
<223> OTHER INFORMATION: Deletion variant  del 6-27 VacA

<400> SEQUENCE: 3

Ala Phe Phe Thr Thr Leu Gly Trp Gly Leu Lys Gln Ala Glu Ala
1               5                   10                  15

Asn Lys Thr Pro Asp Lys Pro Asp Lys Val Trp Arg Ile Gln Ala Gly
                20              25                  30

Lys Gly Phe Asn Glu Phe Pro Asn Lys Glu Tyr Asp Leu Tyr Lys Ser
            35                  40                  45

Leu Leu Ser Ser Lys Ile Asp Gly Gly Trp Asp Trp Gly Asn Ala Ala
50                  55                  60

Thr His Tyr Trp Ile Lys Gly Gly Gln Trp Asn Lys Leu Glu Val Asp
65              70                  75                  80

Met Lys Asp Ala Val Gly Thr Tyr Lys Leu Ser Gly Leu Arg Asn Phe
                85                  90                  95

Thr Gly Gly Asp Leu Asp Val Asn Met Gln Lys Ala Thr Leu Arg Leu
            100                 105                 110

Gly Gln Phe Asn Gly Asn Ser Phe Thr Ser Tyr Lys Asp Ser Ala Asp
        115                 120                 125

Arg Thr Thr Arg Val Asp Phe Asn Ala Lys Asn Ile Leu Ile Asp Asn
130                 135                 140

Phe Leu Glu Ile Asn Asn Arg Val Gly Ser Gly Ala Gly Arg Lys Ala
145                 150                 155                 160

Ser Ser Thr Val Leu Thr Leu Gln Ala Ser Glu Gly Ile Thr Ser Ser
                165                 170                 175

Lys Asn Ala Glu Ile Ser Leu Tyr Asp Gly Ala Thr Leu Asn Leu Ala
            180                 185                 190

Ser Asn Ser Val Lys Leu Asn Gly Asn Val Trp Met Gly Arg Leu Gln
        195                 200                 205

Tyr Val Gly Ala Tyr Leu Ala Pro Ser Tyr Ser Thr Ile Asn Thr Ser
210                 215                 220

Lys Val Thr Gly Glu Val Asn Phe Asn His Leu Thr Val Gly Asp His
225                 230                 235                 240

Asn Ala Ala Gln Ala Gly Ile Ile Ala Ser Asn Lys Thr His Ile Gly
                245                 250                 255

Thr Leu Asp Leu Trp Gln Ser Ala Gly Leu Asn Ile Ile Ala Pro Pro
            260                 265                 270

Glu Gly Gly Tyr Lys Asp Lys Pro Asn Asn Thr Pro Ser Gln Ser Gly
        275                 280                 285

Ala Lys Asn Asp Lys Gln Glu Ser Ser Gln Asn Asn Ser Asn Thr Gln
290                 295                 300

Val Ile Asn Pro Pro Asn Ser Thr Gln Lys Thr Glu Val Gln Pro Thr
305                 310                 315                 320
```

```
Gln Val Ile Asp Gly Pro Phe Ala Gly Gly Lys Asp Thr Val Val Asn
                325                 330                 335

Ile Asp Arg Ile Asn Thr Lys Ala Asp Gly Thr Ile Lys Val Gly Gly
            340                 345                 350

Phe Lys Ala Ser Leu Thr Thr Asn Ala Ala His Leu Asn Ile Gly Lys
        355                 360                 365

Gly Gly Val Asn Leu Ser Asn Gln Ala Ser Gly Arg Thr Leu Leu Val
    370                 375                 380

Glu Asn Leu Thr Gly Asn Ile Thr Val Asp Gly Pro Leu Arg Val Asn
385                 390                 395                 400

Asn Gln Val Gly Gly Tyr Ala Leu Ala Gly Ser Ser Ala Asn Phe Glu
                405                 410                 415

Phe Lys Ala Gly Val Asp Thr Lys Asn Gly Thr Ala Thr Phe Asn Asn
            420                 425                 430

Asp Ile Ser Leu Gly Arg Phe Val Asn Leu Lys Val Asp Ala His Thr
        435                 440                 445

Ala Asn Phe Lys Gly Ile Asp Thr Gly Asn Gly Phe Asn Thr Leu
    450                 455                 460

Asp Phe Ser Gly Val Thr Asn Lys Val Asn Ile Asn Lys Leu Ile Thr
465                 470                 475                 480

Ala Ser Thr Asn Val Ala Val Lys Asn Phe Asn Ile Asn Glu Leu Ile
                485                 490                 495

Val Lys Thr Asn Gly Val Ser Val Gly Glu Tyr Thr His Phe Ser Glu
            500                 505                 510

Asp Ile Gly Ser Gln Ser Arg Ile Asn Thr Val Arg Leu Glu Thr Gly
        515                 520                 525

Thr Arg Ser Ile Phe Ser Gly Gly Val Lys Phe Lys Ser Gly Glu Lys
    530                 535                 540

Leu Val Ile Asp Glu Phe Tyr Tyr Ser Pro Trp Asn Tyr Phe Asp Ala
545                 550                 555                 560

Arg Asn Ile Lys Asn Val Glu Ile Thr Arg Lys Phe Ala Ser Ser Thr
                565                 570                 575

Pro Glu Asn Pro Trp Gly Thr Ser Lys Leu Met Phe Asn Asn Leu Thr
            580                 585                 590

Leu Gly Gln Asn Ala Val Met Asp Tyr Ser Gln Phe Ser Asn Leu Thr
        595                 600                 605

Ile Gln Gly Asp Phe Ile Asn Asn Gln Gly Thr Ile Asn Tyr Leu Val
    610                 615                 620

Arg Gly Gly Lys Val Ala Thr Leu Asn Val Gly Asn Ala Ala Ala Met
625                 630                 635                 640

Met Phe Asn Asn Asp Ile Asp Ser Ala Thr Gly Phe Tyr Lys Pro Leu
                645                 650                 655

Ile Lys Ile Asn Ser Ala Gln Asp Leu Ile Lys Asn Thr Glu His Val
            660                 665                 670

Leu Leu Lys Ala Lys Ile Ile Gly Tyr Gly Asn Val Ser Thr Gly Thr
        675                 680                 685

Asn Gly Ile Ser Asn Val Asn Leu Glu Glu Gln Phe Lys Glu Arg Leu
    690                 695                 700

Ala Leu Tyr Asn Asn Asn Asn Arg Met Asp Thr Cys Val Val Arg Asn
705                 710                 715                 720

Thr Asp Asp Ile Lys Ala Cys Gly Met Ala Ile Gly Asn Gln Ser Met
                725                 730                 735

Val Asn Asn Pro Asp Asn Tyr Lys Tyr Leu Ile Gly Lys Ala Trp Lys
```

```
                740                 745                 750
Asn Ile Gly Ile Ser Lys Thr Ala Asn Gly Ser Lys Ile Ser Val Tyr
            755                 760                 765

Tyr Leu Gly Asn Ser Thr Pro Thr Glu Asn Gly Gly Asn Thr Thr Asn
        770                 775                 780

Leu Pro Thr Asn Thr Thr Asn Asn Ala Arg Phe Ala Ser Tyr Ala Leu
785                 790                 795                 800

Ile Lys Asn Ala Pro Phe Ala His Ser Ala Thr Pro Asn Leu Val Ala
                805                 810                 815

Ile Asn Gln His Asp Phe Gly Thr Ile Glu Ser Val Phe Glu Leu Ala
            820                 825                 830

Asn Arg Ser Lys Asp Ile Asp Thr Leu Tyr Ala Asn Ser Gly Ala Gln
        835                 840                 845

Gly Arg Asp Leu Leu Gln Thr Leu Leu Ile Asp Ser His Asp Ala Gly
850                 855                 860

Tyr Ala Arg Thr Met Ile Asp Ala Thr Ser Ala Asn Glu Ile Thr Lys
865                 870                 875                 880

Gln Leu Asn Thr Ala Thr Thr Leu Asn Asn Ile Ala Ser Leu Glu
            885                 890                 895

His Lys Thr Ser Ser Leu Gln Thr Leu Ser Leu Ser Asn Ala Met Ile
                900                 905                 910

Leu Asn Ser Arg Leu Val Asn Leu Ser Arg Arg His Thr Asn Asn Ile
            915                 920                 925

Asp Ser Phe Ala Lys Arg Leu Gln Ala Leu Lys Asp Gln Arg Phe Ala
        930                 935                 940

Ser Leu Glu Ser Ala Ala Glu Val Leu Tyr Gln Phe Ala
945                 950                 955

<210> SEQ ID NO 4
<211> LENGTH: 1293
<212> TYPE: PRT
<213> ORGANISM: Helicobacter pylori strain G27

<400> SEQUENCE: 4

Met Glu Ile Gln Gln Thr His Arg Lys Met Asn Arg Pro Leu Val Ser
1               5                   10                  15

Leu Val Leu Ala Gly Ala Leu Ile Ser Ala Ile Pro Gln Glu Ser His
            20                  25                  30

Ala Ala Phe Phe Thr Thr Val Ile Ile Pro Ala Ile Val Gly Gly Ile
        35                  40                  45

Ala Thr Gly Thr Ala Val Gly Thr Val Ser Gly Leu Leu Ser Trp Gly
    50                  55                  60

Leu Lys Gln Ala Glu Glu Ala Asn Lys Asn Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Lys Ser Leu Leu Ser Ser Lys Ile Asp Gly Gly
            100                 105                 110

Trp Asp Trp Gly Asn Ala Ala Arg His Tyr Trp Val Lys Gly Gly Gln
        115                 120                 125

Trp Asn Lys Leu Glu Val Asp Met Lys Asp Ala Val Gly Thr Tyr Lys
    130                 135                 140

Leu Ser Gly Leu Arg Asn Phe Thr Gly Gly Asp Leu Asp Val Asn Met
145                 150                 155                 160
```

-continued

```
Gln Lys Ala Thr Leu Arg Leu Gly Gln Phe Asn Gly Asn Ser Phe Thr
                165                 170                 175
Ser Tyr Lys Asp Ala Ala Asp Arg Thr Thr Arg Val Asn Phe Asn Ala
            180                 185                 190
Lys Asn Ile Ser Ile Asp Asn Phe Val Glu Ile Asn Asn Arg Val Gly
        195                 200                 205
Ser Gly Ala Gly Arg Lys Ala Ser Ser Thr Val Leu Thr Leu Gln Ala
    210                 215                 220
Ser Glu Gly Ile Thr Ser Asp Lys Asn Ala Glu Ile Ser Leu Tyr Asp
225                 230                 235                 240
Gly Ala Thr Leu Asn Leu Ala Ser Ser Val Lys Leu Met Gly Asn
                245                 250                 255
Val Trp Met Gly Arg Leu Gln Tyr Val Gly Ala Tyr Leu Ala Pro Ser
            260                 265                 270
Tyr Ser Thr Ile Asn Thr Ser Lys Val Thr Gly Glu Val Asn Phe Asn
        275                 280                 285
His Leu Thr Val Gly Asp Lys Asn Ala Ala Gln Ala Gly Ile Ile Ala
    290                 295                 300
Ser Asn Lys Thr His Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Asn
                325                 330                 335
Asn Thr Pro Ser Gln Ser Gly Thr Lys Asn Asp Lys Asn Glu Ser Ala
            340                 345                 350
Lys Asn Asp Lys Gln Glu Ser Ser Gln Asn Asn Ser Asn Thr Gln Val
        355                 360                 365
Ile Asn Pro Pro Asn Ser Thr Gln Lys Thr Glu Ile Gln Pro Thr Gln
    370                 375                 380
Val Ile Asp Gly Pro Phe Ala Gly Gly Lys Asp Thr Val Val Asn Ile
385                 390                 395                 400
Asn Arg Ile Asn Thr Asn Ala Asp Gly Thr Ile Arg Val Gly Gly Phe
                405                 410                 415
Lys Ala Ser Leu Thr Thr Asn Ala Ala His Leu His Ile Gly Lys Gly
            420                 425                 430
Gly Val Asn Leu Ser Asn Gln Ala Ser Gly Arg Thr Leu Leu Val Glu
        435                 440                 445
Asn Leu Thr Gly Asn Ile Thr Val Asp Gly Pro Leu Arg Val Asn Asn
    450                 455                 460
Gln Val Gly Gly Tyr Ala Leu Ala Gly Ser Ser Ala Asn Phe Glu Phe
465                 470                 475                 480
Lys Ala Gly Val Asp Thr Lys Asn Gly Thr Ala Thr Phe Asn Asn Asp
                485                 490                 495
Ile Ser Leu Gly Arg Phe Val Asn Leu Lys Val Asp Ala His Thr Ala
            500                 505                 510
Asn Phe Lys Gly Ile Asp Thr Gly Asn Gly Phe Asn Thr Leu Asp
        515                 520                 525
Phe Ser Gly Val Thr Asp Lys Val Asn Ile Asn Lys Leu Ile Thr Ala
    530                 535                 540
Ser Thr Asn Val Ala Val Lys Asn Phe Asn Ile Asn Glu Leu Ile Val
545                 550                 555                 560
Lys Thr Asn Gly Ile Ser Val Gly Glu Tyr Thr His Phe Ser Glu Asp
                565                 570                 575
Ile Gly Ser Gln Ser Arg Ile Asn Thr Val Arg Leu Glu Thr Gly Thr
```

```
                580             585            590
Arg Ser Ile Phe Ser Gly Gly Val Lys Phe Lys Ser Gly Glu Lys Leu
            595             600             605
Val Ile Asp Glu Phe Tyr Tyr Ser Pro Trp Asn Tyr Phe Asp Ala Arg
            610             615             620
Asn Val Lys Asn Val Glu Ile Thr Arg Lys Phe Ala Ser Ser Thr Pro
625             630             635             640
Glu Asn Pro Trp Gly Thr Ser Lys Leu Met Phe Asn Asn Leu Thr Leu
                645             650             655
Gly Gln Asn Ala Val Met Asp Tyr Ser Gln Phe Ser Asn Leu Thr Ile
                660             665             670
Gln Gly Asp Phe Ile Asn Asn Gln Gly Thr Ile Asn Tyr Leu Val Arg
            675             680             685
Gly Gly Lys Val Ala Thr Leu Ser Val Gly Asn Ala Ala Ala Met Met
            690             695             700
Phe Asn Asn Asp Ile Asp Ser Ala Thr Gly Phe Tyr Lys Pro Leu Ile
705             710             715             720
Lys Ile Asn Ser Ala Gln Asp Leu Ile Lys Asn Thr Glu His Val Leu
                725             730             735
Leu Lys Ala Lys Ile Ile Gly Tyr Gly Asn Val Ser Thr Gly Thr Asn
                740             745             750
Ser Ile Ser Asn Val Asn Leu Glu Glu Gln Phe Lys Glu Arg Leu Ala
                755             760             765
Leu Tyr Asn Asn Asn Asn Arg Met Asp Thr Cys Val Val Arg Asn Thr
            770             775             780
Asp Asp Ile Lys Ala Cys Gly Met Ala Ile Gly Asn Gln Ser Met Val
785             790             795             800
Asn Asn Pro Asp Asn Tyr Lys Tyr Leu Ile Gly Lys Ala Trp Lys Asn
                805             810             815
Ile Gly Ile Ser Lys Thr Ala Asn Gly Ser Lys Ile Ser Val Tyr Tyr
                820             825             830
Leu Gly Asn Ser Thr Pro Thr Glu Asn Gly Gly Asn Thr Thr Asn Leu
            835             840             845
Pro Thr Asn Thr Thr Asn Asn Ala Arg Ser Ala Asn Tyr Ala Leu Val
850             855             860
Lys Asn Ala Pro Phe Ala His Ser Ala Thr Pro Asn Leu Val Ala Ile
865             870             875             880
Asn Gln His Asp Phe Gly Thr Ile Glu Ser Val Phe Glu Leu Ala Asn
                885             890             895
Arg Ser Lys Asp Ile Asp Thr Leu Tyr Thr His Ser Gly Val Gln Gly
            900             905             910
Arg Asp Leu Leu Gln Thr Leu Leu Ile Asp Ser His Asp Ala Gly Tyr
            915             920             925
Ala Arg Gln Met Ile Asp Asn Thr Ser Thr Gly Glu Ile Thr Lys Gln
            930             935             940
Leu Asn Ala Ala Thr Asp Ala Leu Asn Asn Ile Ala Ser Leu Glu His
945             950             955             960
Lys Thr Ser Gly Leu Gln Thr Leu Ser Leu Ser Asn Ala Met Ile Leu
                965             970             975
Asn Ser Arg Leu Val Asn Leu Ser Arg Lys His Thr Asn His Ile Asp
                980             985             990
Ser Phe Ala Gln Arg Leu Gln Ala  Leu Lys Gly Gln Arg  Phe Ala Ser
            995             1000            1005
```

```
Leu Glu Ser Ala Ala Glu Val Leu Tyr Gln Phe Ala Pro Lys Tyr
    1010                1015                1020

Glu Lys Pro Thr Asn Val Trp Ala Asn Ala Ile Gly Gly Ala Ser
    1025                1030                1035

Leu Asn Asn Gly Gly Asn Ala Ser Leu Tyr Gly Thr Ser Ala Gly
    1040                1045                1050

Val Asp Ala Tyr Leu Asn Gly Glu Val Glu Ala Ile Val Gly Gly
    1055                1060                1065

Phe Gly Ser Tyr Gly Tyr Ser Ser Phe Ser Asn Arg Ala Asn Ser
    1070                1075                1080

Leu Asn Ser Gly Ala Asn Asn Ala Asn Phe Gly Val Tyr Ser Arg
    1085                1090                1095

Ile Phe Ala Asn Gln His Glu Phe Asp Phe Glu Ala Gln Gly Ala
    1100                1105                1110

Leu Gly Ser Asp Gln Ser Ser Leu Asn Phe Lys Ser Ala Leu Leu
    1115                1120                1125

Gln Asp Leu Asn Gln Ser Tyr His Tyr Leu Ala Tyr Ser Ala Ala
    1130                1135                1140

Thr Arg Ala Ser Tyr Gly Tyr Asp Phe Ala Phe Arg Asn Ala
    1145                1150                1155

Leu Val Leu Lys Pro Ser Val Gly Val Ser Tyr Asn His Leu Gly
    1160                1165                1170

Ser Thr Asn Phe Lys Ser Ser Asn Gln Val Ala Leu Lys Asn
    1175                1180                1185

Gly Ser Ser Ser Gln His Leu Phe Asn Ala Asn Ala Asn Val Glu
    1190                1195                1200

Ala Arg Tyr Tyr Tyr Gly Asp Thr Ser Tyr Phe Tyr Met Asn Ala
    1205                1210                1215

Gly Val Leu Gln Glu Phe Ala Arg Phe Gly Ser Asn Asn Ala Ala
    1220                1225                1230

Ser Leu Asn Thr Phe Lys Val Asn Thr Ala Arg Asn Pro Leu Asn
    1235                1240                1245

Thr His Ala Arg Val Met Met Gly Gly Glu Leu Gln Leu Ala Lys
    1250                1255                1260

Glu Val Phe Leu Asn Leu Gly Val Val Tyr Leu His Asn Leu Ile
    1265                1270                1275

Ser Asn Ile Gly His Phe Ala Ser Asn Leu Gly Met Arg Tyr Ser
    1280                1285                1290

<210> SEQ ID NO 5
<211> LENGTH: 1287
<212> TYPE: PRT
<213> ORGANISM: Helicobacter pylori strain 60190

<400> SEQUENCE: 5

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
                20                  25                  30

Ala Ala Phe Phe Thr Thr Val Ile Ile Pro Ala Ile Val Gly Gly Ile
                35                  40                  45

Ala Thr Gly Thr Ala Val Gly Thr Val Ser Gly Leu Leu Gly Trp Gly
        50                  55                  60

Leu Lys Gln Ala Glu Glu Ala Asn Lys Thr Pro Asp Lys Pro Asp Lys
```

```
                65                  70                  75                  80
Val Trp Arg Ile Gln Ala Gly Lys Gly Phe Asn Glu Phe Pro Asn Lys
                        85                  90                  95
Glu Tyr Asp Leu Tyr Lys Ser Leu Leu Ser Lys Ile Asp Gly Gly
                    100                 105                 110
Trp Asp Trp Gly Asn Ala Ala Thr His Tyr Trp Ile Lys Gly Gly Gln
                115                 120                 125
Trp Asn Lys Leu Glu Val Asp Met Lys Asp Ala Val Gly Thr Tyr Lys
130                 135                 140
Leu Ser Gly Leu Arg Asn Phe Thr Gly Asp Leu Asp Val Asn Met
145                 150                 155                 160
Gln Lys Ala Thr Leu Arg Leu Gly Gln Phe Asn Gly Asn Ser Phe Thr
                    165                 170                 175
Ser Tyr Lys Asp Ser Ala Asp Arg Thr Thr Arg Val Asp Phe Asn Ala
                180                 185                 190
Lys Asn Ile Leu Ile Asp Asn Phe Leu Glu Ile Asn Asn Arg Val Gly
                195                 200                 205
Ser Gly Ala Gly Arg Lys Ala Ser Ser Thr Val Leu Thr Leu Gln Ala
    210                 215                 220
Ser Glu Gly Ile Thr Ser Ser Lys Asn Ala Glu Ile Ser Leu Tyr Asp
225                 230                 235                 240
Gly Ala Thr Leu Asn Leu Ala Ser Asn Ser Val Lys Leu Asn Gly Asn
                    245                 250                 255
Val Trp Met Gly Arg Leu Gln Tyr Val Gly Ala Tyr Leu Ala Pro Ser
                260                 265                 270
Tyr Ser Thr Ile Asn Thr Ser Lys Val Thr Gly Glu Val Asn Phe Asn
                275                 280                 285
His Leu Thr Val Gly Asp His Asn Ala Ala Gln Ala Gly Ile Ile Ala
                290                 295                 300
Ser Asn Lys Thr His Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Asn
                    325                 330                 335
Asn Thr Pro Ser Gln Ser Gly Ala Lys Asn Asp Lys Gln Glu Ser Ser
                340                 345                 350
Gln Asn Asn Ser Asn Thr Gln Val Ile Asn Pro Pro Asn Ser Thr Gln
                355                 360                 365
Lys Thr Glu Val Gln Pro Thr Gln Val Ile Asp Gly Pro Phe Ala Gly
    370                 375                 380
Gly Lys Asp Thr Val Val Asn Ile Asp Arg Ile Asn Thr Lys Ala Asp
385                 390                 395                 400
Gly Thr Ile Lys Val Gly Gly Phe Lys Ala Ser Leu Thr Asn Ala
                    405                 410                 415
Ala His Leu Asn Ile Gly Lys Gly Gly Val Asn Leu Ser Asn Gln Ala
                420                 425                 430
Ser Gly Arg Thr Leu Leu Val Glu Asn Leu Thr Gly Asn Ile Thr Val
                435                 440                 445
Asp Gly Pro Leu Arg Val Asn Asn Gln Val Gly Gly Tyr Ala Leu Ala
    450                 455                 460
Gly Ser Ser Ala Asn Phe Glu Phe Lys Ala Gly Val Asp Thr Lys Asn
465                 470                 475                 480
Gly Thr Ala Thr Phe Asn Asn Asp Ile Ser Leu Gly Arg Phe Val Asn
                    485                 490                 495
```

-continued

Leu Lys Val Asp Ala His Thr Ala Asn Phe Lys Gly Ile Asp Thr Gly
            500                 505                 510

Asn Gly Gly Phe Asn Thr Leu Asp Phe Ser Gly Val Thr Asn Lys Val
        515                 520                 525

Asn Ile Asn Lys Leu Ile Thr Ala Ser Thr Asn Val Ala Val Lys Asn
    530                 535                 540

Phe Asn Ile Asn Glu Leu Ile Val Lys Thr Asn Gly Val Ser Val Gly
545                 550                 555                 560

Glu Tyr Thr His Phe Ser Glu Asp Ile Gly Ser Gln Ser Arg Ile Asn
                565                 570                 575

Thr Val Arg Leu Glu Thr Gly Thr Arg Ser Ile Phe Ser Gly Gly Val
            580                 585                 590

Lys Phe Lys Ser Gly Glu Lys Leu Val Ile Asp Glu Phe Tyr Tyr Ser
        595                 600                 605

Pro Trp Asn Tyr Phe Asp Ala Arg Asn Ile Lys Asn Val Glu Ile Thr
    610                 615                 620

Arg Lys Phe Ala Ser Ser Thr Pro Glu Asn Pro Trp Gly Thr Ser Lys
625                 630                 635                 640

Leu Met Phe Asn Asn Leu Thr Leu Gly Gln Asn Ala Val Met Asp Tyr
                645                 650                 655

Ser Gln Phe Ser Asn Leu Thr Ile Gln Gly Asp Phe Ile Asn Asn Gln
            660                 665                 670

Gly Thr Ile Asn Tyr Leu Val Arg Gly Gly Lys Val Ala Thr Leu Asn
        675                 680                 685

Val Gly Asn Ala Ala Met Met Phe Asn Asn Asp Ile Asp Ser Ala
        690                 695                 700

Thr Gly Phe Tyr Lys Pro Leu Ile Lys Ile Asn Ser Ala Gln Asp Leu
705                 710                 715                 720

Ile Lys Asn Thr Glu His Val Leu Leu Lys Ala Lys Ile Ile Gly Tyr
                725                 730                 735

Gly Asn Val Ser Thr Gly Thr Asn Gly Ile Ser Asn Val Asn Leu Glu
            740                 745                 750

Glu Gln Phe Lys Glu Arg Leu Ala Leu Tyr Asn Asn Asn Arg Met
        755                 760                 765

Asp Thr Cys Val Val Arg Asn Thr Asp Asp Ile Lys Ala Cys Gly Met
    770                 775                 780

Ala Ile Gly Asn Gln Ser Met Val Asn Asn Pro Asp Asn Tyr Lys Tyr
785                 790                 795                 800

Leu Ile Gly Lys Ala Trp Lys Asn Ile Gly Ile Ser Lys Thr Ala Asn
                805                 810                 815

Gly Ser Lys Ile Ser Val Tyr Tyr Leu Gly Asn Ser Thr Pro Thr Glu
            820                 825                 830

Asn Gly Gly Asn Thr Thr Asn Leu Pro Thr Asn Thr Thr Asn Asn Ala
        835                 840                 845

Arg Phe Ala Ser Tyr Ala Leu Ile Lys Asn Ala Pro Phe Ala His Ser
    850                 855                 860

Ala Thr Pro Asn Leu Val Ala Ile Asn Gln His Asp Phe Gly Thr Ile
865                 870                 875                 880

Glu Ser Val Phe Glu Leu Ala Asn Arg Ser Lys Asp Ile Asp Thr Leu
                885                 890                 895

Tyr Ala Asn Ser Gly Ala Gln Gly Arg Asp Leu Leu Gln Thr Leu Leu
            900                 905                 910

```
Ile Asp Ser His Asp Ala Gly Tyr Ala Arg Thr Met Ile Asp Ala Thr
    915                 920                 925

Ser Ala Asn Glu Ile Thr Lys Gln Leu Asn Thr Ala Thr Thr Thr Leu
    930                 935                 940

Asn Asn Ile Ala Ser Leu Glu His Lys Thr Ser Ser Leu Gln Thr Leu
945                 950                 955                 960

Ser Leu Ser Asn Ala Met Ile Leu Asn Ser Arg Leu Val Asn Leu Ser
                965                 970                 975

Arg Arg His Thr Asn Asn Ile Asp Ser Phe Ala Lys Arg Leu Gln Ala
                980                 985                 990

Leu Lys Asp Gln Arg Phe Ala Ser Leu Glu Ser Ala Ala Glu Val Leu
    995                 1000                1005

Tyr Gln Phe Ala Pro Lys Tyr Glu Lys Pro Thr Asn Val Trp Ala
    1010                1015                1020

Asn Ala Ile Gly Gly Ala Ser Leu Asn Gly Gly Asn Ala Ser
    1025                1030                1035

Leu Tyr Gly Thr Ser Ala Gly Val Asp Ala Tyr Leu Asn Gly Gln
    1040                1045                1050

Val Glu Ala Ile Val Gly Gly Phe Gly Ser Tyr Gly Tyr Ser Ser
    1055                1060                1065

Phe Asn Asn Gln Ala Asn Ser Leu Asn Ser Gly Ala Asn Asn Thr
    1070                1075                1080

Asn Phe Gly Val Tyr Ser Arg Ile Phe Ala Asn Gln His Glu Phe
    1085                1090                1095

Asp Phe Glu Ala Gln Gly Ala Leu Gly Ser Asp Gln Ser Ser Leu
    1100                1105                1110

Asn Phe Lys Ser Ala Leu Leu Arg Asp Leu Asn Gln Ser Tyr Asn
    1115                1120                1125

Tyr Leu Ala Tyr Ser Ala Ala Thr Arg Ala Ser Tyr Gly Tyr Asp
    1130                1135                1140

Phe Ala Phe Phe Arg Asn Ala Leu Val Leu Lys Pro Ser Val Gly
    1145                1150                1155

Val Ser Tyr Asn His Leu Gly Ser Thr Asn Phe Lys Ser Asn Ser
    1160                1165                1170

Thr Asn Lys Val Ala Leu Ser Asn Gly Ser Ser Ser Gln His Leu
    1175                1180                1185

Phe Asn Ala Ser Ala Asn Val Glu Ala Arg Tyr Tyr Tyr Gly Asp
    1190                1195                1200

Thr Ser Tyr Phe Tyr Met Asn Ala Gly Val Leu Gln Glu Phe Ala
    1205                1210                1215

Asn Phe Gly Ser Ser Asn Ala Val Ser Leu Asn Thr Phe Lys Val
    1220                1225                1230

Asn Ala Thr Arg Asn Pro Leu Asn Thr His Ala Arg Val Met Met
    1235                1240                1245

Gly Gly Glu Leu Lys Leu Ala Lys Glu Val Phe Leu Asn Leu Gly
    1250                1255                1260

Val Val Tyr Leu His Asn Leu Ile Ser Asn Ile Gly His Phe Ala
    1265                1270                1275

Ser Asn Leu Gly Met Arg Tyr Ser Phe
    1280                1285

<210> SEQ ID NO 6
<211> LENGTH: 1290
<212> TYPE: PRT
```

-continued

<213> ORGANISM: Helicobacter pylori strain 26695

<400> SEQUENCE: 6

```
Met Glu Ile Gln Gln Thr His Arg Lys Ile Asn Arg Pro Leu Val Ser
1               5                   10                  15
Leu Ala Leu Val Gly Ala Leu Val Ser Ile Thr Pro Gln Gln Ser His
            20                  25                  30
Ala Ala Phe Phe Thr Thr Val Ile Ile Pro Ala Ile Val Gly Gly Ile
        35                  40                  45
Ala Thr Gly Ala Ala Val Gly Thr Val Ser Gly Leu Leu Gly Trp Gly
    50                  55                  60
Leu Lys Gln Ala Glu Glu Ala Asn Lys Thr Pro Asp Lys Pro Asp Lys
65                  70                  75                  80
Val Trp Arg Ile Gln Ala Gly Lys Gly Phe Asn Glu Phe Pro Asn Lys
                85                  90                  95
Glu Tyr Asp Leu Tyr Arg Ser Leu Leu Ser Ser Lys Ile Asp Gly Gly
            100                 105                 110
Trp Asp Trp Gly Asn Ala Ala Thr His Tyr Trp Val Lys Gly Gly Gln
        115                 120                 125
Trp Asn Lys Leu Glu Val Asp Met Lys Asp Ala Val Gly Thr Tyr Asn
    130                 135                 140
Leu Ser Gly Leu Arg Asn Phe Thr Gly Gly Asp Leu Asp Val Asn Met
145                 150                 155                 160
Gln Lys Ala Thr Leu Arg Leu Gly Gln Phe Asn Gly Asn Ser Phe Thr
                165                 170                 175
Ser Tyr Lys Asp Ser Ala Asp Arg Thr Thr Arg Val Asp Phe Asn Ala
            180                 185                 190
Lys Asn Ile Leu Ile Asp Asn Phe Leu Glu Ile Asn Asn Arg Val Gly
        195                 200                 205
Ser Gly Ala Gly Arg Lys Ala Ser Ser Thr Val Leu Thr Leu Gln Ala
    210                 215                 220
Ser Glu Gly Ile Thr Ser Ser Lys Asn Ala Glu Ile Ser Leu Tyr Asp
225                 230                 235                 240
Gly Ala Thr Leu Asn Leu Ala Ser Asn Ser Val Lys Leu Met Gly Asn
                245                 250                 255
Val Trp Met Gly Arg Leu Gln Tyr Val Gly Ala Tyr Leu Ala Pro Ser
            260                 265                 270
Tyr Ser Thr Ile Asn Thr Ser Lys Val Thr Gly Glu Val Asn Phe Asn
        275                 280                 285
His Leu Thr Val Gly Asp His Asn Ala Ala Gln Ala Gly Ile Ile Ala
    290                 295                 300
Ser Asn Lys Thr His Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Lys
                325                 330                 335
Asp Lys Pro Ser Asn Thr Thr Gln Asn Asn Ala Asn Asn Gln Gln
            340                 345                 350
Asn Ser Ala Gln Asn Asn Ser Asn Thr Gln Val Ile Asn Pro Pro Asn
        355                 360                 365
Ser Ala Gln Lys Thr Glu Ile Gln Pro Thr Gln Val Ile Asp Gly Pro
    370                 375                 380
Phe Ala Gly Gly Lys Asp Thr Val Val Asn Ile Asp Arg Ile Asn Thr
385                 390                 395                 400
```

```
Asn Ala Asp Gly Thr Ile Lys Val Gly Gly Tyr Lys Ala Ser Leu Thr
                    405                 410                 415
Thr Asn Ala Ala His Leu His Ile Gly Lys Gly Ile Asn Leu Ser
            420                 425                 430
Asn Gln Ala Ser Gly Arg Thr Leu Leu Val Glu Asn Leu Thr Gly Asn
        435                 440                 445
Ile Thr Val Asp Gly Pro Leu Arg Val Asn Asn Gln Val Gly Gly Tyr
    450                 455                 460
Ala Leu Ala Gly Ser Ser Ala Asn Phe Glu Phe Lys Ala Gly Thr Asp
465                 470                 475                 480
Thr Lys Asn Gly Thr Ala Thr Phe Asn Asn Asp Ile Ser Leu Gly Arg
                485                 490                 495
Phe Val Asn Leu Lys Val Asp Ala His Thr Ala Asn Phe Lys Gly Ile
            500                 505                 510
Asp Thr Gly Asn Gly Gly Phe Asn Thr Leu Asp Phe Ser Gly Val Thr
        515                 520                 525
Gly Lys Val Asn Ile Asn Lys Leu Ile Thr Ala Ser Thr Asn Val Ala
    530                 535                 540
Val Lys Asn Phe Asn Ile Asn Glu Leu Val Val Lys Thr Asn Gly Val
545                 550                 555                 560
Ser Val Gly Glu Tyr Thr His Phe Ser Glu Asp Ile Gly Ser Gln Ser
                565                 570                 575
Arg Ile Asn Thr Val Arg Leu Glu Thr Gly Thr Arg Ser Ile Phe Ser
            580                 585                 590
Gly Gly Val Lys Phe Lys Ser Gly Glu Lys Leu Val Ile Asp Glu Phe
        595                 600                 605
Tyr Tyr Ser Pro Trp Asn Tyr Phe Asp Ala Arg Asn Ile Lys Asn Val
    610                 615                 620
Glu Ile Thr Arg Lys Phe Ala Ser Ser Thr Pro Glu Asn Pro Trp Gly
625                 630                 635                 640
Thr Ser Lys Leu Met Phe Asn Asn Leu Thr Leu Gly Gln Asn Ala Val
                645                 650                 655
Met Asp Tyr Ser Gln Phe Ser Asn Leu Thr Ile Gln Gly Asp Phe Ile
            660                 665                 670
Asn Asn Gln Gly Thr Ile Asn Tyr Leu Val Arg Gly Gly Gln Val Ala
        675                 680                 685
Thr Leu Asn Val Gly Asn Ala Ala Met Phe Phe Ser Asn Asn Val
    690                 695                 700
Asp Ser Ala Thr Gly Phe Tyr Gln Pro Leu Met Lys Ile Asn Ser Ala
705                 710                 715                 720
Gln Asp Leu Ile Lys Asn Lys Glu His Val Leu Leu Lys Ala Lys Ile
                725                 730                 735
Ile Gly Tyr Gly Asn Val Ser Leu Gly Thr Asn Ser Ile Ser Asn Val
            740                 745                 750
Asn Leu Ile Glu Gln Phe Lys Glu Arg Leu Ala Leu Tyr Asn Asn Asn
        755                 760                 765
Asn Arg Met Asp Ile Cys Val Val Arg Asn Thr Asp Asp Ile Lys Ala
    770                 775                 780
Cys Gly Thr Ala Ile Gly Asn Gln Ser Met Val Asn Asn Pro Asp Asn
785                 790                 795                 800
Tyr Lys Tyr Leu Ile Gly Lys Ala Trp Lys Asn Ile Gly Ile Ser Lys
                805                 810                 815
Thr Ala Asn Gly Ser Lys Ile Ser Val Tyr Tyr Leu Gly Asn Ser Thr
```

```
                    820             825                 830
Pro Thr Glu Lys Gly Gly Asn Thr Thr Asn Leu Pro Thr Asn Thr Thr
            835                 840                 845
Ser Asn Val Arg Ser Ala Asn Asn Ala Leu Ala Gln Asn Ala Pro Phe
        850                 855                 860
Ala Gln Pro Ser Ala Thr Pro Asn Leu Val Ala Ile Asn Gln His Asp
865                 870                 875                 880
Phe Gly Thr Ile Glu Ser Val Phe Glu Leu Ala Asn Arg Ser Lys Asp
                885                 890                 895
Ile Asp Thr Leu Tyr Ala Asn Ser Gly Ala Gln Gly Arg Asp Leu Leu
            900                 905                 910
Gln Thr Leu Leu Ile Asp Ser His Asp Ala Gly Tyr Ala Arg Gln Met
        915                 920                 925
Ile Asp Asn Thr Ser Thr Gly Glu Ile Thr Lys Gln Leu Asn Ala Ala
    930                 935                 940
Thr Thr Thr Leu Asn Asn Ile Ala Ser Leu Glu His Lys Thr Ser Ser
945                 950                 955                 960
Leu Gln Thr Leu Ser Leu Ser Asn Ala Met Ile Leu Asn Ser Arg Leu
                965                 970                 975
Val Asn Leu Ser Arg Arg His Thr Asn Asn Ile Asp Ser Phe Ala Gln
            980                 985                 990
Arg Leu Gln Ala Leu Lys Asp Gln Lys Phe Ala Ser Leu Glu Ser Ala
        995                 1000                1005
Ala Glu Val Leu Tyr Gln Phe Ala Pro Lys Tyr Glu Lys Pro Thr
    1010                1015                1020
Asn Val Trp Ala Asn Ala Ile Gly Gly Thr Ser Leu Asn Asn Gly
    1025                1030                1035
Gly Asn Ala Ser Leu Tyr Gly Thr Ser Ala Gly Val Asp Ala Tyr
    1040                1045                1050
Leu Asn Gly Glu Val Glu Ala Ile Val Gly Gly Phe Gly Ser Tyr
    1055                1060                1065
Gly Tyr Ser Ser Phe Asn Asn Gln Ala Asn Ser Leu Asn Ser Gly
    1070                1075                1080
Ala Asn Asn Thr Asn Phe Gly Val Tyr Ser Arg Ile Phe Ala Asn
    1085                1090                1095
Gln His Glu Phe Asp Phe Glu Ala Gln Gly Ala Leu Gly Ser Asp
    1100                1105                1110
Gln Ser Ser Leu Asn Phe Lys Ser Ala Leu Leu Arg Asp Leu Asn
    1115                1120                1125
Gln Ser Tyr Asn Tyr Leu Ala Tyr Ser Ala Ala Thr Arg Ala Ser
    1130                1135                1140
Tyr Gly Tyr Asp Phe Ala Phe Phe Arg Asn Ala Leu Val Leu Lys
    1145                1150                1155
Pro Ser Val Gly Val Ser Tyr Asn His Leu Gly Ser Thr Asn Phe
    1160                1165                1170
Lys Ser Asn Ser Asn Gln Val Ala Leu Lys Asn Gly Ser Ser Ser
    1175                1180                1185
Gln His Leu Phe Asn Ala Ser Ala Asn Val Glu Ala Arg Tyr Tyr
    1190                1195                1200
Tyr Gly Asp Thr Ser Tyr Phe Tyr Met Asn Ala Gly Val Leu Gln
    1205                1210                1215
Glu Phe Ala Asn Phe Gly Ser Ser Asn Ala Val Ser Leu Asn Thr
    1220                1225                1230
```

-continued

Phe Lys Val Asn Ala Ala His Asn Pro Leu Ser Thr His Ala Arg
    1235                1240                1245

Val Met Met Gly Gly Glu Leu Lys Leu Ala Lys Glu Val Phe Leu
    1250                1255                1260

Asn Leu Gly Phe Val Tyr Leu His Asn Leu Ile Ser Asn Ile Gly
    1265                1270                1275

His Phe Ala Ser Asn Leu Gly Met Arg Tyr Ser Phe
    1280                1285                1290

<210> SEQ ID NO 7
<211> LENGTH: 1288
<212> TYPE: PRT
<213> ORGANISM: Helicobacter pylori strain J99

<400> SEQUENCE: 7

Met Glu Ile Gln Gln Thr His Arg Lys Ile Asn Arg Pro Leu Val Ser
1               5                   10                  15

Leu Val Leu Ala Gly Ala Leu Ile Ser Ala Ile Pro Gln Glu Ser His
            20                  25                  30

Ala Ala Phe Phe Thr Thr Val Ile Ile Pro Ala Ile Val Gly Gly Ile
        35                  40                  45

Ala Thr Gly Thr Ala Val Gly Thr Val Ser Gly Leu Leu Ser Trp Gly
    50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Lys Ser Leu Leu Ser Ser Lys Ile Asp Gly Gly
            100                 105                 110

Trp Asp Trp Gly Asn Ala Ala Arg His Tyr Trp Val Lys Gly Gly Gln
        115                 120                 125

Trp Asn Lys Leu Glu Val Asp Met Lys Asp Ala Val Gly Thr Tyr Lys
    130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asn Phe Asn Ala
            180                 185                 190

Lys Asn Ile Ser Ile Asp Asn Phe Val Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Ser Lys Asn Ala Glu Ile Ser Leu Tyr Asp
225                 230                 235                 240

Gly Ala Thr Leu Asn Leu Ala Ser Asn Ser Val Lys Leu Asn Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Gln Gly Glu Val Asp Phe Asn
        275                 280                 285

His Leu Thr Val Gly Asp Gln Asn Ala Ala Gln Ala Gly Ile Ile Ala
    290                 295                 300

Ser Asn Lys Thr His Ile Gly Thr Leu Asp Leu Trp Gln Ser Ala Gly

```
305                 310                 315                 320
Leu Asn Ile Ile Ala Pro Pro Glu Gly Gly Tyr Lys Asp Lys Pro Asn
            325                 330                 335
Ser Thr Thr Ser Gln Ser Gly Thr Lys Asn Asp Lys Lys Glu Ile Ser
            340                 345                 350
Gln Asn Asn Ser Asn Thr Glu Val Ile Asn Pro Pro Asn Asn Thr
            355                 360                 365
Gln Lys Thr Glu Thr Glu Pro Thr Gln Val Ile Asp Gly Pro Phe Ala
    370                 375                 380
Gly Gly Lys Asp Thr Val Val Asn Ile Phe His Leu Asn Thr Lys Ala
385                 390                 395                 400
Asp Gly Thr Ile Lys Val Gly Phe Lys Ala Ser Leu Thr Thr Asn
            405                 410                 415
Ala Ala His Leu Asn Ile Gly Lys Gly Val Asn Leu Ser Asn Gln
            420                 425                 430
Ala Ser Gly Arg Thr Leu Leu Val Glu Asn Leu Thr Gly Asn Ile Thr
        435                 440                 445
Val Asp Gly Pro Leu Arg Val Asn Asn Gln Val Gly Gly Tyr Ala Leu
    450                 455                 460
Ala Gly Ser Ser Ala Asn Phe Glu Phe Lys Ala Gly Val Asp Thr Lys
465                 470                 475                 480
Asn Gly Thr Ala Thr Phe Asn Asn Asp Ile Ser Leu Gly Arg Phe Val
            485                 490                 495
Asn Leu Lys Val Asp Ala His Thr Ala Asn Phe Lys Gly Ile Asp Thr
            500                 505                 510
Gly Asn Gly Gly Phe Asn Thr Leu Asp Phe Ser Gly Val Thr Asp Lys
            515                 520                 525
Val Asn Ile Asn Lys Leu Ile Thr Ala Ser Thr Asn Val Ala Val Lys
            530                 535                 540
Asn Phe Asn Ile Asn Glu Leu Ile Val Lys Thr Asn Gly Ile Ser Val
545                 550                 555                 560
Gly Glu Tyr Thr His Phe Ser Glu Asp Ile Gly Ser Gln Ser Arg Ile
            565                 570                 575
Asn Thr Val Arg Leu Glu Thr Gly Thr Arg Ser Ile Phe Ser Gly Gly
            580                 585                 590
Val Lys Phe Lys Ser Gly Glu Lys Leu Val Ile Asn Asp Phe Tyr Tyr
        595                 600                 605
Ser Pro Trp Asn Tyr Phe Asp Ala Arg Asn Val Lys Asn Val Glu Ile
    610                 615                 620
Thr Arg Lys Phe Ala Ser Ser Thr Pro Glu Asn Pro Trp Gly Thr Ser
625                 630                 635                 640
Lys Leu Met Phe Asn Asn Leu Thr Leu Gly Gln Asn Ala Val Met Asp
            645                 650                 655
Tyr Ser Gln Phe Ser Asn Leu Thr Ile Gln Gly Asp Phe Ile Asn Asn
            660                 665                 670
Gln Gly Thr Ile Asn Tyr Leu Val Arg Gly Gly Lys Val Ala Thr Leu
        675                 680                 685
Asn Val Gly Asn Ala Ala Ala Met Met Phe Asn Asn Asp Ile Asp Ser
    690                 695                 700
Ala Thr Gly Phe Tyr Lys Pro Leu Ile Lys Ile Asn Ser Ala Gln Asp
705                 710                 715                 720
Leu Ile Lys Asn Thr Glu His Val Leu Leu Lys Ala Lys Ile Ile Gly
            725                 730                 735
```

-continued

```
Tyr Gly Asn Val Ser Thr Gly Thr Asn Gly Ile Ser Asn Val Asn Leu
            740                 745                 750

Glu Glu Gln Phe Lys Glu Arg Leu Ala Leu Tyr Asn Asn Asn Asn Arg
            755                 760                 765

Met Asp Thr Cys Val Val Arg Asn Thr Asp Asp Ile Lys Ala Cys Gly
            770                 775                 780

Met Ala Ile Gly Asn Gln Ser Met Val Asn Asn Pro Asp Asn Tyr Lys
785                 790                 795                 800

Tyr Leu Ile Gly Lys Ala Trp Arg Asn Ile Gly Ile Ser Lys Thr Ala
            805                 810                 815

Asn Gly Ser Lys Ile Ser Val Tyr Tyr Leu Gly Asn Ser Thr Pro Thr
            820                 825                 830

Glu Asn Gly Gly Asn Thr Thr Asn Leu Pro Thr Asn Thr Thr Asn Asn
            835                 840                 845

Ala His Ser Ala Asn Tyr Ala Leu Val Lys Asn Ala Pro Phe Ala His
            850                 855                 860

Ser Ala Thr Pro Asn Leu Val Ala Ile Asn Gln His Asp Phe Gly Thr
865                 870                 875                 880

Ile Glu Ser Val Phe Glu Leu Ala Asn Arg Ser Lys Asp Ile Asp Thr
            885                 890                 895

Leu Tyr Thr His Ser Gly Ala Gln Gly Arg Asp Leu Leu Gln Thr Leu
            900                 905                 910

Leu Ile Asp Ser His Asp Ala Gly Tyr Ala Arg Gln Met Ile Asp Asn
            915                 920                 925

Thr Ser Thr Gly Glu Ile Thr Lys Gln Leu Asn Ala Ala Thr Asp Ala
            930                 935                 940

Leu Asn Asn Val Ala Ser Leu Glu His Lys Gln Ser Gly Leu Gln Thr
945                 950                 955                 960

Leu Ser Leu Ser Asn Ala Met Ile Leu Asn Ser Arg Leu Val Asn Leu
            965                 970                 975

Ser Arg Lys His Thr Asn His Ile Asn Ser Phe Ala Gln Arg Leu Gln
            980                 985                 990

Ala Leu Lys Gly Gln Glu Phe Ala Ser Leu Glu Ser Ala Ala Glu Val
            995                 1000                1005

Leu Tyr Gln Phe Ala Pro Lys Tyr Glu Lys Pro Thr Asn Val Trp
            1010                1015                1020

Ala Asn Ala Ile Gly Gly Ala Ser Leu Asn Ser Gly Ser Asn Ala
            1025                1030                1035

Ser Leu Tyr Gly Thr Ser Ala Gly Val Asp Ala Phe Leu Asn Gly
            1040                1045                1050

Asn Val Glu Ala Ile Val Gly Gly Phe Gly Ser Tyr Gly Tyr Ser
            1055                1060                1065

Ser Phe Ser Asn Gln Ala Asn Ser Leu Asn Ser Gly Ala Asn Asn
            1070                1075                1080

Ala Asn Phe Gly Val Tyr Ser Arg Phe Phe Ala Asn Gln His Glu
            1085                1090                1095

Phe Asp Phe Glu Ala Gln Gly Ala Leu Gly Ser Asp Gln Ser Ser
            1100                1105                1110

Leu Asn Phe Lys Ser Thr Leu Leu Gln Asp Leu Asn Gln Ser Tyr
            1115                1120                1125

Asn Tyr Leu Ala Tyr Ser Ala Thr Ala Arg Ala Ser Tyr Gly Tyr
            1130                1135                1140
```

-continued

```
Asp Phe Ala Phe Arg Asn Ala Leu Val Leu Lys Pro Ser Val
    1145                1150                1155

Gly Val Ser Tyr Asn His Leu Gly Ser Thr Asn Phe Lys Ser Asn
    1160                1165                1170

Ser Gln Ser Gln Val Ala Leu Lys Asn Gly Ala Ser Ser Gln His
    1175                1180                1185

Leu Phe Asn Ala Asn Ala Asn Val Glu Ala Arg Tyr Tyr Tyr Gly
    1190                1195                1200

Asp Thr Ser Tyr Phe Tyr Leu His Ala Gly Val Leu Gln Glu Phe
    1205                1210                1215

Ala His Phe Gly Ser Asn Asp Val Ala Ser Leu Asn Thr Phe Lys
    1220                1225                1230

Ile Asn Ala Ala Arg Ser Pro Leu Ser Thr Tyr Ala Arg Ala Met
    1235                1240                1245

Met Gly Gly Glu Leu Gln Leu Ala Lys Glu Val Phe Leu Asn Leu
    1250                1255                1260

Gly Val Val Tyr Leu His Asn Leu Ile Ser Asn Ala Ser His Phe
    1265                1270                1275

Ala Ser Asn Leu Gly Met Arg Tyr Ser Phe
    1280                1285

<210> SEQ ID NO 8
<211> LENGTH: 1290
<212> TYPE: PRT
<213> ORGANISM: Helicobacter pylori strain NCTC 11637

<400> SEQUENCE: 8

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
                20                  25                  30

Ala Ala Phe Phe Thr Thr Val Ile Ile Pro Ala Ile Val Gly Gly Ile
            35                  40                  45

Ala Thr Gly Ala Ala Val Gly Thr Val Ser Gly Leu Leu Ser Trp Gly
        50                  55                  60

Leu Lys Gln Ala Glu Glu Ala Asn Lys Thr Pro Asp Lys Pro Asp Lys
65                  70                  75                  80

Val Trp Arg Ile Gln Ala Gly Arg Gly Phe Asn Asn Phe Pro His Lys
                85                  90                  95

Glu Tyr Asp Leu Tyr Lys Ser Leu Leu Ser Ser Lys Ile Asp Gly Gly
                100                 105                 110

Trp Asp Trp Gly Asn Ala Ala Arg His Tyr Trp Val Lys Gly Gly Gln
            115                 120                 125

Trp Asn Lys Leu Glu Val Asp Met Lys Asp Ala Val Gly Thr Tyr Lys
        130                 135                 140

Leu Ser Gly Leu Ile Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
                180                 185                 190

Lys Asn Ile Leu Ile Asp Asn Phe Leu Glu Ile Asn Asn Arg Val Gly
            195                 200                 205

Ser Gly Ala Gly Arg Lys Ala Ser Ser Thr Val Leu Thr Leu Gln Ala
        210                 215                 220
```

-continued

Ser Glu Gly Ile Thr Ser Ser Lys Asn Ala Glu Ile Ser Leu Tyr Asp
225                 230                 235                 240

Gly Ala Thr Leu Asn Leu Ala Ser Ser Val Lys Leu Met Gly Asn
            245                 250                 255

Val Trp Met Gly Arg Leu Gln Tyr Val Gly Ala Tyr Leu Ala Pro Ser
        260                 265                 270

Tyr Ser Thr Ile Asn Thr Ser Lys Val Thr Gly Glu Val Asn Phe Asn
            275                 280                 285

His Leu Thr Val Gly Asp His Asn Ala Ala Gln Ala Gly Ile Ile Ala
        290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Lys
            325                 330                 335

Asp Lys Pro Ser Asn Thr Thr Gln Asn Asn Ala Asn Asn Gln Gln
        340                 345                 350

Asn Ser Ala Gln Asn Asn Asn Thr Gln Val Ile Asn Pro Pro Asn
            355                 360                 365

Ser Ala Gln Lys Thr Glu Ile Gln Pro Thr Gln Val Ile Asn Gly Pro
370                 375                 380

Phe Ala Gly Gly Lys Asp Thr Val Val Asn Ile Asn Arg Ile Asn Thr
385                 390                 395                 400

Asn Ala Asp Gly Thr Ile Arg Val Gly Gly Tyr Lys Ala Ser Leu Thr
            405                 410                 415

Thr Asn Ala Ala His Leu His Ile Gly Lys Gly Ile Asn Leu Ser
            420                 425                 430

Asn Gln Ala Ser Gly Arg Ser Leu Leu Val Glu Asn Leu Thr Gly Asn
            435                 440                 445

Ile Thr Val Asp Gly Pro Leu Arg Val Asn Asn Gln Val Gly Gly Tyr
450                 455                 460

Ala Leu Ala Gly Ser Asn Ala Asn Phe Glu Phe Lys Ala Gly Thr Asp
465                 470                 475                 480

Thr Lys Asn Gly Thr Ala Thr Phe Asn Asn Asp Ile Ser Leu Gly Arg
            485                 490                 495

Phe Val Asn Leu Lys Val Asp Ala His Thr Ala Asn Phe Lys Gly Ile
            500                 505                 510

Asp Thr Gly Asn Gly Phe Asn Thr Leu Asp Phe Ser Gly Val Thr
        515                 520                 525

Asp Lys Val Asn Ile Asn Lys Leu Ile Thr Ala Ser Thr Asn Val Ala
530                 535                 540

Ile Lys Asn Phe Asn Ile Asn Glu Leu Leu Val Lys Thr Asn Gly Val
545                 550                 555                 560

Ser Val Gly Glu Tyr Thr His Phe Ser Glu Asp Ile Gly Ser Gln Ser
            565                 570                 575

Arg Ile Asn Thr Val Arg Leu Glu Thr Gly Thr Arg Ser Ile Phe Ser
            580                 585                 590

Gly Gly Val Lys Phe Lys Ser Gly Glu Lys Leu Val Ile Asp Glu Phe
        595                 600                 605

Tyr Tyr Ser Pro Trp Asn Tyr Phe Asp Ala Arg Asn Ile Lys Asn Val
        610                 615                 620

Glu Ile Thr Arg Lys Phe Ala Ser Ser Thr Pro Glu Asn Pro Trp Gly
625                 630                 635                 640

```
Thr Ser Lys Leu Met Phe Asn Asn Leu Thr Leu Gly Gln Asn Ala Val
            645                 650                 655

Met Asp Tyr Ser Gln Phe Ser Asn Leu Thr Ile Gln Gly Asp Phe Ile
            660                 665                 670

Asn Asn Gln Gly Thr Ile Asn Tyr Leu Val Arg Gly Gly Lys Val Ala
            675                 680                 685

Thr Leu Asn Val Gly Asn Ala Ala Met Met Phe Asn Asn Asp Ile
    690                 695                 700

Asp Ser Ala Thr Gly Phe Tyr Lys Pro Leu Ile Lys Ile Asn Ser Ala
705                 710                 715                 720

Gln Asp Leu Ile Lys Asn Thr Glu His Val Leu Leu Lys Ala Lys Ile
                725                 730                 735

Ile Gly Tyr Gly Asn Val Ser Thr Gly Thr Asn Gly Ile Ser Asn Val
                740                 745                 750

Asn Leu Glu Glu Gln Phe Lys Glu Arg Leu Ala Leu Tyr Asn Asn Asn
            755                 760                 765

Asn Arg Met Asp Thr Cys Val Val Arg Asn Thr Asp Asp Ile Lys Ala
    770                 775                 780

Cys Gly Met Ala Ile Gly Asn Gln Ser Met Val Asn Asn Pro Asp Asn
785                 790                 795                 800

Tyr Lys Tyr Leu Ile Gly Lys Ala Trp Lys Asn Ile Gly Ile Ser Lys
                805                 810                 815

Thr Ala Asn Gly Ser Lys Ile Ser Val Tyr Tyr Leu Gly Asn Ser Thr
            820                 825                 830

Pro Thr Glu Asn Gly Gly Asn Thr Thr Asn Leu Pro Thr Asn Thr Thr
    835                 840                 845

Asn Asn Ala Arg Ser Ala Asn Tyr Ala Leu Val Lys Asn Ala Pro Phe
850                 855                 860

Ala His Ser Ala Thr Pro Asn Leu Val Ala Ile Asn Gln His Asp Phe
865                 870                 875                 880

Gly Thr Ile Glu Ser Val Phe Glu Leu Ala Asn Arg Ser Lys Asp Ile
                885                 890                 895

Asp Thr Leu Tyr Thr His Ser Gly Ala Lys Gly Arg Asp Leu Leu Gln
            900                 905                 910

Thr Leu Leu Ile Asp Ser His Asp Ala Gly Tyr Ala Arg Gln Met Ile
            915                 920                 925

Asp Asn Thr Ser Thr Gly Glu Ile Thr Lys Gln Leu Asn Ala Ala Thr
    930                 935                 940

Thr Thr Leu Asn Asn Ile Ala Ser Leu Glu His Lys Thr Ser Ser Leu
945                 950                 955                 960

Gln Thr Leu Ser Leu Ser Asn Ala Met Ile Leu Asn Ser Arg Leu Val
            965                 970                 975

Asn Leu Ser Arg Lys His Thr Asn Asn Ile Asp Ser Phe Ala Lys Arg
            980                 985                 990

Leu Gln Ala Leu Lys Asp Gln Arg Phe Ala Ser Leu Glu Ser Ala Ala
        995                 1000                1005

Glu Val Leu Tyr Gln Phe Ala Pro Lys Tyr Glu Lys Pro Thr Asn
    1010                1015                1020

Val Trp Ala Asn Ala Ile Gly Gly Ala Ser Leu Asn Asn Gly Ser
    1025                1030                1035

Asn Ala Ser Leu Tyr Gly Thr Ser Ala Gly Val Asp Ala Tyr Leu
    1040                1045                1050

Asn Gly Gln Val Glu Ala Ile Val Gly Gly Phe Gly Ser Tyr Gly
```

```
            1055                1060                1065

Tyr  Ser  Ser  Phe  Ser  Asn  Arg  Ala  Asn  Ser  Leu  Asn  Ser  Gly  Ala
          1070                1075                1080

Asn  Asn  Thr  Asn  Phe  Gly  Val  Tyr  Ser  Arg  Ile  Phe  Ala  Asn  Gln
          1085                1090                1095

His  Glu  Phe  Asp  Phe  Glu  Ala  Gln  Gly  Ala  Leu  Gly  Ser  Asp  Gln
          1100                1105                1110

Ser  Ser  Leu  Asn  Phe  Lys  Ser  Ala  Leu  Leu  Gln  Asp  Leu  Asn  Gln
          1115                1120                1125

Ser  Tyr  Asn  Tyr  Leu  Ala  Tyr  Ser  Ala  Ala  Thr  Arg  Ala  Ser  Tyr
          1130                1135                1140

Gly  Tyr  Asp  Phe  Ala  Phe  Phe  Lys  Asn  Ala  Leu  Val  Leu  Lys  Pro
          1145                1150                1155

Ser  Val  Gly  Val  Ser  Tyr  Asn  His  Leu  Gly  Ser  Thr  Asn  Phe  Lys
          1160                1165                1170

Ser  Asn  Ser  Thr  Asn  Lys  Val  Ala  Leu  Ser  Asn  Gly  Ser  Ser  Ser
          1175                1180                1185

Gln  His  Leu  Phe  Asn  Ala  Ser  Ala  Asn  Val  Glu  Ala  Arg  Tyr  Tyr
          1190                1195                1200

Tyr  Gly  Asp  Thr  Ser  Tyr  Phe  Tyr  Met  Asn  Ala  Gly  Val  Leu  Gln
          1205                1210                1215

Glu  Phe  Ala  Asn  Phe  Gly  Ser  Ser  Asn  Ala  Val  Ser  Leu  Asn  Thr
          1220                1225                1230

Phe  Lys  Val  Asn  Ala  Ala  Arg  Asn  Pro  Leu  Asn  Thr  His  Ala  Arg
          1235                1240                1245

Val  Met  Met  Gly  Gly  Glu  Leu  Gln  Leu  Ala  Lys  Glu  Val  Phe  Leu
          1250                1255                1260

Asn  Leu  Gly  Phe  Val  Tyr  Leu  His  Asn  Leu  Ile  Ser  Asn  Ile  Gly
          1265                1270                1275

His  Phe  Ala  Ser  Asn  Leu  Gly  Met  Arg  Tyr  Ser  Phe
          1280                1285                1290

<210> SEQ ID NO 9
<211> LENGTH: 1296
<212> TYPE: PRT
<213> ORGANISM: Helicobacter pylori  P12

<400> SEQUENCE: 9

Met  Glu  Ile  Gln  Gln  Thr  His  Arg  Lys  Ile  Asn  Arg  Pro  Leu  Val  Ser
1                   5                   10                  15

Leu  Ala  Leu  Val  Gly  Ala  Leu  Val  Ser  Ile  Thr  Pro  Gln  Gln  Ser  His
                    20                  25                  30

Ala  Ala  Phe  Phe  Thr  Thr  Val  Ile  Ile  Pro  Ala  Ile  Val  Gly  Gly  Ile
                    35                  40                  45

Ala  Ser  Gly  Ala  Ala  Val  Gly  Thr  Val  Ser  Gly  Leu  Leu  Gly  Trp  Gly
            50                  55                  60

Leu  Lys  Gln  Ala  Glu  Glu  Ala  Asn  Lys  Thr  Pro  Asp  Lys  Pro  Asp  Lys
65                  70                  75                  80

Val  Trp  Arg  Ile  Gln  Ala  Gly  Lys  Gly  Phe  Asn  Glu  Phe  Pro  Asn  Lys
                    85                  90                  95

Glu  Tyr  Asp  Leu  Tyr  Arg  Ser  Leu  Leu  Ser  Ser  Lys  Ile  Asp  Gly  Gly
                    100                 105                 110

Trp  Asp  Trp  Gly  Asn  Ala  Ala  Thr  His  Tyr  Trp  Val  Lys  Gly  Gly  Gln
                    115                 120                 125
```

```
Trp Asn Lys Leu Glu Val Asp Met Lys Asp Ala Val Gly Thr Tyr Asn
130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
            180                 185                 190

Lys Asn Ile Ser Ile Asp Asn Phe Leu Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Ser Lys Asn Ala Glu Ile Ser Leu Tyr Asp
225                 230                 235                 240

Gly Ala Thr Leu Asn Leu Ala Ser Ser Ser Val Lys Leu Met Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
    275                 280                 285

His Leu Thr Val Gly Asp Arg Asn Ala Ala Gln Ala Gly Ile Ile Ala
290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                325                 330                 335

Asn Thr Pro Ser Gln Ser Gly Ala Lys Asn Asp Lys Asn Glu Ser Ala
            340                 345                 350

Lys Asn Asp Lys Gln Glu Ser Ser Gln Asn Asn Ser Asn Thr Gln Val
        355                 360                 365

Ile Asn Pro Pro Asn Ser Ala Gln Lys Thr Glu Val Gln Pro Thr Gln
    370                 375                 380

Val Ile Asp Gly Pro Phe Ala Gly Gly Lys Asp Thr Val Val Asn Ile
385                 390                 395                 400

Asn Arg Ile Asn Thr Asn Ala Asp Gly Thr Ile Arg Val Gly Gly Tyr
                405                 410                 415

Lys Ala Ser Leu Thr Thr Asn Ala Ala His Leu His Ile Gly Lys Gly
            420                 425                 430

Gly Val Asn Leu Ser Asn Gln Ala Ser Gly Arg Thr Leu Leu Val Glu
        435                 440                 445

Asn Leu Thr Gly Asn Ile Thr Val Asp Gly Pro Leu Arg Val Asn Asn
450                 455                 460

Gln Val Gly Gly Tyr Ala Leu Ala Gly Ser Ser Ala Asn Phe Glu Phe
465                 470                 475                 480

Lys Ala Gly Thr Asp Thr Lys Asn Gly Thr Ala Thr Phe Asn Asn Asp
                485                 490                 495

Ile Ser Leu Gly Arg Phe Val Asn Leu Lys Val Asp Ala His Thr Ala
            500                 505                 510

Asn Phe Lys Gly Ile Asp Thr Gly Asn Gly Gly Phe Asn Thr Leu Asp
        515                 520                 525

Phe Ser Gly Val Thr Asp Lys Val Asn Ile Asn Lys Leu Ile Thr Ala
    530                 535                 540

Ser Thr Asn Val Ala Ile Lys Asn Phe Asn Ile Asn Glu Leu Leu Val
```

-continued

```
545                 550                 555                 560
Lys Thr Asn Gly Val Ser Val Gly Glu Tyr Thr His Phe Ser Glu Asp
                565                 570                 575

Ile Gly Ser Gln Ser Arg Ile Asn Thr Val Arg Leu Glu Thr Gly Thr
            580                 585                 590

Arg Ser Ile Phe Ser Gly Gly Val Lys Phe Lys Gly Gly Glu Lys Leu
        595                 600                 605

Val Ile Asn Asp Phe Tyr Tyr Ala Pro Trp Asn Tyr Phe Asp Ala Arg
    610                 615                 620

Asn Ile Lys Asn Val Glu Ile Thr Asn Lys Leu Ala Phe Gly Pro Gln
625                 630                 635                 640

Gly Ser Pro Trp Gly Thr Ser Lys Leu Met Phe Asn Asn Leu Thr Leu
                645                 650                 655

Gly Gln Asn Ala Val Met Asp Tyr Ser Gln Phe Ser Asn Leu Thr Ile
            660                 665                 670

Gln Gly Asp Phe Val Asn Asn Gln Gly Thr Ile Asn Tyr Leu Val Arg
        675                 680                 685

Gly Gly Gln Val Ala Thr Leu Asn Val Gly Asn Ala Ala Met Phe
    690                 695                 700

Phe Asn Asn Asn Val Asp Ser Ala Thr Gly Phe Tyr Gln Pro Leu Met
705                 710                 715                 720

Lys Ile Asn Ser Ala Gln Asp Leu Ile Lys Asn Lys Glu His Val Leu
                725                 730                 735

Leu Lys Ala Lys Ile Ile Gly Tyr Gly Asn Val Ser Ala Gly Thr Asn
            740                 745                 750

Ser Ile Ser Asn Val Asn Leu Ile Glu Gln Phe Lys Glu Arg Leu Ala
        755                 760                 765

Leu Tyr Glu His Asn Asn Arg Met Asp Ile Cys Val Val Arg Asn Thr
    770                 775                 780

Asp Asp Ile Lys Ala Cys Gly Thr Ala Ile Gly Asn Gln Ser Met Val
785                 790                 795                 800

Asn Asn Pro Asp Asn Tyr Lys Tyr Leu Ile Gly Lys Ala Trp Lys Asn
                805                 810                 815

Ile Gly Ile Ser Lys Thr Ala Asn Gly Ser Lys Ile Ser Val His Tyr
            820                 825                 830

Leu Gly Asn Ser Thr Pro Thr Glu Asn Ser Gly Asn Thr Thr Asn Leu
        835                 840                 845

Pro Thr Asn Thr Thr Ser Asn Ala Arg Ser Ala Lys Asn Ala Leu Ala
    850                 855                 860

Gln Asn Ala Pro Phe Ala Gln Pro Ser Ala Thr Pro Ser Leu Val Ala
865                 870                 875                 880

Ile Asn Gln His Asp Phe Gly Thr Ile Glu Ser Val Phe Glu Leu Ala
                885                 890                 895

Asn Arg Ser Lys Asp Ile Asp Thr Leu Tyr Thr His Ser Gly Ala Gln
            900                 905                 910

Gly Arg Asn Leu Leu Gln Thr Leu Ile Asp Ser His Asp Ala Gly
        915                 920                 925

Tyr Ala Arg Gln Met Ile Asp Asn Thr Ser Thr Gly Glu Ile Ile Lys
    930                 935                 940

Gln Leu Asn Ala Ala Thr Thr Thr Leu Asn Asn Val Ala Ser Leu Glu
945                 950                 955                 960

His Lys Gln Ser Gly Leu Gln Thr Leu Ser Leu Ser Asn Ala Met Ile
                965                 970                 975
```

```
Leu Asn Ser Arg Leu Val Asn Leu Ser Arg Arg His Thr Asn Asn Ile
            980                 985                 990

Asp Ser Phe Ala Gln Arg Leu Gln  Ala Leu Lys Asp Gln  Lys Phe Ala
            995                 1000                1005

Ser Leu Glu Ser Ala Ala Glu Val Leu Tyr Gln Phe Ala Pro Lys
        1010                1015                1020

Tyr Glu Lys Pro Thr Asn Val Trp Ala Asn Ala Ile Gly Gly Thr
        1025                1030                1035

Ser Leu Asn Asn Gly Gly Asn Ala Ser Leu Tyr Gly Thr Ser Ala
        1040                1045                1050

Gly Val Asp Ala Tyr Leu Asn Gly Glu Val Glu Ala Ile Val Gly
        1055                1060                1065

Gly Phe Gly Ser Tyr Gly Tyr Ser Ser Phe Ser Asn Gln Ala Asn
        1070                1075                1080

Ser Leu Asn Ser Gly Ala Asn Asn Thr Asn Phe Gly Val Tyr Ser
        1085                1090                1095

Arg Leu Phe Ala Asn Gln His Glu Phe Asp Phe Glu Ala Gln Gly
        1100                1105                1110

Ala Leu Gly Ser Asp Gln Ser Ser Leu Asn Phe Lys Ser Ala Leu
        1115                1120                1125

Leu Arg Asp Leu Asn Gln Ser Tyr Asn Tyr Leu Ala Tyr Ser Ala
        1130                1135                1140

Ala Thr Arg Ala Ser Tyr Gly Tyr Asp Phe Ala Phe Phe Arg Asn
        1145                1150                1155

Ala Leu Val Leu Lys Pro Ser Val Gly Val Ser Tyr Asn His Leu
        1160                1165                1170

Gly Ser Thr Asn Phe Lys Ser Asn Ser Thr Asn Gln Val Ala Leu
        1175                1180                1185

Lys Asn Gly Ser Ser Ser Gln His Leu Phe Asn Ala Ser Ala Asn
        1190                1195                1200

Val Glu Ala Arg Tyr Tyr Tyr Gly Asp Thr Ser Tyr Phe Tyr Met
        1205                1210                1215

Asn Ala Gly Val Leu Gln Glu Phe Ala Asn Phe Gly Ser Ser Asn
        1220                1225                1230

Ala Val Ser Leu Asn Thr Phe Lys Val Asn Ala Ala Arg Asn Pro
        1235                1240                1245

Leu Asn Thr His Ala Arg Val Met Met Gly Gly Glu Leu Lys Leu
        1250                1255                1260

Ala Lys Glu Val Phe Leu Asn Leu Gly Phe Val Tyr Leu His Asn
        1265                1270                1275

Leu Ile Ser Asn Ile Gly His Phe Ala Ser Asn Leu Gly Met Arg
        1280                1285                1290

Tyr Ser Phe
        1295

<210> SEQ ID NO 10
<211> LENGTH: 1291
<212> TYPE: PRT
<213> ORGANISM: Helicobacter pylori

<400> SEQUENCE: 10

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
```

-continued

```
                20                  25                  30
Ala Ala Phe Phe Thr Thr Val Ile Ile Pro Ala Ile Val Gly Gly Ile
            35                  40                  45
Ala Thr Gly Ala Ala Val Gly Thr Val Ser Gly Leu Leu Gly Trp Gly
        50                  55                  60
Leu Lys Gln Ala Glu Glu Ala Asn Lys Thr Pro Asp Lys Pro Asp Lys
 65                  70                  75                  80
Val Trp Arg Ile Gln Ala Gly Lys Gly Phe Asn Glu Phe Pro Asn Lys
                85                  90                  95
Glu Tyr Asp Leu Tyr Lys Ser Leu Leu Ser Ser Lys Ile Asp Gly Gly
            100                 105                 110
Trp Asp Trp Gly Asn Ala Ala Arg His Tyr Trp Val Lys Asp Gly Gln
        115                 120                 125
Trp Asn Lys Leu Glu Val Asp Met Gln Asn Ala Val Gly Thr Tyr Asn
        130                 135                 140
Leu Ser Gly Leu Ile Asn Phe Thr Gly Gly Asp Leu Asp Val Asn Met
145                 150                 155                 160
Gln Lys Ala Thr Leu Arg Leu Gly Gln Phe Asn Gly Asn Ser Phe Thr
                165                 170                 175
Ser Tyr Lys Asp Ser Ala Asp Arg Thr Thr Arg Val Asp Phe Asn Ala
            180                 185                 190
Lys Asn Ile Leu Ile Asp Asn Phe Leu Glu Ile Asn Asn Arg Val Gly
        195                 200                 205
Ser Gly Ala Gly Arg Lys Ala Ser Ser Thr Val Leu Thr Leu Gln Ala
        210                 215                 220
Ser Glu Gly Ile Thr Ser Arg Glu Asn Ala Glu Ile Ser Leu Tyr Asp
225                 230                 235                 240
Gly Ala Thr Leu Asn Leu Ala Ser Asn Ser Val Lys Leu Met Gly Asn
                245                 250                 255
Val Trp Met Gly Arg Leu Gln Tyr Val Gly Ala Tyr Leu Ala Pro Ser
            260                 265                 270
Tyr Ser Thr Ile Asn Thr Ser Lys Val Thr Gly Glu Val Asn Phe Asn
        275                 280                 285
His Leu Thr Val Gly Asp His Asn Ala Ala Gln Ala Gly Ile Ile Ala
        290                 295                 300
Ser Asn Lys Thr His Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Asn
                325                 330                 335
Asp Lys Pro Ser Asn Thr Thr Gln Asn Asn Ala Lys Asn Asp Lys Gln
            340                 345                 350
Glu Ser Ser Gln Asn Asn Ser Asn Thr Gln Val Ile Asn Pro Pro Asn
        355                 360                 365
Ser Ala Gln Lys Thr Glu Ile Gln Pro Thr Gln Val Ile Asp Gly Pro
        370                 375                 380
Phe Ala Gly Gly Lys Asn Thr Val Val Asn Ile Asn Arg Ile Asn Thr
385                 390                 395                 400
Asn Ala Asp Gly Thr Ile Arg Val Gly Gly Phe Lys Ala Ser Leu Thr
                405                 410                 415
Thr Asn Ala Ala His Leu His Ile Gly Lys Gly Gly Ile Asn Leu Ser
            420                 425                 430
Asn Gln Ala Ser Gly Arg Ser Leu Leu Val Glu Asn Leu Thr Gly Asn
        435                 440                 445
```

```
Ile Thr Val Asp Gly Pro Leu Arg Val Asn Asn Gln Val Gly Gly Tyr
    450                 455                 460

Ala Leu Ala Gly Ser Ser Ala Asn Phe Glu Phe Lys Ala Gly Thr Asp
465                 470                 475                 480

Thr Lys Asn Gly Thr Ala Thr Phe Asn Asn Asp Ile Ser Leu Gly Arg
                485                 490                 495

Phe Val Asn Leu Lys Val Asp Ala His Thr Ala Asn Phe Lys Gly Ile
                500                 505                 510

Asp Thr Gly Asn Gly Gly Phe Asn Thr Leu Asp Phe Ser Gly Val Thr
                515                 520                 525

Asn Lys Val Asn Ile Asn Lys Leu Ile Thr Ala Ser Thr Asn Val Ala
530                 535                 540

Val Lys Asn Phe Asn Ile Asn Glu Leu Val Val Lys Thr Asn Gly Val
545                 550                 555                 560

Ser Val Gly Glu Tyr Thr His Phe Ser Glu Asp Ile Gly Ser Gln Ser
                565                 570                 575

Arg Ile Asn Thr Val Arg Leu Glu Thr Gly Thr Arg Ser Ile Tyr Ser
                580                 585                 590

Gly Gly Val Lys Phe Lys Gly Gly Glu Lys Leu Val Ile Asn Asp Phe
                595                 600                 605

Tyr Tyr Ala Pro Trp Asn Tyr Phe Asp Ala Arg Asn Ile Lys Asn Val
610                 615                 620

Glu Ile Thr Asn Lys Leu Ala Phe Gly Pro Gln Gly Ser Pro Trp Gly
625                 630                 635                 640

Thr Ala Lys Leu Met Phe Asn Asn Leu Thr Leu Gly Gln Asn Ala Val
                645                 650                 655

Met Asp Tyr Ser Gln Phe Ser Asn Leu Thr Ile Gln Gly Asp Phe Val
                660                 665                 670

Asn Asn Gln Gly Thr Ile Asn Tyr Leu Val Arg Gly Gly Gln Val Ala
                675                 680                 685

Thr Leu Asn Val Gly Asn Ala Ala Met Phe Phe Ser Asn Asn Val
                690                 695                 700

Asp Ser Ala Thr Gly Phe Tyr Gln Pro Leu Met Lys Ile Asn Ser Ala
705                 710                 715                 720

Gln Asp Leu Ile Lys Asn Lys Glu His Val Leu Leu Lys Ala Lys Ile
                725                 730                 735

Ile Gly Tyr Gly Asn Val Ser Ala Gly Thr Asp Ser Ile Ala Asn Val
                740                 745                 750

Asn Leu Ile Glu Gln Phe Lys Glu Arg Leu Ala Leu Tyr Asn Asn Asn
                755                 760                 765

Asn Arg Met Asp Ile Cys Val Val Arg Asn Thr Asp Asp Ile Lys Ala
                770                 775                 780

Cys Gly Thr Ala Ile Gly Asn Gln Ser Met Val Asn Asn Pro Glu Asn
785                 790                 795                 800

Tyr Lys Tyr Leu Glu Gly Lys Ala Trp Lys Asn Ile Gly Ile Ser Lys
                805                 810                 815

Thr Ala Asn Gly Ser Lys Ile Ser Val His Tyr Leu Gly Asn Ser Thr
                820                 825                 830

Pro Thr Glu Asn Gly Gly Asn Thr Thr Asn Leu Pro Thr Asn Thr Thr
                835                 840                 845

Asn Lys Val Arg Phe Ala Ser Tyr Ala Leu Ile Lys Asn Ala Pro Phe
850                 855                 860
```

Ala Arg Tyr Ser Ala Thr Pro Asn Leu Val Ala Ile Asn Gln His Asp
865                 870                 875                 880

Phe Gly Thr Ile Glu Ser Val Phe Glu Leu Ala Asn Arg Ser Asn Asp
            885                 890                 895

Ile Asp Thr Leu Tyr Ala Asn Ser Gly Ala Gln Gly Arg Asp Leu Leu
                900                 905                 910

Gln Thr Leu Leu Ile Asp Ser His Asp Ala Gly Tyr Ala Arg Thr Met
            915                 920                 925

Ile Asp Ala Thr Ser Ala Asn Glu Ile Thr Lys Gln Leu Asn Thr Ala
            930                 935                 940

Thr Thr Thr Leu Asn Asn Ile Ala Ser Leu Glu His Lys Thr Ser Gly
945                 950                 955                 960

Leu Gln Thr Leu Ser Leu Ser Asn Ala Met Ile Leu Asn Ser Arg Leu
                965                 970                 975

Val Asn Leu Ser Arg Arg His Thr Asn His Ile Asp Ser Phe Ala Lys
                980                 985                 990

Arg Leu Gln Ala Leu Lys Asp Gln Arg Phe Ala Ser Leu Glu Ser Ala
            995                 1000                1005

Ala Glu Val Leu Tyr Gln Phe Ala Pro Lys Tyr Glu Lys Pro Thr
    1010                1015                1020

Asn Val Trp Ala Asn Ala Ile Gly Gly Thr Ser Leu Asn Ser Gly
    1025                1030                1035

Gly Asn Ala Ser Leu Tyr Gly Thr Ser Ala Gly Val Asp Ala Tyr
    1040                1045                1050

Leu Asn Gly Glu Val Glu Ala Ile Val Gly Gly Phe Gly Ser Tyr
    1055                1060                1065

Gly Tyr Ser Ser Phe Ser Asn Gln Ala Asn Ser Leu Asn Ser Gly
    1070                1075                1080

Ala Asn Asn Thr Asn Phe Gly Val Tyr Ser Arg Ile Phe Ala Asn
    1085                1090                1095

Gln His Glu Phe Asp Phe Glu Ala Gln Gly Ala Leu Gly Ser Asp
    1100                1105                1110

Gln Ser Ser Leu Asn Phe Lys Ser Ala Leu Leu Arg Asp Leu Asn
    1115                1120                1125

Gln Ser Tyr Asn Tyr Leu Ala Tyr Ser Ala Ala Thr Arg Ala Ser
    1130                1135                1140

Tyr Gly Tyr Asp Phe Ala Phe Phe Arg Asn Ala Leu Val Leu Lys
    1145                1150                1155

Pro Ser Val Gly Val Ser Tyr Asn His Leu Gly Ser Thr Asn Phe
    1160                1165                1170

Lys Ser Asn Ser Asn Gln Lys Val Ala Leu Lys Asn Gly Ala Ser
    1175                1180                1185

Ser Gln His Leu Phe Asn Ala Ser Ala Asn Val Glu Ala Arg Tyr
    1190                1195                1200

Tyr Tyr Gly Asp Thr Ser Tyr Phe Tyr Met Asn Ala Gly Val Leu
    1205                1210                1215

Gln Glu Phe Ala Asn Phe Gly Ser Ser Asn Ala Val Ser Leu Asn
    1220                1225                1230

Thr Phe Lys Val Asn Ala Thr Arg Asn Pro Leu Asn Thr His Ala
    1235                1240                1245

Arg Val Met Met Gly Gly Glu Leu Lys Leu Ala Lys Glu Val Phe
    1250                1255                1260

Leu Asn Leu Gly Phe Val Tyr Leu His Asn Leu Ile Ser Asn Ile

```
           1265                1270                1275
Gly His  Phe Ala Ser Asn Leu  Gly Met Arg Tyr Ser  Phe
    1280                1285                1290

<210> SEQ ID NO 11
<211> LENGTH: 1297
<212> TYPE: PRT
<213> ORGANISM: Helicobacter pylori NCTC 11638

<400> SEQUENCE: 11

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
            20                  25                  30

Ala Ala Phe Phe Thr Thr Val Ile Ile Pro Ala Ile Val Gly Gly Ile
        35                  40                  45

Ala Thr Gly Thr Ala Val Gly Thr Val Ser Gly Leu Leu Ser Trp Gly
    50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Arg Ser Leu Leu Ser Ser Lys Ile Asp Gly Gly
            100                 105                 110

Trp Asp Trp Gly Asn Ala Ala Arg His Tyr Trp Val Lys Gly Gly Gln
        115                 120                 125

Gln Asn Lys Leu Glu Val Asp Met Lys Asp Ala Val Gly Thr Tyr Thr
    130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
            180                 185                 190

Lys Asn Ile Ser Ile Asp Asn Phe Val Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Asp Lys Asn Ala Glu Ile Ser Leu Tyr Asp
225                 230                 235                 240

Gly Ala Thr Leu Asn Leu Ala Ser Ser Ser Val Lys Leu Met Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
        275                 280                 285

His Leu Thr Val Gly Asp Lys Asn Ala Ala Gln Ala Gly Ile Ile Ala
    290                 295                 300

Asn Lys Lys Thr Asn Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                325                 330                 335

Asn Thr Pro Ser Gln Ser Gly Ala Lys Asn Asp Lys Asn Glu Ser Ala
            340                 345                 350
```

-continued

```
Lys Asn Asp Lys Gln Glu Ser Gln Asn Ser Asn Thr Gln Val
            355                 360             365

Ile Asn Pro Pro Asn Ser Ala Gln Lys Thr Glu Val Gln Pro Thr Gln
    370                 375                 380

Val Ile Asp Gly Pro Phe Ala Gly Gly Lys Asp Thr Val Val Asn Ile
385                 390                 395                 400

Asn Arg Ile Asn Thr Asn Ala Asp Gly Thr Ile Arg Val Gly Gly Phe
                405                 410                 415

Lys Ala Ser Leu Thr Thr Asn Ala Ala His Leu His Ile Gly Lys Gly
            420                 425                 430

Gly Val Asn Leu Ser Asn Gln Ala Ser Gly Arg Ser Leu Ile Val Glu
            435                 440                 445

Asn Leu Thr Gly Asn Ile Thr Val Asp Gly Pro Leu Arg Val Asn Asn
    450                 455                 460

Gln Val Gly Gly Tyr Ala Leu Ala Gly Ser Ser Ala Asn Phe Glu Phe
465                 470                 475                 480

Lys Ala Gly Thr Asp Thr Lys Asn Gly Thr Ala Thr Phe Asn Asn Asp
                485                 490                 495

Ile Ser Leu Gly Arg Phe Val Asn Leu Lys Val Asp Ala His Thr Ala
            500                 505                 510

Asn Phe Lys Gly Ile Asp Thr Gly Asn Gly Phe Asn Thr Leu Asp
    515                 520                 525

Phe Ser Gly Val Thr Asp Lys Val Asn Ile Asn Lys Leu Ile Thr Ala
            530                 535                 540

Ser Thr Asn Val Ala Val Lys Asn Phe Asn Ile Asn Glu Leu Ile Val
545                 550                 555                 560

Lys Thr Asn Gly Ile Ser Val Gly Glu Tyr Thr His Phe Ser Glu Asp
                565                 570                 575

Ile Gly Ser Gln Ser Arg Ile Asn Thr Val Arg Leu Glu Thr Gly Thr
            580                 585                 590

Arg Ser Leu Phe Ser Gly Gly Val Lys Phe Lys Gly Gly Glu Lys Leu
            595                 600                 605

Val Ile Asp Glu Phe Tyr Tyr Ser Pro Trp Asn Tyr Phe Asp Ala Arg
610                 615                 620

Asn Ile Lys Asn Val Glu Ile Thr Asn Lys Leu Ala Phe Gly Pro Gln
625                 630                 635                 640

Gly Ser Pro Trp Gly Thr Ser Lys Leu Met Phe Asn Asn Leu Thr Leu
                645                 650                 655

Gly Gln Asn Ala Val Met Asp Tyr Ser Gln Phe Ser Asn Leu Thr Ile
            660                 665                 670

Gln Gly Asp Phe Ile Asn Asn Gln Gly Thr Ile Asn Tyr Leu Val Arg
            675                 680                 685

Gly Gly Lys Val Ala Thr Leu Ser Val Gly Asn Ala Ala Met Met
690                 695                 700

Phe Asn Asn Asp Ile Asp Ser Ala Thr Gly Phe Tyr Lys Pro Leu Ile
705                 710                 715                 720

Lys Ile Asn Ser Ala Gln Asp Leu Ile Lys Asn Thr Glu His Val Leu
            725                 730                 735

Leu Lys Ala Lys Ile Ile Gly Tyr Gly Asn Val Ser Thr Gly Thr Asn
            740                 745                 750

Gly Ile Ser Asn Val Asn Leu Glu Glu Gln Phe Lys Glu Arg Leu Ala
            755                 760                 765

Leu Tyr Asn Asn Asn Asn Arg Met Asp Thr Cys Val Val Arg Asn Thr
```

```
            770              775              780
Asp Asp Ile Lys Ala Cys Gly Met Ala Ile Gly Asp Gln Ser Met Val
785                 790                 795                 800

Asn Asn Pro Asp Asn Tyr Lys Tyr Leu Ile Gly Lys Ala Trp Lys Asn
                805                 810                 815

Ile Gly Ile Ser Lys Thr Ala Asn Gly Ser Lys Ile Ser Val Tyr Tyr
                820                 825                 830

Leu Gly Asn Ser Thr Pro Thr Glu Asn Gly Gly Asn Thr Thr Asn Leu
                835                 840                 845

Pro Thr Asn Thr Thr Ser Asn Ala Arg Ser Ala Asn Asn Ala Leu Ala
850                 855                 860

Gln Asn Ala Pro Phe Ala Gln Pro Ser Ala Thr Pro Asn Leu Val Ala
865                 870                 875                 880

Ile Asn Gln His Asp Phe Gly Thr Ile Glu Ser Val Phe Glu Leu Ala
                885                 890                 895

Asn Arg Ser Lys Asp Ile Asp Thr Leu Tyr Ala Asn Ser Gly Ala Gln
                900                 905                 910

Gly Arg Asp Leu Leu Gln Thr Leu Leu Ile Asp Ser His Asp Ala Gly
                915                 920                 925

Tyr Ala Arg Lys Met Ile Asp Ala Thr Ser Ala Asn Glu Ile Thr Lys
                930                 935                 940

Gln Leu Asn Thr Ala Thr Thr Thr Leu Asn Asn Ile Ala Ser Leu Glu
945                 950                 955                 960

His Lys Thr Ser Gly Leu Gln Thr Leu Ser Leu Ser Asn Ala Met Ile
                965                 970                 975

Leu Asn Ser Arg Leu Val Asn Leu Ser Arg Arg His Thr Asn His Ile
                980                 985                 990

Asp Ser Phe Ala Lys Arg Leu Gln  Ala Leu Lys Asp Gln  Lys Phe Ala
                995                  1000                 1005

Ser Leu  Glu Ser Ala Ala Glu  Val Leu Tyr Gln Phe  Ala Pro Lys
     1010                 1015                 1020

Tyr Glu  Lys Pro Thr Asn Val  Trp Ala Asn Ala Ile  Gly Gly Thr
     1025                 1030                 1035

Ser Leu  Asn Asn Gly Ser Asn  Ala Ser Leu Tyr Gly  Thr Ser Ala
     1040                 1045                 1050

Gly Val  Asp Ala Tyr Leu Asn  Gly Gln Val Glu Ala  Ile Val Gly
     1055                 1060                 1065

Gly Phe  Gly Ser Tyr Gly Tyr  Ser Ser Phe Asn Asn  Arg Ala Asn
     1070                 1075                 1080

Ser Leu  Asn Ser Gly Ala Asn  Asn Thr Asn Phe Gly  Val Tyr Ser
     1085                 1090                 1095

Arg Ile  Phe Ala Asn Gln His  Glu Phe Asp Phe Glu  Ala Gln Gly
     1100                 1105                 1110

Ala Leu  Gly Ser Asp Gln Ser  Ser Leu Asn Phe Lys  Ser Ala Leu
     1115                 1120                 1125

Leu Gln  Asp Leu Asn Gln Ser  Tyr His Tyr Leu Ala  Tyr Ser Ala
     1130                 1135                 1140

Ala Thr  Arg Ala Ser Tyr Gly  Tyr Asp Phe Ala Phe  Phe Arg Asn
     1145                 1150                 1155

Ala Leu  Val Leu Lys Pro Ser  Val Gly Val Ser Tyr  Asn His Leu
     1160                 1165                 1170

Gly Ser  Thr Asn Phe Lys Ser  Asn Ser Thr Asn Gln  Val Ala Leu
     1175                 1180                 1185
```

```
Lys Asn Gly Ser Ser Ser Gln His Leu Phe Asn Ala Ser Ala Asn
    1190            1195            1200

Val Glu Ala Arg Tyr Tyr Tyr Gly Asp Thr Ser Tyr Phe Tyr Met
    1205            1210            1215

Asn Ala Gly Val Leu Gln Glu Phe Ala His Val Gly Ser Asn Asn
    1220            1225            1230

Ala Ala Ser Leu Asn Thr Phe Lys Val Asn Ala Ala Arg Asn Pro
    1235            1240            1245

Leu Asn Thr His Ala Arg Val Met Met Gly Gly Glu Leu Lys Leu
    1250            1255            1260

Ala Lys Glu Val Phe Leu Asn Leu Gly Val Val Tyr Leu His Asn
    1265            1270            1275

Leu Ile Ser Asn Ile Gly His Phe Ala Ser Asn Leu Gly Met Arg
    1280            1285            1290

Tyr Ser Phe Phe
    1295
```

USE OF HELIOCBACTER PYLORI EXTRACT FOR TREATING OR PREVENTING INFLAMMATORY BOWEL DISEASES AND COELIAC DISEASE

CROSS-REFERENCE TO RELATED APPLICATION

This application is the U.S. national stage application of International Patent Application No. PCT/IB2015/050705, filed Jan. 30, 2015.

The Sequence Listing for this application is labeled "Seq-List.txt" which was created on Jul. 29, 2016 and is 116 KB. The entire content of the sequence listing is incorporated herein by reference in its entirety.

FIELD OF THE INVENTION

The present invention relates to prevention or treatment of hypersensitivity and/or hyperirritability of the colon and/or small intestine and in particular to compositions useful for the prevention of inflammatory bowel disease, in particular Crohn's disease or ulcerative colitis (UC), and for the prevention or treatment of coeliac disease.

BACKGROUND OF THE INVENTION

Crohn's disease (CD) and ulcerative colitis (UC), collectively referred to as inflammatory bowel diseases (IBDs), develop in genetically susceptible individuals as the result of an inappropriately aggressive immune response to ubiquitous antigens of the normal intestinal microflora. Genetic studies have highlighted the importance of host-microbe interactions, and of innate immune recognition of components of the intestinal microbiota, in the pathogenesis of these chronic inflammatory disorders (Abraham et al., 2009, *Inflammatory bowel disease, N. Engl. J. Med.* 361:2066-78). The prevalence of IBDs has increased in most developed countries during the past century, a trend that has been attributed to changes in diet, antibiotic use, and to changing patterns of intestinal colonization (Eckburg et al., 2007, *Clin. Infect. Dis.*, 44:256-62). The biological hallmarks of active inflammatory bowel disease are a pronounced infiltration into the lamina propria of innate and adaptive immune cells and elevated local levels of their cytokine products, especially TNF-α, IL-1β, IFN-γ, and Th17 cell-derived cytokines.

In the last decade, the medical management of IBDs has undergone a major transformation with respect to both treatment options and treatment goals as new treatment modalities have become available. The conventional approach to IBD treatment aims to induce and maintain clinical remission, to improve quality of life and to limit the indications for surgery; patients are treated in a "step-up" fashion with increasingly effective (and increasingly toxic) agents as their disease course progresses (Kemp et al., 2013, *BioDrugs*, 27(6):585-90; Rogler, 2013, Dig Dis., 31(1):83-90). Patients with mild disease receive aminosalicylates or topical corticosteroids such as buclesonide, and those with moderately active or severe disease, or acute flares, are treated with systemic corticosteroids. The more aggressive therapeutic strategies involving immunosuppressive thiopurines (azathioprine or 6-mercaptopurine) and/or biologics targeting tumor necrosis factor (TNF-α) are currently reserved for steroid-refractory patients and surgery is indicated for patients failing biologics. However, there is now increasing evidence that early intervention with immunosuppressives and/or one of the three anti-TNF biologics— intliximab, adalimumab, certolizumab pegol—can confer rapid and prolonged benefits, including reductions in hospitalizations and the need for surgery. Most importantly, such early "top-down" aggressive treatment appears to be "disease-modifying" in that it achieves mucosal healing, a new treatment objective that is now replacing clinical remission as predominant treatment goal (Allen et al., 2011, *Curr. Opin. Gastroenterol.*, 29:397-404). Although recent studies have documented that anti-TNF therapies, alone or in combination with immunosuppressive thiopurines, may change the natural course of IBD by decreasing the need for surgery in both CD and UC patients, only one-third of patients will remain in clinical remission at 1 year, loss of response is frequent (Billioud et al., 2011 *Am. J. Gastroenterol.*, 106: 674-849) and serious side effects (severe and opportunistic infections, increased lymphoma risk, reactivation of latent tuberculosis) are common. Therefore, alternative therapeutic targets are urgently needed; the most promising small molecules and biologics in (early) clinical development are compounds targeting cytokines involved in IBD pathogenesis (IL-12 and IL-23), the α4β7 integrin involved in lymphocyte homing to the gut, and JAK3 kinase, which is involved in cytokine signaling. Additionally, rather experimental strategies attempt to modulate pathogenic immune responses in models of IBD by the introduction of helminths such as *Heligmosomoides polygyrus* (Blum et al., 2012, *J. Immunol.*, 189:2512-20) or *Trichuris suis* (Summers et al., 2005, *Gut* 2005; 54:87-90) or of probiotics (especially *Lactobacillus* or *Bifidobacterium* species or the *Escherichia coli* strain Nissle) (Dylag et al., 2013, *Curr. Pharm. Des.*, PMID: 23755726).

Chronic gastric infection with the bacterial pathogen *Helicobacter pylori* causes gastritis and peptic ulcer disease (Marshall et al., 1984, *Lancet*, 1:1311-5) and represents the most important risk factor for gastric cancer (Huang, 2003, *Gastroenterology* 2003; 125:1636-44) but has also been linked inversely to the risk of developing asthma and other allergic diseases as well as IBD in large epidemiological studies and meta-analyses (Luther et al., 2010, *Inflamm. Bowel Dis.*, 16:1077-84). It has been shown that experimental live *H. pylori* infection, especially when initiated during the neonatal period, protects effectively against allergen-induced asthma that is induced by allergen sensitization and challenge (Arnold et al., 2011, *The Journal of Clinical Investigation*, 121:3088-3093). Mechanistically, asthma protection is due to the development of (Treg-mediated) immune tolerance to *H. pylori*, which cross-protects against allergen-specific Th2 responses. The protective effects of live *H. pylori* are abrogated by antibiotic eradication therapy clearing the bacteria (Arnold et al., 2011, supra).

Since all the current treatments of inflammatory bowel diseases induce more or less severe side effects, alternative treatment strategies are desperately needed. Therefore, there are important needs for new strategies of prevention of development of those disorders.

SUMMARY OF THE INVENTION

The invention relates to the unexpected findings that regular administration of *H. pylori* extract, when delivered orally or systemically, prevents the clinical and histopathological features characteristic of DSS-induced colitis. These protective effects were evident during colonoscopy and upon histological assessment of affected colonic tissues. The endoscopy approach further revealed that *H. pylori* extract induced the production of large quantities of protective mucus composed of the intestinal mucin-2, which required IL-18 signalling on colonic epithelial cells.

A first aspect of the invention provides an *H. pylori* extract or an *H. pylori* extract component or a formulation thereof, for use in the prevention and/or treatment of inflammatory bowel diseases (IBDs), in particular Crohn's disease (CD) and ulcerative colitis (UC), as well as coeliac disease.

A second aspect of the invention relates to a polypeptide selected from a Vac A protein, a fragment or a variant thereof for use in the prevention and/or treatment of inflammatory bowel diseases (IBDs), in particular Crohn's disease (CD) and ulcerative colitis (UC) as well as coeliac disease.

A third aspect of the invention relates to a use of *H. pylori* extract or an *H. pylori* extract component or a polypeptide of the invention, a fragment or a variant thereof for the preparation of a medicament for prevention and/or treatment of inflammatory bowel diseases (IBDs), in particular Crohn's disease (CD) and ulcerative colitis (UC) as well as coeliac disease.

A fourth aspect according to the invention relates to a pharmaceutical formulation comprising a *H. pylori* extract or an *H. pylori* extract component, a polypeptide of the invention, and at least one pharmaceutically acceptable carrier, diluent or excipient thereof.

A fifth aspect of the invention relates to a method of preventing, repressing or treating inflammatory bowel diseases (IBDs), in particular Crohn's disease (CD) and ulcerative colitis (UC), as well as coeliac disease, in a subject, said method comprising administering in a subject in need thereof a therapeutically effective amount of at least one of a *H. pylori* extract, an *H. pylori* extract component or of a polypeptide of the invention, a fragment or a variant thereof, or a pharmaceutical formulation thereof.

DESCRIPTION OF THE FIGURES

FIG. 3 shows examples of amino acid sequences of the Vac A polypeptides described herein. A: s1m1 VacA (Q48245 *H. pylori* strain ATCC 49503/60190) of SEQ ID NO: 1; B: s2m2 VacA of SEQ ID NO: 2; C-J: SEQ ID NO: 3 to SEQ ID NO: 10.

DETAILED DESCRIPTION

Figure 1:
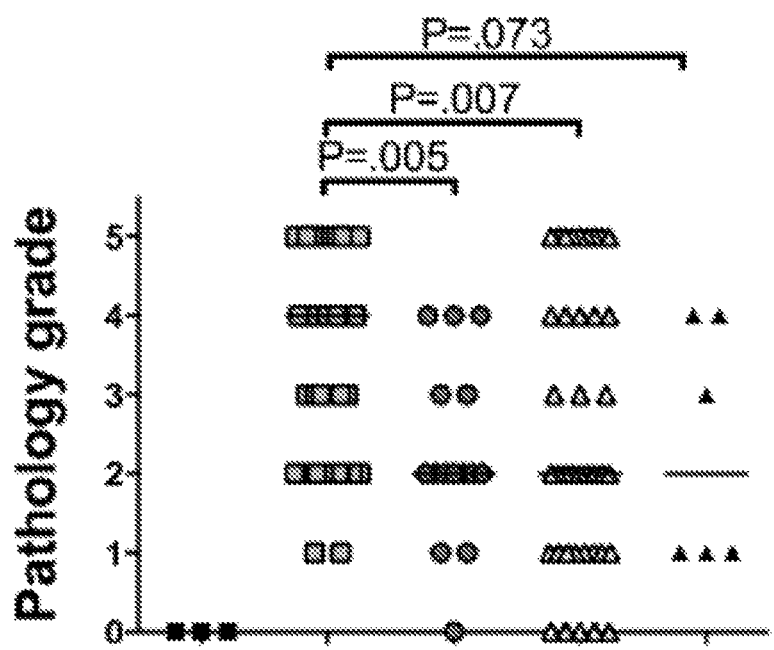
FIG. 1 shows that both the live infection with *H. pylori* as well as the regular intragastric (oral) treatment with *H. pylori* extract effectively reduces the pathology associated with DSS-induced colitis in mice as described under Example 1. A: Histopathology scores; B: Colonoscopy scores in the case of live infection (inf.), extract by p.o. administration (extr. p.o.) and extract by intraperitoneal administration (extr. i.p.); (C, D): representative endoscopic (C) and histopathologic (D) images of all treatment groups (negative control: neg. ctrl; positive control: pos. ctrl; live infection: infection; dead cell extract: extract).
Figure 1:
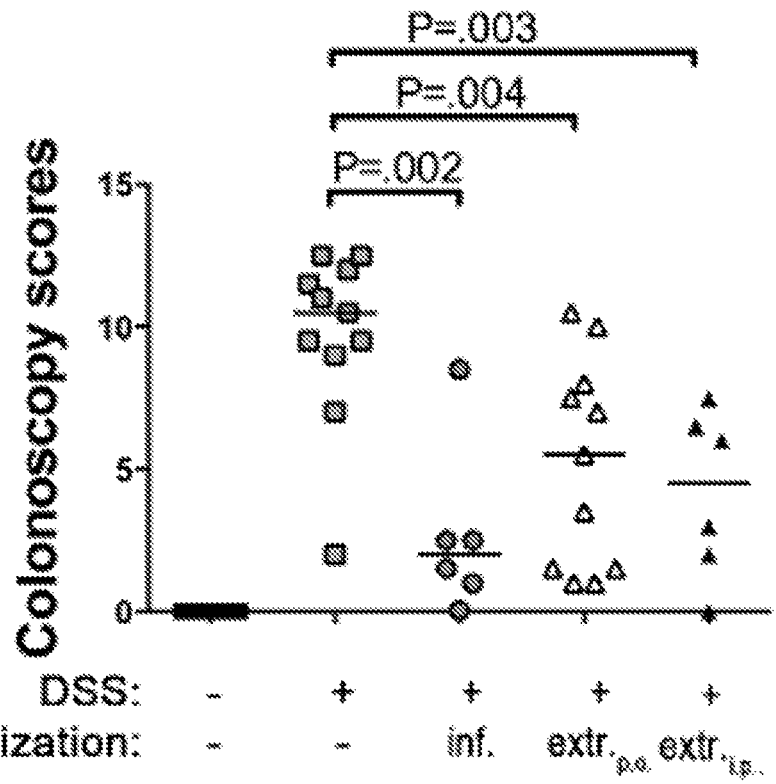
Figure 1:
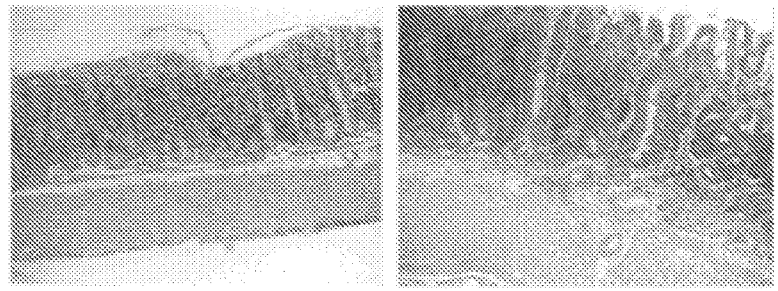
Figure 1:
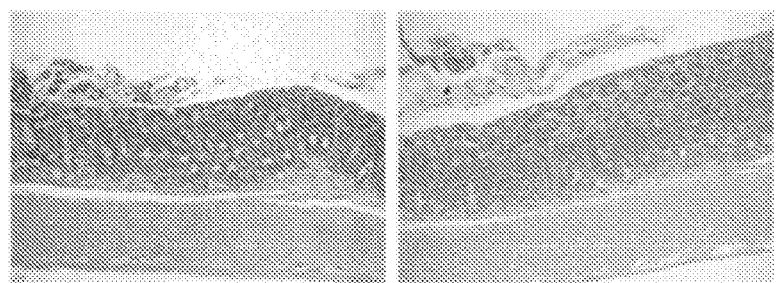

The term "Inflammatory Bowel Disease" (IBD) refers to a group of inflammatory conditions of the colon and small intestine. The main forms of TBD are Crohn's disease and ulcerative colitis (UC). The main difference between Crohn's disease and UC is the location and nature of the inflammatory changes. Crohn's can affect any part of the gastrointestinal tract, from mouth to anus, although a majority of the cases start in the terminal ileum. Ulcerative colitis, in contrast, is restricted to the colon and the rectum. Both disorders may present with any of the following symptoms: abdominal pain, vomiting, diarrhea, rectal bleeding, severe internal cramps/muscle spasms in the region of the pelvis, and weight loss. Anemia is the most prevalent extra-intestinal complication of inflammatory bowel disease. Patients of IBD have an increased risk of colorectal cancer but since the disorder is usually caught much earlier than the general population in routine surveillance of the colon by colonoscopy, patients are much more likely to survive. New evidence suggests that patients with IBD may have an elevated risk of endothelial dysfunction and coronary artery disease. IBD diagnosis is generally made by assessment of inflammatory markers (such as calprotectin) in stool in conjunction with imaging technologies such as optical, ultrasound, magnetic resonance imaging (MRI), X-ray, computed tomography (CT), position emission tomography (PET), single photon emission computed tomography (SPECT) and colonoscopy with biopsy of pathological lesions. The group of IBDs further includes lymphocytic colitis, ischemic colitis, Bechet's disease, diversion colitis, and irritable bowel syndrome.

"Coeliac disease" is an autoimmune disorder of the small intestine that occurs in genetically predisposed people of all ages from middle infancy onward. Symptoms include pain and discomfort in the digestive tract, chronic constipation and diarrhoea, failure to thrive (in children), anaemia and fatigue, but these may be absent, and symptoms in other organ systems have been described. Vitamin deficiencies are often noted in people with coeliac disease owing to the reduced ability of the small intestine to properly absorb nutrients from food. Coeliac disease is caused by a reaction to gliadin, a prolamin (gluten protein) found in wheat, and similar proteins found in the crops of the tribe Triticeae (which includes other common grains such as barley and rye). Upon exposure to gliadin, and specifically to three peptides found in prolamins, the enzyme tissue transglutaminase modifies the protein, and the immune system cross-reacts with the small-bowel tissue, causing an inflammatory reaction. This interferes with the absorption of nutrients because the intestinal villi are responsible for absorption. The only known effective treatment is a lifelong gluten-free diet.

The term "*H. pylori* extract" refers to cell extracts (dead bacteria) from wild-type bacteria (human isolates or laboratory strains of *H. pylori*) or *H. pylori* mutants lacking either entire genes, or parts of genes, or having point mutations introduced, either by random mutagenesis, or transposon mutagenesis.

The term "*H. pylori* extract component" refers to components extracted from the said cell extract such as purified components, comprising polypeptides or produced from either wild type or mutant.

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

The term "fragments" refers to polypeptides comprising a portion of peptide sequence corresponding to contiguous amino acids of a polypeptide set forth herein, including all intermediate lengths and variants thereof.

The term "VacA" includes s1m1 VacA (SEQ ID NO: 1 and 3-10) and s2m2 VacA (SEQ ID NO: 2). Such as described in Cover et al., 1992, *J. Biol. Chem.*, 267: 10570-1057 and Cover et al., 1997, *J. Cell. Biol.*, 138:759-769. According to a particular embodiment, Vac A is s1m1 VacA of SEQ ID NO: 1. According to another embodiment, Vac A is s2m2 VacA of SEQ ID NO: 2. According to another embodiment, Vac A is s1m1 VacA of SEQ ID NO: 8.

The term "variant" applies to both a polynucleotide or a polypeptide. A polypeptide "variant," as the term is used herein, is a peptide or a polypeptide substantially homologous to the referenced peptide sequence, but which has an amino acid sequence different from that of the referenced. Such variants may be naturally occurring or may be synthetically generated, for example, by modifying one or more of the above polypeptide sequences of the invention described herein using any of a number of techniques well known in the art. In many instances, a variant will contain conservative substitutions. Substantially homologous means a variant amino acid sequence which is identical to the referenced peptide sequence except for the deletion, insertion and/or substitution of a few amino acids, e.g. 1, 2, 3, 4, 5, or 6 amino acids. Substantially homologous means a variant amino acid sequence that is at least 80%, at least 85%, at least 90%, at least 95%, at least 96%, at least 97%, at least 98% or at least 99% identical to the referenced amino acid sequence. A variant nucleic acid sequence can be at least 80%, at least 85%, at least 90%, at least 95%, at least 96%, at least 97%, at least 98% or at least 99% identical to the referenced nucleic acid sequence. The identity of two amino acid sequences or of two nucleic acid sequences can be determined by visual inspection and/or mathematical calculation, or more easily by comparing sequence information using known computer program used for sequence comparison such as Clustal package version 1.83.

A variant may comprise a sequence having at least one conservatively substituted amino acid. A "conservative substitution" is one in which an amino acid is substituted for another amino acid that has similar properties, such that one skilled in the art of peptide chemistry would expect the secondary structure and hydropathic nature of the polypeptide to be substantially unchanged (e.g. having similar physiochemical characteristics). Modifications may be made in the structure of the polynucleotides and polypeptides of the present invention and still obtain a functional molecule that encodes a variant or derivative polypeptide with desirable characteristics according to the invention. When it is desired to alter the amino acid sequence of a polypeptide to create an equivalent, or even an improved, variant or portion of a polypeptide of the invention, one skilled in the art will typically change one or more of the codons of the encoding DNA sequence. In making such changes, the hydropathic index, polarity, charge, solubility, hydrophobicity, hydrophilicity and/or the amphipathic nature of the amino acids are considered. The importance of the hydropathic amino acid index in conferring interactive biologic function on a protein is generally understood in the art (Kyte, et al., 1982, *J. Mol. Biol.*, 157: 105-131). Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known (Kyle, el al, 1982, supra). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Table 1 below. The term "variant" also includes a peptide or polypeptide substantially homologous to the referenced peptide sequence, but which has an amino acid sequence different from that of the referenced sequence because one or more amino acids have been chemically modified or substituted by amino acids analogs. This term also includes glycosylated polypeptides.

TABLE 1

| Original residues | Examples of substitutions |
| --- | --- |
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Trp (W) | Phe, Tyr |
| Thr (T) | Ser |
| Tyr (Y) | Trp, Phe, Thr, Ser |
| Val (V) | Ile, Met, Leu, Phe, Ala |

Generally, substitutions for one or more amino acids present in the original polypeptide should be made conservatively. Extracts, polypeptides of the invention, polypeptide fragments and variants thereof are capable of inducing a protective effect against hypersensitivity of the colon and/or small intestine when administered in vivo or a hyperreactivity to gluten as typical of coeliac disease.

Polypeptides of the invention are prepared using any of a variety of well-known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain (Merrifield, 1963, *J. Am. Chem. Soc.*, 85:2149-2146).

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and is not necessarily meant to imply cure or complete abolition of symptoms, but refers to any type of treatment that imparts a benefit to a patient and includes: (a) preventing the disease from occurring in a subject which may be predisposed to the disease but has not yet been diagnosed as having it for example based on familial history, overweight status or age; (b) inhibiting the disease, i.e., arresting its development; or relieving the disease, i.e., causing regression of the disease and/or its symptoms or conditions such as improvement or remediation of damage.

In particular, prevention and/or treatment of IBD and coeliac disease according to the invention comprise to normalize or decrease the inflammatory conditions of the colon and small intestine of an individual. The term "treatment" refers to any type of treatment or prevention that imparts a benefit to a subject afflicted with or at risk of developing an inflammatory conditions of the colon and small intestine, including improvement in the condition of the subject (e.g., in one or more symptoms), delay in the onset of symptoms or slowing the progression of symptoms, etc. According to one aspect, effects of a treatment according to the invention may be observed through one or more the following: generally improved well-being and improvement of symptoms, specifically of abdominal pain, vomiting, diarrhea, rectal bleeding, severe internal cramps/muscle spasms in the region of the pelvis, and weight loss and anemia. Treatment success may manifest itself in improved quality of life and reduced indications for surgery, as well as a reduced need for aggressive therapeutic strategies involving immunosuppressive thiopurines (azathioprine or 6-mercaptopurine) and/or biologics targeting tumor necrosis factor (TNF-$\alpha$) or systemic steroids. Mucosal healing may be another sign of treatment success, along with a reduction in acute flares. In coeliac disease, the effects of the treatment may be observed through a decreased hyperreactivity to gluten, and any of the symptoms mentioned above for the IBDs.

The term "subject" as used herein refers to mammals. For example, mammals contemplated by the present invention include human, primates, domesticated animals such as cattle, sheep, pigs, horses, laboratory rodents and the like.

The term "high-risk" subjects or individuals are subjects that that are at risk to develop inflammatory conditions of the colon and small intestine, in particular of developing Crohn's disease or ulcerative colitis (UC). Those include genetic predisposition such as a history of inflammatory conditions such as genetic (such as NOD2 gene variants), and personal or family history of IBDs. The risk or predisposition of developing inflammatory conditions of the colon and small intestine, in particular of developing Crohn's disease or ulcerative colitis (UC) can be evaluated by assessing personal and family history, and can be confirmed by calprotectin in stool in conjunction with imaging technologies such as optical, ultrasound, magnetic resonance imaging (MRI), X-ray, computed tomography (CT), position emission tomography (PET), single photon emission computed tomography (SPECT) and colonoscopy with biopsy of pathological lesions. The risk or predisposition of developing coeliac disease can be evaluated by assessing personal and family history, and can be confirmed by serological assessment of antibodies to the enzyme tissue transglutaminase (tTG).

The term "efficacy" of a treatment or method according to the invention can be measured based on changes in the course of disease or condition in response to a use or a method according to the invention. For example, the efficacy of a treatment or method according to the invention can be measured by measuring the level of stool calprotectin in the subject before and after the treatment, as well as by colonoscopy and other imaging techniques. The most important indicator of efficacy is self-reported improvement of quality of life, and a reduction in the various symptoms listed above. In coeliac disease patients, the most important indicator of efficacy is the self-reported reduction of gluten hyperreactivity (after consumption of a gluten-containing diet).

The term "non-denaturated" refers to the absence of observed denaturation of the protein (e.g. structure). This can be verified by any method well-known in the art such as gel electrophoresis, gel filtration or mass spectrometry.

The polypeptides of the invention and formulations thereof can be useful at alleviating pre-existing disease in high-risk individuals.

*H. pylori* Extracts and *H. pylori* Extract Components of the Invention in the Form of Purified Peptides

*H. pylori* extract components might be used as cell extract or extracted from the said cell extract such as purified components, comprising polypeptides. Extracts may be prepared from wild-type bacteria (human isolates or laboratory strains of *H. pylori*) or *H. pylori* mutants lacking either entire genes, or parts of genes, or having point mutations introduced, either by random mutagenesis, or transposon mutagenesis, or gene deletion. According to one aspect, *H. pylori* extract components comprise a VacA polypeptide of the invention, fragments and variants thereof as described in the detailed description and they can be administered in different forms including in a form of a dead cell extract (dead) or in a form of a purified synthetic polypeptide (recombinantly produced or obtained by synthesis).

In one aspect, the present invention provides *H. pylori* extract or *H. pylori* extract components from wild-type *H. pylori*.

In one aspect, the present invention provides *H. pylori* extract or *H. pylori* extract components from a mutant *H. pylori*.

In one aspect, the present invention provides VacA polypeptides of the invention, including fragments and variants thereof in the form of an *H. pylori* bacteria cell extract.

In a further aspect, the present invention provides VacA polypeptides of the invention, including fragments and variants thereof in the form of a *H. pylori* bacteria dead cell extract, wherein bacteria cells are non-denaturated killed *H. pylori* bacteria cells.

In a further aspect, the present invention provides VacA polypeptides of the invention, including fragments and variants thereof in the form of a *H. pylori* bacteria dead cell extract, wherein the *H. pylori* bacteria strain is *H. pylori* PMSS1 (Arnold et al. 2011, *Gastroenterology*, 140, 199-209).

The processes which may be used for preparing *H. pylori* cell extract are known to the skilled person and include the use of physical means that produce non-denaturated killed cell bacteria, i.e. under non-denaturating conditions such as described in Laemmli et al., 1970, *Nature*, 277, 680-, such as for example use of the so called "French pressure cell press" (Kelemen et al., 1979, *J. Cell sci.*, 35:431-141). Alternatively, ultra sonication or other methods such as extended freeze drying, repeated cycles of freezing and thawing, lyophilization, homogenization techniques and other cell disruption techniques using physical forces can be applied, as long as they preserve *H. pylori* proteins in native form.

In another further aspect, the present invention provides an *H. pylori* extract, an *H. pylori* extract component, VacA polypeptides of the invention and fragments and variants thereof in the form of a *H. pylori* bacterial cell extract obtainable by a process comprising the steps of:
  (i) harvesting a culture of living bacteria cells;
  (ii) submitting the harvested bacteria to several freeze/thaw cycles in water or aqueous solution of a salt;
  (iii) disrupting the bacterial cells under high pressure, e.g. using a French pressure cell press;
  (iv) collecting the cell extract.

In another aspect, the present invention provides VacA polypeptides of the invention, including fragments and variants thereof in the form of a purified vacA polypeptide.

In another further aspect, the present invention provides VacA polypeptides of the invention, including fragments and variants thereof in the form of a purified recombinant vacA polypeptide.

In another further aspect, the present invention provides VacA polypeptides of the invention, including fragments and variants thereof in the form of VacA polypeptide composition essentially pure, i.e. essentially free from other native extract antigen components such as CagA and or NAP (neutrophil activating protein). For example, such essentially pure VacA polypeptide composition can be obtained from mutated *H. pylori* strains that have the other component(s)'s genes knocked out such as where the CagA gene is knocked out.

The preparation of VacA polypeptide, fragments and variants thereof according to the invention recombinantly, can be achieved by various techniques known in the art. Nucleic acid sequence encoding for said vacA polypeptide, fragments and variants thereof can be inserted in the recombinant expression vector by methods well known to a person skilled in the art such as, for example, those that are described in *MOLECULAR CLONING: A LABORATORY MANUAL*, Sambrook et al., 4$^{th}$ Ed., Cold spring Harbor Laboratory Press, Cold spring Harbor, N.Y., 2001.

In a further embodiment, it is provided a host cell comprising a recombinant vector according to the invention.

The introduction of the recombinant vector in a host cell can be carried out according to methods that are well known to a person skilled in the art, such as those described in *BASIC METHODS IN MOLECULAR BIOLOGY*, Davis et al., 2nd ed., McGraw-Hill professional publishing, 1995, and *MOLECULAR CLONING: A LABORATORY MANUAL*, supra, such as transfection by calcium phosphate, transfection by DEAE dextran, transfection, microinjection, transfection by cationic lipids, electroporation, transduction or infection.

The host cell can be, for example, bacterial cells such as *E. coli*, cells of fungi such as yeast cells and cells of *Aspergillus, Streptomyces*, insect cells, Chinese Hamster Ovary cells (CHO), C127 mouse cell line, BHK cell line of Syrian hamster cells, Human embryonic Kidney 293 (HEK 293) cells. In a particular embodiment, the host cell is a CHO cell or a HEK 293 cell.

The host cells can be used, for example, to express a polypeptide of the invention. After purification by standard methods, the polypeptide of the invention can be used in a method described hereinafter.

For instance, when expression systems that secrete the recombinant protein are employed, the culture medium may first be concentrated using a commercially available protein concentration filter, for example, an ultrafiltration unit. Following the concentration step, the concentrate can be applied to a purification matrix such as a gel filtration medium. Alternatively, an anion exchange and/or an affinity resin can be employed. The matrices can be acrylamide, agarose, dextran, cellulose or other types commonly employed in protein purification. Alternatively, a cation exchange step can be employed. Some or all of the foregoing purification steps, in various combinations, are well known and can be employed to provide a substantially homogeneous recombinant protein.

Recombinant polypeptides produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Microbial cells can be disrupted by any convenient method, including freeze-thaw cycling, sonication, mechanical disruption, or use of cell lysing agents.

In another aspect, VacA polypeptide of the invention can be prepared recombinantly as a full length protein as described in McClain et al., 2003, *J. Biol. Chem.*, 278: 12101-12108, or through the reconstitution of its two domains, p33 and p55, in the presence of detergents as described in Gonzalez-Rivera et al., 2010, *Biochemistry* 49:5743-5752.

In another aspect, the present invention provides variants or fragments of the VacA polypeptides described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In another aspect, the VacA polypeptide, fragments and variants thereof can be used associated with a pharmaceutically acceptable salt or a combinations of pharmaceutically acceptable salts.

Compositions

The invention provides *H. pylori* extracts, *H. pylori* extract components, a VacA polypeptide, variants or fragments thereof, pharmaceutical compositions thereof, and methods for treating a patient, preferably a mammalian patient, and most preferably a human patient who is suffering from a hypersensitivity to an inflammatory bowel disease or a risk of developing inflammatory bowel disease, in particular Crohn's disease or ulcerative colitis (UC).

According to another aspect, the invention provides *H. pylori* extracts (from wild type or mutant bacteria as described above), *H. pylori* extract components, a VacA polypeptide, variants or fragments thereof, pharmaceutical compositions thereof and methods for controlling hypersensitivity/irritability of the colon and/or small intestine, in particular inducing a protection of the colon and/or small intestine against hypersensitivity/irritability such as increasing secretion of protective mucus and production of anti-inflammatory cytokines (e.g. IL-10 and TGF-β).

In a particular embodiment, the invention provides *H. pylori* extracts, *H. pylori* extract components, VacA polypeptide, variants or fragment thereof and a pharmaceutical formulation according to the invention for use as a medicament.

Pharmaceutical compositions of the invention can contain at least one *H. pylori* extracts, *H. pylori* extract component, VacA polypeptide, variants or fragment thereof according to the invention in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to a particular embodiment, compositions according to the invention are injectable.

Compositions of this invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Further materials as well as formulation processing techniques and the like are set out in Part 5 of *Part 5 of Remington's "The Science and Practice of Pharmacy"*, $22^{nd}$ *Edition*, 2012, University of the Sciences in Philadelphia, Lippincott Williams & Wilkins the content of which is incorporated herein by reference.

Compositions of this invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions of this invention may also be formulated for inhalation, which may be in a form including, but not limited to, a solution, suspension, or emulsion that may be administered as a dry powder or in the form of an aerosol using a propellant.

The compounds of this invention can also be administered in sustained release forms or from sustained release drug delivery systems.

In certain embodiments, the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

According to one aspect, the invention provides an oral pharmaceutical composition.

According to one aspect, the invention provides an intraperitoneal pharmaceutical composition.

As described elsewhere herein, in certain embodiments, a prophylactic/therapeutically effective dose of an *H. pylori* extract, an *H. pylori* extract component, a VacA polypeptide, variant or fragment thereof, a pharmaceutical composition thereof are used herein in a dose sufficient to induce decrease hypersensitivity/irritability of the colon and/or small intestine or hyperreactivity to coeliac disease, as measured using any of a variety of methods as described herein such as calprotectin in stool, colonoscopy with biopsy of pathological lesions (in IBD), and serological assessment of antibodies to the enzyme tissue transglutaminase (tTG) (in coeliac disease.

Mode of Administration

Extracts, extract components, polypeptides and compositions of this invention may be administered in any manner including intravenous injection, intraperitoneal injection, subcutaneous injection, oral route, intranasal administration, intrapulmonary instillation or by inhalation. In certain embodiments, a combination of different routes may also be used.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

For instance, as few as one or a few doses (e.g., fewer than about three, or fewer than about five doses) of agent may be sufficient to induce an effective reduction of hypersensitivity/irritability of the colon and/or small intestine. By way of example, a daily or about 2 to 3 times a week or weekly from about 0.5 to about 5 g of cell extract (or equivalent in extract component)/dose might be used to achieve protective effects.

According to one embodiment, polypeptides and compositions of the invention are administered before of at the beginning of the onset of the hypersensitivity/irritability of the colon and/or small intestine symptoms.

Combination

According to the invention, an *H. pylori* extract, an *H. pylori* extract component, a Vac A polypeptide, a variant or fragment thereof and pharmaceutical formulations thereof can be administered alone or in combination with a co-agent useful in the prevention and/or treatment of hypersensitivity/irritability of the colon and/or small intestine, in particular Inflammatory Bowel Disease such Crohn's disease and ulcerative colitis, e.g. for example a co-agent such as an anti-inflammatory agent, a TNFα antagonist—infliximab, adalimumab, certolizumab pegol—other biologics currently in clinical development targeting cytokines involved in IBD pathogenesis (IL-12 and IL-23), or the α4137 integrin. Possible co-agents further include live helminths (*Heligmosomoides polygyrus, Trichuris suis*) or probiotics (*Lactobacillus, Bifidobacterium* species or the *Escherichia coli* strain Nissle) or components thereof.

The invention encompasses the administration of a Vac A polypeptide, a variant or fragment thereof and pharmaceutical formulations thereof to an individual prior to, simultaneously or sequentially with other therapeutic/prophylactic regimens or co-agents in the prevention or treatment of particular Inflammatory Bowel Disease, in particular Crohn's disease and ulcerative colitis (e.g. combined drug regimen), or of coeliac disease in a therapeutically effective amount. An a *H. pylori* extract, an *H. pylori* extract component, a Vac A polypeptide, a variant or fragment thereof, or the pharmaceutical formulation thereof that is administered simultaneously with said co-agents can be administered in the same or different composition(s) and by the same or different route(s) of administration.

According to one embodiment, is provided a pharmaceutical formulation comprising at least one of a *H. pylori* extract, an *H. pylori* extract component, a Vac A polypeptide, a variant or fragment thereof, combined with at least one co-agent useful in the prevention and/or treatment of Inflammatory Bowel Disease in particular Crohn's disease and ulcerative colitis, and coeliac disease, at least one pharmaceutically acceptable carrier, diluent or excipient thereof.

Patients

In an embodiment, patients according to the invention are patients suffering from an Inflammatory Bowel Disease disorders such as Crohn's disease, ulcerative colitis, lymphocytic colitis, ischemic colitis, Bechet's disease, diversion colitis, and irritable bowel syndrome, or coeliac disease.

In another embodiment, patients according to the invention are patients at risk of suffering from Crohn's disease.

In another further embodiment, patients according to the invention are suffering from colitis such as lymphocytic colitis, ischemic colitis, diversion colitis and ulcerative colitis.

In another further embodiment, patients according to the invention are suffering from ulcerative colitis.

In another further embodiment, patients according to the invention are suffering from coeliac disease or at risk of suffering from coeliac disease due to family history.

In another embodiment, patients according to the invention are patients at risk of suffering from hypersensitivity/irritability of the colon and/or small intestine.

Use According to the Invention

In accordance with one aspect of the present invention, there is provided a method for decreasing the hypersensitivity/irritability of the colon and/or small intestine in a subject by use of a polypeptide or a formulation or a combination as described herein. The an *H. pylori* extract, *H. pylori* extract component or polypeptide, a fragment or a variant thereof or formulation or combination according to the invention is administered in an amount and in accordance with a dosage regimen that is effective for decreasing the hypersensitivity/irritability of the colon and/or small intestine in a subject.

In one embodiment of the invention is provided a use of a polypeptide or a formulation thereof according to the invention for the preparation of a pharmaceutical composition for the prevention, repression and/or treatment of Inflammatory Bowel Disease disorder, in particular Crohn's disease or ulcerative colitis.

In another embodiment of the invention is provided a use of an *H. pylori* extract or an *H. pylori* extract component or a polypeptide or a formulation thereof according to the invention for the preparation of a pharmaceutical composition for the repression or treatment of hypersensitivity/irritability of the colon and/or small intestine.

According to a particular aspect, the *H. pylori* extract or *H. pylori* extract component or a polypeptide or a formulation thereof according to the invention are formulations which protective of the gastrointestinal mucosae.

In another embodiment of the invention is provided a method for preventing, repressing or treating Inflammatory Bowel Disease disorder, in particular Crohn's disease or ulcerative colitis in a subject, said method comprising administering in a subject in need thereof a therapeutically effective amount of an *H. pylori* extract or an *H. pylori* extract component or a polypeptide according to the invention, a fragment or a variant thereof, or a pharmaceutical formulation thereof according to the invention.

In a further embodiment of the invention is provided a use or a method according to the invention, wherein the subject is predisposed or at risk to develop hypersensitivity/irritability of the colon and/or small intestine, for example based on familial history, personal history, any of the symptoms listed above, or age.

According to another embodiment, the invention relates to a pharmaceutical formulation comprising at least one from an *H. pylori* extract or an *H. pylori* extract component, a polypeptide selected from a Vac A protein, a fragment or a variant thereof, combined with at least one co-agent useful in the prevention, repression and/or treatment of hypersensitivity/irritability of the colon and/or small intestine, and at least one pharmaceutically acceptable carrier, diluent or excipient thereof.

In another embodiment, is provided a polypeptide, a composition or a method according to the invention wherein said *H. pylori* extract, *H. pylori* extract component or polypeptide or a composition thereof is to be administered by the oral, intranasal, intraperitoneal, parenteral or systemic route.

In another embodiment, is provided polypeptide, a composition or a method according to the invention wherein VacA is s1m1 VacA.

In another embodiment, is provided polypeptide, a composition or a method according to the invention wherein VacA is s2m2 VacA.

In another embodiment, is provided polypeptide, a composition or a method according to the invention wherein VacA is a Vac A protein comprising an amino acid sequence selected from SEQ ID NO: 1, 2, 3, 4, 5, 6, 7, 8, 9 and 10.

In another embodiment, is provided polypeptide, a composition or a method according to the invention wherein VacA is a Vac A protein comprising an amino acid sequence of SEQ ID NO: 1 or a fragment or a variant thereof.

In another embodiment, is provided polypeptide, a composition or a method according to the invention wherein VacA is a Vac A protein comprising an amino acid sequence of SEQ ID NO: 2 or a fragment or a variant thereof.

In another embodiment, is provided a medicinal kit comprising an *H. pylori* extract or an *H. pylori* extract component, a polypeptide selected from a Vac A protein, a fragment or a variant thereof according to the invention together with instructions of use.

Examples illustrating the invention will be described hereinafter in a more detailed manner and by reference to the embodiments represented in the Figures.

EXAMPLES

The following abbreviations refer respectively to the definitions below:
DSS (Dextran sulfate sodium), IBD (Inflammatory Bowel Disease), TNF-α (tumor necrosis factor alpha).

Example 1

*H. pylori* Extract Relieves the Clinical and Histopathological Features of DSS-Induced Colitis To assess whether regular administration of compositions of the invention provided in the form of a *H. pylori* extracts (dead cells) protects against IBD in a mouse model, mice were subjected to DSS-induced colitis. C57BL/6 mice were either intragastrically infected with $10^8$ live *H. pylori* strain PMSS1 (Arnold et al. 2011, supra) secreting s1m1 VacA at 6 weeks of age (i.e. as neonates) or received three-times weekly intragastric doses of 200 μg *H. pylori* extract that was prepared by pressure homogenization of freshly harvested logarithmic phase *H. pylori* bacteria as described below during a-six-week-long course of DSS treatment. The DSS model of IBD-like pathology involves treating mice starting at six weeks of age with three five day courses of 2% DSS in the drinking water, with the three DSS cycles being separated by one-week long compound-free intervals.

At the study endpoint, mice were examined by high resolution colonoscopy, and assessed with respect to colonic pathology. Colonoscopy scores on a scale of 0-15 were assigned by an experienced endoscopist operating a specially designed mini-endoscope (Becker et al, 2006, *Nat. Protoc.*, 1:2900-4). Histopathology scores on a scale of 0-5 were assigned based on published criteria (Oertli et al., 2011, *Journal of Immunology* 187, 3578-86) and representative endoscopic as well as histopathologic images of all treatment groups are represented under FIG. 1. Histopathological evaluation of the most distal part of the colon with respect to inflammation and epithelial changes revealed that all mice subjected to the DSS protocol had developed moderate to severe colitis, as evidenced by the widespread loss of goblet cells and of crypts, accompanied by extensive mucosal and submucosal infiltration of inflammatory cells (FIG. 1A,B).

In contrast, *H. pylori*-infected mice exhibited significantly less inflammation and had also undergone less substantial epithelial changes. Interestingly, a similar beneficial effect was observed in mice that were subjected to three-times weekly administration of intragastric doses of *H. pylori* dead cell extract. Overall, the histopathological scores assigned independently for the parameters "inflammation" and "epithelial changes" were significantly lower in the two treatment arms exposed to live *H. pylori* or its extract relative to the positive controls (FIG. 1A,B). Similar results were obtained in five independent studies, of which three were pooled for FIG. 1.

High resolution endoscopy was used (as described in Becker et al., 2006 supra) to assess colitis in a subset of the mice shown in FIG. 1A; whereas DSS-treated mice were characterized by thickening and intransparency of the colon, mucosal bleeding, abundant fibrin, and loose stools, all of these parameters were less severe in the *H. pylori* extract-treated mice (FIG. 1C, D). Consequently, the overall colonoscopy scores assigned on a scale from 0-15 for the above-mentioned parameters was reduced from on average 10 (positive controls) to 5 (infected and extract treated; FIG. 1D). Interestingly, lower doses of dead cell extract (see below for protocol of preparation) (<10 mg/kg body weight), or once-weekly treatment with the 10 mg/kg dose, were not sufficient to confer protection. In contrast, the level of protection achieved by treatment during the third cycle only, i.e. at a time when colonic pathology is already established, is comparable to the protection conferred by continuous treatment throughout all six weeks of the DSS protocol.

Surprisingly, intraperitoneal injection of *H. pylori* dead cell extract conferred a level of protection that was quite similar to the protection provided by orogastric delivery of the dead extract (FIG. 1A-D). Heat-inactivated *H. pylori* extract failed to provide protection.

The combined results indicate that *H. pylori* infection as well as regular treatment with native *H. pylori* dead cell extract—delivered orally or systemically—prevents the clinical and histopathological features characteristic of DSS-induced colitis and may also be effective at alleviating pre-existing disease.

Example 2

Role of *H. pylori* Extracts on Lymphopenic Recipients of Adoptively Transferred Naive CD4+ T-Cells In order to rule out that the observed protective effects are specific to the DSS model of barrier disruption followed by microbiota-induced autoinflammation, the efficacy of dead cell extract treatment in an alternative, T-cell transfer-mediated model of colitis was assayed.

Lymphopenic mice lacking T-cells due to a mutation of their T-cell receptor received 400.000 naive CD4+ T-cells (Leach et al. 1996, *Am. J. Pathol.*, 148(5):1503-15) were either treated with three-times weekly doses of 200 μg *H. pylori* extract prepared as described above or remained untreated. All mice were sacrificed five weeks after T-cell transfer. Colonoscopy scores on a scale of 0-15 and histopathology grades on a scale of 0-5 were obtained as described above, total body weight was measured as a general indicator of well-being and TNF-α levels as determined by real time PCR as a readout for T-cell-specific cytokine production.

Figure 2:
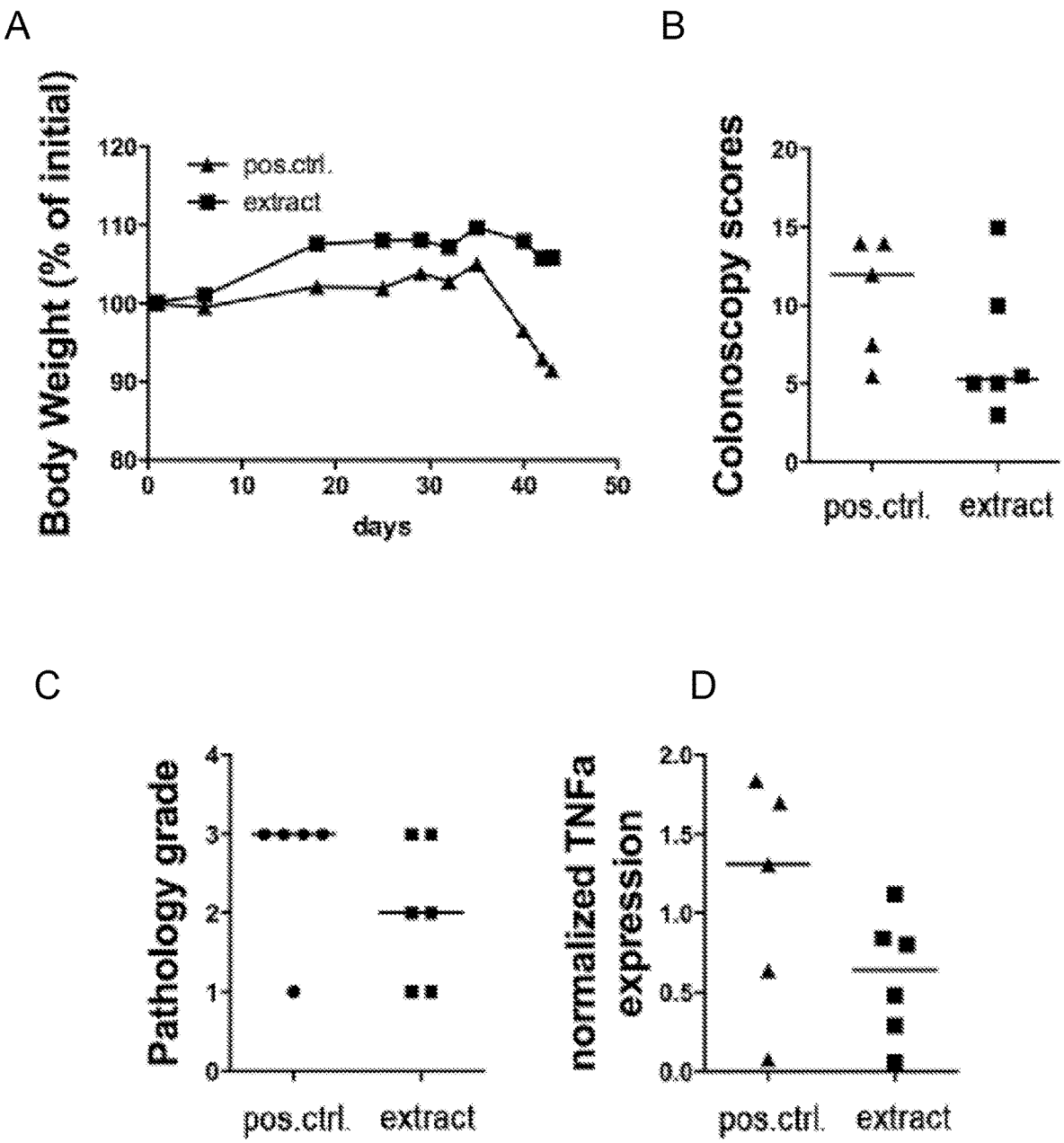
FIG. 2 shows that the regular intragastric (oral) treatment with *H. pylori* extract effectively reduces the pathology associated with T-cell transfer colitis in mice as described in Example 2. A: total body weight as indicator of the well-being of the animals; B: colonoscopy scores on a scale of 0-15; C: histopathology scores on a scale of 0-5; D: TNF-α levels by real time PCR for measuring T-cell-specific cytokine production.

Whereas the recipients of naive T-cells all developed severe colitis with a median histopathology score of 4 (FIG. 2A,B) and a median endoscopy score of 10 (FIG. 2C,D), both scores were strongly reduced in extract-treated animals (FIG. 2A-D). The protective effect conferred by dead cell extract treatment was further reflected higher body weights, and lower production of mucosal TNFα as determined by real time PCR (FIG. 2D).

All indicated parameters are thus consistent with a strong protective effect of H. pylori dead cell extract on the development of colitis in two models of IBD.

Example 3

Preparation of Purified H. pylori Dead Cell Extracts Components of the Invention H. pylori strain PMSS1 (Arnold et al. 2011, supra) secreting s1m1 VacA was cultured in Brucella broth supplemented with 10% FCS, pelleted by centrifugation and washed once with PBS. Bacteria were subjected to three freeze/thaw cycles and disrupted by three passes through a French pressure cell press (Stansted Fluid Power, Cell Pressure Homogenizer) at 30.000 bars. Cell debris were removed by centrifugation and the supernatant filtered through a 2 μm filter leading to the dead cell extracts used in the present examples. Protein concentrations were determined by BCA Protein Kit (R&D systems).

For example, H. pylori VacA is purified from H. pylori culture supernatants using previously published procedures (Cover et al., 1992, J. Biol. Chem., 267:10570-1057; Cover et al., 1997, J. Cell. Biol., 138:759-769), with the following slight modifications. H. pylori strain ATCC 49503/60190 which was first described in 1990 (Cover et al., 1990, Infect. Immun. 58: 603-610) is cultured in sulfite-free Brucella broth containing either cholesterol or 0.5% charcoal. After centrifugation of the culture, supernatant proteins are precipitated with a 50% saturated solution of ammonium sulfate. The oligomeric form of VacA is isolated by gel filtration chromatography with a Superose 6 HR 16/50 column in PBS containing 0.02% sodium azide and 1 mM EDTA.

The invention claimed is:

1. A method of treating a disease or disorder selected from an inflammatory bowel disease (IBD), ulcerative colitis, Crohn's disease, colitis, and coeliac disease in a subject in need thereof, said method comprising administering to the subject in need thereof a therapeutically effective amount of an *H. pylori* extract or an *H. pylori* extract component or a composition thereof, wherein said *H. pylori* extract or *H. pylori* extract component or a composition thereof comprises a VacA protein selected from SEQ ID NO: 1, 2, 3, 4, 5, 6, 7, 8, 9 or 10 and wherein said *H. pylori* extract or *H. pylori* extract component or a composition thereof is essentially free from other immunogenic *H. pylori* antigen components.

2. The method according to claim 1, wherein said *H. pylori* extract component consists of a VacA protein selected from SEQ ID NO: 1, 2, 3, 4, 5, 6, 7, 8, 9 or 10 and is essentially free from other immunogenic *H. pylori* antigen components.

3. The method according to claim 1, wherein the *H. pylori* bacteria strain is deposited at the ATCC under accession number 45903, strain designation 60190.

4. The method according to claim 1, wherein the component is purified from extracts from non-denatured killed *H. pylori* bacteria cells.

5. The method according to claim 1, wherein said VacA protein is recombinant VacA.

6. The method according to claim 1, wherein the disease or disorder is an inflammatory bowel disease.

7. The method according to claim 1, wherein the inflammatory bowel disease is ulcerative colitis.

8. The method according to claim 1, wherein the inflammatory bowel disease is Crohn's disease.

9. The method according to claim 1, wherein the disease or disorder is coeliac disease.

10. The method according to claim 1, wherein the disease or disorder is colitis.

11. The method according to claim 10, wherein said colitis is lymphocytic colitis, ischemic colitis, diversion colitis or ulcerative colitis.

12. The method according to claim 1, wherein the extract or extract component is administered by an oral, intranasal, parenteral, intraperitoneal or systemic route.

13. The method according to claim 1, wherein the composition is a pharmaceutical composition comprising a VacA protein selected from SEQ ID NO: 1, 2, 3, 4, 5, 6, 7, 8, 9 or 10 and at least one pharmaceutically acceptable carrier, diluent or excipient thereof, wherein the VacA protein is essentially free from other immunogenic *H. pylori* antigen components.

* * * * *

UNITED STATES PATENT AND TRADEMARK OFFICE
CERTIFICATE OF CORRECTION

PATENT NO. : 11,166,986 B2
APPLICATION NO. : 15/115391
DATED : November 9, 2021
INVENTOR(S) : Anne Mueller and Daniela Engler-Anders Page 1 of 1

It is certified that error appears in the above-identified patent and that said Letters Patent is hereby corrected as shown below:

In the Specification

Column 3,
Lines 34-36, "or a pharmaceutical formulation thereof.
DESCRIPTION OF THE FIGURES" should read
--or a pharmaceutical formulation thereof.
A sixth aspect of the invention relates to a pharmaceutical formulation comprising at least one of an *H. pylori* extract, an *H. pylori* extract component, a polypeptide of the invention, a fragment or a variant thereof, combined with at least one co-agent useful in the prevention and/or treatment of inflammatory bowel diseases (IBDs), in particular Crohn's disease (CD) and ulcerative colitis (UC), as well as coeliac disease, and at least one pharmaceutically acceptable carrier, diluent or excipient thereof.
DESCRIPTION OF THE FIGURES--.

Column 9,
Line 22, "vacA" should read --VacA--.
Line 25, "vacA" should read --VacA--.
Line 40, "vacA" should read --VacA--.

Signed and Sealed this
Twenty-fourth Day of May, 2022

Katherine Kelly Vidal
*Director of the United States Patent and Trademark Office*